US006436409B1

(12) United States Patent
Gicquel et al.

(10) Patent No.: US 6,436,409 B1
(45) Date of Patent: Aug. 20, 2002

(54) **POLYNUCLEOTIDE FUNCTIONALLY CODING FOR THE LHP PROTEIN FROM *MYCOBACTERIUM TUBERCULOSIS*, ITS BIOLOGICALLY ACTIVE DERIVATIVE FRAGMENTS, AS WELL AS METHODS USING THE SAME**

(75) Inventors: Brigitte Gicquel; Francois-Xavier Berthet, both of Paris (FR); Peter Andersen, Bronshoj; Peter Birk Rasmussen, Kobehavn, both of (DK)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/116,492

(22) Filed: Jul. 16, 1998

Related U.S. Application Data

(60) Provisional application No. 60/052,631, filed on Jul. 16, 1997, now abandoned.

(51) Int. Cl.$^7$ .......................... A61K 39/04; C12Q 1/68; C12P 19/34; C12N 1/12; C07H 21/04
(52) U.S. Cl. .................. 424/248.1; 435/6; 435/91.1; 435/91.2; 435/253.1; 435/863; 530/350; 536/24.32; 536/24.33
(58) Field of Search ..................... 424/248.1; 435/6, 435/91.1, 91.2, 253.1, 863; 530/350; 536/24.32, 24.33

(56) References Cited

U.S. PATENT DOCUMENTS 5,597,911 A 1/1997 Guesdon et al. ......... 936/24.32

OTHER PUBLICATIONS

Eiglmeier et al, "Use of an ordered cosmid library to deduce the genomic organization of *Mycobacterium leprae*", Molecular Microbiology, vol. 7, No. 2 pp. 197–206, Jan. 1993.*

Andersen et al, "Recoll of long–lived immunity to *Mycobacterium tuberculosis* infection in mice", J. Immunology, vol. 154, pp. 3359–3372, Jan. 1995.*

Mahairas et al, "Molecular analysis of genetic differences between *Mycobacterium bovis* BCG and Virulent *M. bovis*", J. Bacteriol., vol. 178, No. 5, pp. 1274–1282, Jan. 1993.*

* cited by examiner

*Primary Examiner*—Rodney P Swartz
(74) *Attorney, Agent, or Firm*—Oblon, Spivak, McClelland, Maier & Neustadt, P.C.

(57) ABSTRACT

The present invention is directed to a polynucleotide carrying an open reading frame coding for an antigenic polypeptide from *Mycobacterium tuberculosis*, named lhp, which is placed under the control of its own regulation signals which are functional in mycobacteria, specially in mycobacteria belonging to the *Mycobacterium tuberculosis* complex and also in fast growing mycobacteria such as *Mycobacterium smegmatis*. The invention is also directed to the polypeptide LHP encoded by lhp and most preferably to suitable antigenic portions of LHP as well as to oligomeric polypeptides containing more than one unit of LHP or an antigenic portion of LHP. The invention concerns also immunogenic and vaccine compositions containing a polypeptide or an oligomeric polypeptide such as defined above, as well as antibodies directed specifically against such polypeptides that are useful as diagnostic reagents. In another embodiment, the present invention is directed to a polynucleotide carrying the natural regulation signals of lhp which is useful in order to express heterologous proteins in mycobacteria. Finally, the present invention is directed to oligonucleotides comprising at least 12 consecutive nucleotides from the regulation sequence of lhp which are useful as reagents for detecting the presence of *Mycobacterium tuberculosis* in a biological sample.

26 Claims, 17 Drawing Sheets

FIG. 5A.1

```
          10        30        50        70
CTGCAGGAGGTGACGTCGTTGTTCAGCCAGGTGGGCGGCACCGGCGGCGGCAACCCAGCGGCAACCCAGCGGAAGCCGCAGAT
          90       110       130       150

GGGCCTGCTCGGCACCAGTCGGCTGTGCGAACCATCGCTGGCTGGTGGATCAGGCCCCAGGCGGCGGCGGGCTGCTGC
         170       190       210       230

GCGCGGAGTCGCTACCTGGCGCAGGTGGGTCGTTGACCGGCACGCCGGCTGATGTCTCAGCTGAAAAGCCGGTTGCC
         250       270       290       310

CCCTCGGTGATGCCGGCGGTGTTGCCGGATCGTCGGTGACGGGTGGCCGCGGTGGTCCGGTGGTCCGGGAGCGATGGGCCA
         330       350       370       390

GGGTTCGGCAATCCGGCGGCTCCACCAGCCGGGTCTGGTCGGCGGGCACCGCTCGGCGCAGGAGCGTGAAGAGACGACG
         410       430       450       470
                                       +1 Mtb.
AGGACGACTGGGACGAAGAGGACGACTGGTGGTGAGCTCCCGTAATGACAACAGACTTCCCGGCCACCCGGGCCGGAAGACTT
```

```
       490              510   +1 Ms    530                  550
         .                .      .       .          .         .
GCCAACATTTTGGCGAGGAAGGTAAAAGAGAGAaAGTAGTCCAGCATGGCAGAGATGAAGACCGATGCCGCTACCCTCGGG
                         RBS ▲              M  A  E  M  K  T  D  A  A  T  L  G 570              590                610                  630
          .                .                  .                    .
CAGGAGGCAGGTAATTTCGAGCGGATCTCCGGGGACCTGAAAACCCAGATCGACCAGGTGGAGTCGACGGCAGGTTCGTT
 Q  E  A  G  N  F  E  R  I  S  G  D  L  K  T  Q  I  D  Q  V  E  S  T  A  G  S  L 650              670                690                  710
          .                .                  .                    .
GCAGGGCCAGTGGCGCGGCGCGGGGACGCGGCCCAGGCCGCGGTGGTGCGCTTCCAAGAAGCAGCCAATAAGCAGA
 Q  G  Q  W  R  G  A  A  G  T  A  A  Q  A  A  V  V  R  F  Q  E  A  A  N  K  Q  K 730              750                770                  790
          .                .                  .                    .
AGCAGGAACTCGACGAGATCTCGACGAATATTCGTCAGGCCGGCGTCCAATACTCGAGGGCCGACGAGGAGCAGCAG
 Q  E  L  D  E  I  S  T  N  I  R  Q  A  G  V  Q  Y  S  R  A  D  E  E  Q  Q  Q 810              830                850
          .                .                  .
GCGCTGTCCTCGCAAATGGGCTTCTGACCCGCTAATACGAAAAGAAAACGGAGCAAAAACATGACAGAG--> esat-6
 A  L  S  S  Q  M  G  F  *                                    M  T  E
```

FIG. 5A.2

```
Mtb LHP     MAEMKTDAATLGQEAGNFERISGDLKTQIDQVESTAGSLQGQWRGAAGTA
            |||| |:||.|.|:|:.|:.|.::|. : :|:|.:.|:|. | |.|:.|
Mlep L45    MAEMITEAAILTQQAAQFDQIASGLSQERNFVDSIGQSFQNTWEGQAASA Mtb LHP     AQAAVVRFQEAANKQKQELDEISTNIRQAGVQYSRADEEQQQALSSQMGF
            | :|:.||:|| ..|.: |:.|..:...|..| .:.|:|..| |||.|.|
Mlep L45    ALGALGRFDEAMQDQIRQLESIVDKLNRSGGNYTKTDDEANQLLSSKMNF
```

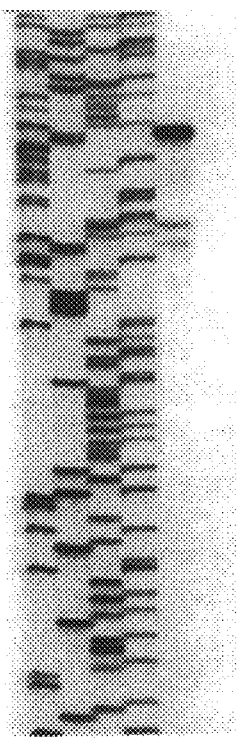
FIG. 6A
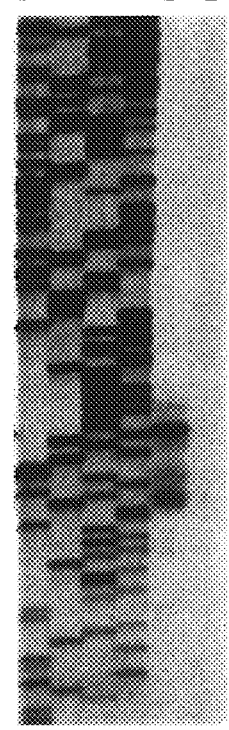
FIG. 6C
AAGACGACGAGGACGACTGGGACGAAGAGGACGACTGGTGAGCTC
                        -35
CCGTAATGACAACAGACTTCCCGGCCACCCGGGCCGGAAGACTTG
    -10                 T₁                    T₂   T₃
FIG. 6B

SEQUENCE LISTING

<160> NUMBER OF SEQ ID NOS: 39

<210> SEQ ID NO 1
<211> LENGTH: 1277
<212> TYPE: DNA
<213> ORGANISM: Mycobacterium tuberculosis

<400> SEQUENCE: 1

| | | | | |
|---|---|---|---|---|
| ctgcagcagg | tgacgtcgtt | gttcagccag | gtgggcggca | ccggcggcgg caacccagcc | 60 |
| gacgaggaag | ccgcgcagat | gggcctgctc | ggcaccagtc | cgctgtcgaa ccatccgctg | 120 |
| gctggtggat | caggccccag | cgcgggcgcg | ggcctgctgc | gcgcggagtc gctacctggc | 180 |
| gcaggtgggt | cgttgacccg | cacgccgctg | atgtctcagc | tgatcgaaaa gccggttgcc | 240 |
| ccctcggtga | tgccggcggc | tgttgccgga | tcgtcggtga | cgggtggcgc cgctccggtg | 300 |
| ggtccgggag | cgatgggcca | gggttcgcaa | tccggcggct | ccaccagccc gggtctggtc | 360 |
| gcgccggcac | cgctcgcgca | ggagcgtgaa | gaagacgacg | aggacgactg gacgaagag | 420 |
| gacgactggt | gagctcccgt | aatgacaaca | gacttcccgg | ccacccgggc cggaagactt | 480 |
| gccaacattt | tggcgaggaa | ggtaaagaga | gaaagtagtc | cagcatggca gagatgaaga | 540 |
| ccgatgccgc | taccctcggg | caggaggcag | gtaatttcga | gcggatctcc ggcgacctga | 600 |
| aaacccagat | cgaccaggtg | gagtcgacgg | caggttcgtt | gcagggccag tggcgcggcg | 660 |
| cggcggggac | ggccgcccag | gccgcggtgg | tgcgcttcca | agaagcagcc aataagcaga | 720 |
| agcaggaact | cgacgagatc | tcgacgaata | ttcgtcaggc | cggcgtccaa tactcgaggg | 780 |
| ccgacgagga | gcagcagcag | gcgctgtcct | cgcaaatggg | cttctgaccc gctaatacga | 840 |
| aaagaaacgg | agcaaaaaca | tgacagagca | gcagtggaat | ttcgcgggta tcgaggccgc | 900 |
| ggcaagcgca | atccagggaa | atgtcacgtc | cattcattcc | ctccttgacg aggggaagca | 960 |
| gtccctgacc | aagctcgcag | cggcctgggg | cggtagcggt | tcggaggcgt accagggtgt | 1020 |
| ccagcaaaaa | tgggacgcca | cggctaccga | gctgaacaac | gcgctgcaga acctggcgcg | 1080 |
| gacgatcagc | gaagccggtc | aggcaatggc | ttcgaccgaa | ggcaacgtca ctgggatgtt | 1140 |
| cgcatagggc | aacgccgagt | tcgcgtagaa | tagcgaaaca | cgggatcggg cgagttcgac | 1200 |
| cttccgtcgg | tctcgccctt | tctcgtgttt | atacgtttga | gcgcactctg agaggttgtc | 1260 |
| atggcggccg | actacga | | | | 1277 |

<210> SEQ ID NO 2
<211> LENGTH: 524
<212> TYPE: DNA
<213> ORGANISM: Mycobacterium tuberculosis

<400> SEQUENCE: 2

```
ctgcagcagg tgacgtcgtt gttcagccag gtgggcggca ccggcggcgg caacccagcc     60
gacgaggaag ccgcgcagat gggcctgctc ggcaccagtc cgctgtcgaa ccatccgctg    120
gctggtggat caggccccag cgcgggcgcg ggcctgctgc gcgcggagtc gctacctggc    180
gcaggtgggt cgttgacccg cacgccgctg atgtctcagc tgatcgaaaa gccggttgcc    240
ccctcggtga tgccggcggc tgttgccgga tcgtcggtga cgggtggcgc cgctccggtg    300
ggtccgggag cgatgggcca gggttcgcaa tccggcggct ccaccagccc gggtctggtc    360
gcgccggcac cgctcgcgca ggagcgtgaa gaagacgacg aggacgactg ggacgaagag    420
gacgactggt gagctcccgt aatgacaaca gacttcccgg ccacccgggc cggaagactt    480
```

```
gccaacattt tggcgaggaa ggtaaagaga gaaagtagtc cagc                      524

<210> SEQ ID NO 3
<211> LENGTH: 481
<212> TYPE: DNA
<213> ORGANISM: Mycobacterium tuberculosis

<400> SEQUENCE: 3
ctgcagcagg tgacgtcgtt gttcagccag gtgggcggca ccggcggcgg caacccagcc       60
gacgaggaag ccgcgcagat gggcctgctc ggcaccagtc cgctgtcgaa ccatccgctg      120
gctggtggat caggccccag cgcgggcgcg ggcctgctgc gcgcggagtc gctacctggc      180
gcaggtgggt cgttgacccg cacgccgctg atgtctcagc tgatcgaaaa gccggttgcc      240
ccctcggtga tgccggcggc tgttgccgga tcgtcggtga cgggtggcgc cgctccggtg      300
ggtccgggag cgatgggcca gggttcgcaa tccggcggct ccaccagccc gggtctggtc      360
gcgccggcac cgctcgcgca ggagcgtgaa gaagacgacg aggacgactg ggacgaagag      420
gacgactggt gagctcccgt aatgacaaca gacttcccgg ccacccgggc cggaagactt      480
g                                                                     481

<210> SEQ ID NO 4
<211> LENGTH: 302
<212> TYPE: DNA
<213> ORGANISM: Mycobacterium tuberculosis

<400> SEQUENCE: 4
atggcagaga tgaagaccga tgccgctacc ctcgggcagg aggcaggtaa tttcgagcgg       60
atctccggcg acctgaaaac ccagatcgac caggtggagt cgacggcagg ttcgttgcag      120
ggccagtggc gcgcgcggc ggggacggcc gcccaggccg cggtggtgcg cttccaagaa      180
gcagccaata agcagaagca ggaactcgac gagatctcga cgaatattcg tcaggccggc      240
gtccaatact cgagggccga cgaggagcag cagcaggcgc tgtcctcgca aatgggcttc      300
tg                                                                    302

<210> SEQ ID NO 5
<211> LENGTH: 100
<212> TYPE: PRT
<213> ORGANISM: Mycobacterium tuberculosis

<400> SEQUENCE: 5

Met Ala Glu Met Lys Thr Asp Ala Ala Thr Leu Gly Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Ala Leu Ser Ser
                85                  90                  95

Gln Met Gly Phe
            100
```

<210> SEQ ID NO 6
<211> LENGTH: 49
<212> TYPE: PRT
<213> ORGANISM: Mycobacterium tuberculosis

<400> SEQUENCE: 6

Met Ala Glu Met Lys Thr Asp Ala Ala Thr Leu Gly Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr

<210> SEQ ID NO 7
<211> LENGTH: 42
<212> TYPE: PRT
<213> ORGANISM: Mycobacterium tuberculosis

<400> SEQUENCE: 7

Gln Glu Ala Ala Asn Lys Gln Lys Gln Glu Leu Asp Glu Ile Ser Thr
1               5                   10                  15

Asn Ile Arg Gln Ala Gly Val Gln Tyr Ser Arg Ala Asp Glu Glu Gln
            20                  25                  30

Gln Gln Ala Leu Ser Ser Gln Met Gly Phe
        35                  40

<210> SEQ ID NO 8
<211> LENGTH: 20
<212> TYPE: PRT
<213> ORGANISM: Mycobacterium tuberculosis

<400> SEQUENCE: 8

Gln Glu Ala Gly Asn Phe Glu Arg Ile Ser Gly Asp Leu Lys Thr Gln
1               5                   10                  15

Ile Asp Gln Val
            20

<210> SEQ ID NO 9
<211> LENGTH: 16
<212> TYPE: PRT
<213> ORGANISM: Mycobacterium tuberculosis

<400> SEQUENCE: 9

Gly Asp Leu Lys Thr Gln Ile Asp Gln Val Glu Ser Thr Ala Gly Ser
1               5                   10                  15

<210> SEQ ID NO 10
<211> LENGTH: 16
<212> TYPE: PRT
<213> ORGANISM: Mycobacterium tuberculosis

<400> SEQUENCE: 10

Gly Ser Leu Gln Gly Gln Trp Arg Gly Ala Ala Gly Thr Ala Ala Ala
1               5                   10                  15

<210> SEQ ID NO 11
<211> LENGTH: 16
<212> TYPE: PRT
<213> ORGANISM: Mycobacterium tuberculosis

<400> SEQUENCE: 11

Gln Glu Ala Ala Asn Lys Gln Lys Gln Glu Leu Asp Glu Ile Ser Thr
1               5                   10                  15

<210> SEQ ID NO 12
<211> LENGTH: 28
<212> TYPE: PRT
<213> ORGANISM: Mycobacterium tuberculosis

<400> SEQUENCE: 12

Ser Thr Asn Ile Arg Gln Ala Gly Val Gln Tyr Ser Arg Ala Asp Glu
1               5                   10                  15

Glu Gln Gln Gln Ala Leu Ser Ser Gln Met Gly Phe
            20                  25

<210> SEQ ID NO 13
<211> LENGTH: 16
<212> TYPE: PRT
<213> ORGANISM: Mycobacterium tuberculosis

<400> SEQUENCE: 13

Arg Ala Asp Glu Glu Gln Gln Gln Ala Leu Ser Ser Gln Met Gly Phe
1               5                   10                  15

<210> SEQ ID NO 14
<211> LENGTH: 21
<212> TYPE: DNA
<213> ORGANISM: Mycobacterium tuberculosis

<400> SEQUENCE: 14
ctgcagcagg tgacgtcgtt g                                        21

<210> SEQ ID NO 15
<211> LENGTH: 23
<212> TYPE: DNA
<213> ORGANISM: Mycobacterium tuberculosis

<400> SEQUENCE: 15
ccgggtggcc gggaagtctg tgt                                      23

<210> SEQ ID NO 16
<211> LENGTH: 23
<212> TYPE: DNA
<213> ORGANISM: Mycobacterium tuberculosis

<400> SEQUENCE: 16
actactttct ctttctacct tcc                                      23

<210> SEQ ID NO 17
<211> LENGTH: 22
<212> TYPE: DNA
<213> ORGANISM: Artificial Sequence
<220> FEATURE:
<223> OTHER INFORMATION: PRIMER

<400> SEQUENCE: 17
gcatcgaatg catgtctcgg gt                                       22

<210> SEQ ID NO 18
<211> LENGTH: 30
<212> TYPE: DNA
<213> ORGANISM: Artificial Sequence
<220> FEATURE:
<223> OTHER INFORMATION: PRIMER

<400> SEQUENCE: 18
cccggatcct cagccaagct gaccgacctg                          30

<210> SEQ ID NO 19
<211> LENGTH: 33
<212> TYPE: DNA
<213> ORGANISM: Artificial Sequence
<220> FEATURE:
<223> OTHER INFORMATION: PRIMER

<400> SEQUENCE: 19
gccggtacca cgacggctca tcgccagttt gcc                      33

<210> SEQ ID NO 20
<211> LENGTH: 15
<212> TYPE: PRT
<213> ORGANISM: Artificial Sequence
<220> FEATURE:
<223> OTHER INFORMATION: PRIMER
<220> FEATURE:
<221> NAME/KEY: misc_feature
<222> LOCATION: (11)..(11)
<223> OTHER INFORMATION: XAA AT POSITION 11 REPRESENTS ANY AMINO ACID

<400> SEQUENCE: 20

Ala Glu Met Lys Thr Asp Ala Ala Thr Leu Xaa Gln Glu Ala Gly
1               5                   10                  15

<210> SEQ ID NO 21
<211> LENGTH: 39
<212> TYPE: DNA
<213> ORGANISM: Artificial Sequence
<220> FEATURE:
<223> OTHER INFORMATION: PRIMER

<400> SEQUENCE: 21 gggggggatcc ggtaccaggt gacgtcgttg ttcagccag               39

<210> SEQ ID NO 22
<211> LENGTH: 39
<212> TYPE: DNA
<213> ORGANISM: Artificial Sequence
<220> FEATURE:
<223> OTHER INFORMATION: PRIMER

<400> SEQUENCE: 22 gggggggtacc ggatcctcgt agtcggccgc catgacaac              39

<210> SEQ ID NO 23
<211> LENGTH: 31
<212> TYPE: DNA
<213> ORGANISM: Artificial Sequence
<220> FEATURE:
<223> OTHER INFORMATION: PRIMER

<400> SEQUENCE: 23 gggggggatcc caggtgacgt cgttgttcag c                      31

<210> SEQ ID NO 24
<211> LENGTH: 31
<212> TYPE: DNA
<213> ORGANISM: Artificial Sequence
<220> FEATURE:
<223> OTHER INFORMATION: PRIMER

<400> SEQUENCE: 24 gggggggtacc acggtgacgt cgttgttcag c                      31

<210> SEQ ID NO 25
<211> LENGTH: 32
<212> TYPE: DNA
<213> ORGANISM: Artificial Sequence
<220> FEATURE:
<223> OTHER INFORMATION: PRIMER

<400> SEQUENCE: 25 gggggtacc aacggtgacg tcgttgttca gc                                      32

<210> SEQ ID NO 26
<211> LENGTH: 31
<212> TYPE: DNA
<213> ORGANISM: Artificial Sequence
<220> FEATURE:
<223> OTHER INFORMATION: PRIMER

<400> SEQUENCE: 26 gggggtacc gggtggccgg gaagtctgtt g                                       31

<210> SEQ ID NO 27
<211> LENGTH: 31
<212> TYPE: DNA
<213> ORGANISM: Artificial Sequence
<220> FEATURE:
<223> OTHER INFORMATION: PRIMER

<400> SEQUENCE: 27 gggggatcc ctgcagcagg tgacgtcgtt g                                       31

<210> SEQ ID NO 28
<211> LENGTH: 100
<212> TYPE: PRT
<213> ORGANISM: Mycobacterium leprae

<400> SEQUENCE: 28

Met Ala Glu Met Ile Thr Glu Ala Ala Ile Leu Thr Gln Gln Ala Ala
 1               5                  10                  15

Gln Phe Asp Gln Ile Ala Ser Gly Leu Ser Gln Glu Arg Asn Phe Val
                20                  25                  30

Asp Ser Ile Gly Gln Ser Phe Gln Asn Thr Trp Glu Gly Gln Ala Ala
            35                  40                  45

Ser Ala Ala Leu Gly Ala Leu Gly Arg Phe Asp Glu Ala Met Gln Asp
        50                  55                  60

Gln Ile Arg Gln Leu Glu Ser Ile Val Asp Lys Leu Asn Arg Ser Gly
65                  70                  75                  80

Gly Asn Tyr Thr Lys Thr Asp Asp Glu Ala Asn Gln Leu Leu Ser Ser
                85                  90                  95

Lys Met Asn Phe
            100

<210> SEQ ID NO 29
<211> LENGTH: 30
<212> TYPE: DNA
<213> ORGANISM: Artificial Sequence
<220> FEATURE:
<223> OTHER INFORMATION: PRIMER

<400> SEQUENCE: 29
ccctgcaacg aacctgccgt cgactccacc                                        30

```
<210> SEQ ID NO 30
<211> LENGTH: 90
<212> TYPE: DNA
<213> ORGANISM: Mycobacterium tuberculosis

<400> SEQUENCE: 30
aagacgacga ggacgactgg gacgaagagg acgactggtg agctcccgta atgacaacag    60
acttcccggc cacccgggcc ggaagacttg                                     90

<210> SEQ ID NO 31
<211> LENGTH: 108
<212> TYPE: DNA
<213> ORGANISM: Artificial Sequence
<220> FEATURE:
<223> OTHER INFORMATION: EXPRESSION CASSETTE
<220> FEATURE:
<221> NAME/KEY: CDS
<222> LOCATION: (13)..(51)
<223> OTHER INFORMATION:

<400> SEQUENCE: 31
aggaacagat ct atg gga tcc ggt acc ctg cag cat cac cat cac cat cac    51
           Met Gly Ser Gly Thr Leu Gln His His His His His His
           1               5                  10 tagtgaaata gcgaaacacg ggatcgggcg agttcgacct tccgtcggtc tcgccct      108

<210> SEQ ID NO 32
<211> LENGTH: 13
<212> TYPE: PRT
<213> ORGANISM: Artificial Sequence
<220> FEATURE:
<223> OTHER INFORMATION: EXPRESSION CASSETTE

<400> SEQUENCE: 32

Met Gly Ser Gly Thr Leu Gln His His His His His His
1               5                  10

<210> SEQ ID NO 33
<211> LENGTH: 57
<212> TYPE: DNA
<213> ORGANISM: Artificial Sequence
<220> FEATURE:
<223> OTHER INFORMATION: MULTIPLE CLONING SITE

<400> SEQUENCE: 33
gaattcgagc tcggtacccg ggatcctct agagtcgacc tgcaggcatg caagctt        57

<210> SEQ ID NO 34
<211> LENGTH: 39
<212> TYPE: DNA
<213> ORGANISM: Artificial Sequence
<220> FEATURE:
<223> OTHER INFORMATION: PRIMER

<400> SEQUENCE: 34 gggggatcc ggtaccaggt gacgtcgttg ttcagccag                            39

<210> SEQ ID NO 35
<211> LENGTH: 55
<212> TYPE: DNA
<213> ORGANISM: Artificial Sequence
<220> FEATURE:
<223> OTHER INFORMATION: PRIMER

<400> SEQUENCE: 35 gggggatcc tcaatggtga tggtgatggt ggaagcccat ttgcgaggac agcgc          55
```

-continued

<210> SEQ ID NO 36
<211> LENGTH: 855
<212> TYPE: DNA
<213> ORGANISM: Mycobacterium tuberculosis

<400> SEQUENCE: 36
ggatccggta ccaggtgacg tcgttgttca gccaggtggg cggcaccggc ggcggcaacc 60
cagccgacga ggaagccgcg cagatgggcc tgctcggcac cagtccgctg tcgaaccatc 120
cgctggctgg tggatcaggc cccagcgcgg gcgcgggcct gctgcgcgcg gagtcgctac 180
ctggcgcagg tgggtcgttg acccgcacgc cgctgatgtc tcagctgatc gaaaagccgg 240 ttgcccctc ggtgatgccg gcggctgttg ccggatcgtc ggtgacgggt ggcgccgctc 300
cggtgggtcc gggagcgatg ggccagggtt cgcaatccgg cggctccacc agcccgggtc 360
tggtcgcgcc ggcaccgctc gcgcaggagc gtgaagaaga cgacgaggac gactgggacg 420
aagaggacga ctggtgagct cccgtaatga caacagactt cccggccacc cgggccggaa 480
gacttgccaa cattttggcg aggaaggtaa agagagaaag tagtccagca tggcagagat 540
gaagaccgat gccgctaccc tcgggcagga ggcaggtaat ttcgagcgga tctccggcga 600
cctgaaaacc cagatcgacc aggtggagtc gacggcaggt tcgttgcagg gccagtggcg 660
cggcgcggcg gggacggccg cccaggccgc ggtggtgcgc ttccaagaag cagccaataa 720
gcagaagcag gaactcgacg agatctcgac gaatattcgt caggccggcg tccaatactc 780
gagggccgac gaggagcagc agcaggcgct gtcctcgcaa atgggcttca ccatcaccat 840
caccattgag gatcc 855

<210> SEQ ID NO 37
<211> LENGTH: 1069
<212> TYPE: DNA
<213> ORGANISM: Mycobacterium tuberculosis

<400> SEQUENCE: 37
ctgcagcagg tgacgtcgtt gttcagccag gtgggcggca ccggcggcgg caacccagcc 60
gacgaggaag ccgcgcagat gggcctgctc ggcaccagtc cgctgtcgaa ccatccgctg 120
gctggtggat caggccccag cgcgggcgcg ggcctgctgc gcgcggagtc gctacctggc 180
gcaggtgggt cgttgacccg cacgccgctg atgtctcagc tgatcgaaaa gccggttgcc 240
ccctcggtga tgccggcggc tgttgccgga tcgtcggtga cgggtggcgc cgctccggtg 300
ggtccgggag cgatgggcca gggttcgcaa tccggcggct ccaccagccc gggtctggtc 360
gcgccggcac cgctcgcgca ggagcgtgaa gaagacgacg aggacgactg ggacgaagag 420
gacgactggt gagctcccgt aatgacaaca gacttcccgg ccacccgggc cggaagactt 480
gccaacattt tggcgaggaa ggtaaagaga gaaagtagtc cagcatggca gagatgaaga 540
ccgatgccgc taccctcggg caggaggcag gtaatttcga gcggatctcc ggcgacctga 600
aaacccagat cgaccaggtg gagtcgacgg caggttcgtt gcagggccag tggcgcggcg 660
cggcggggac ggccgcccag gccgcggtgg tgcgcttcca agaagcagcc aataagcaga 720
agcaggaact cgacgagatc tcgacgaata ttcgtcaggc cggcgtccaa tactcgaggg 780
ccgacgagga gcagcagcag gcgctgtcct cgcaaatggg cttctgaccc gctaatacga 840
aaagaaacgg agcaaaaaca tgacagagca gcagtggaat ttcgcgggta tcgaggccgc 900
ggcaagcgca atccagggaa atgtcacgtc cattcattcc ctccttgacg aggggaagca 960

-continued

```
gtccctgacc aagctcgcag cggcctgggg cggtagcgt tcggaggcgt accagggtgt    1020
ccagcaaaaa tgggacggcc acggctaccg agctgaacaa gcgctgcag              1069
```

<210> SEQ ID NO 38
<211> LENGTH: 1282
<212> TYPE: DNA
<213> ORGANISM: Mycobacterium tuberculosis

<400> SEQUENCE: 38

```
ggtaccaggt gacgtcgttg ttcagccagg tgggcggcac cggcggcggc aacccagccg     60
acgaggaagc cgcgcagatg ggcctgctcg gcaccagtcc gctgtcgaac catccgctgg    120
ctggtggatc aggccccagc gcgggcgcgg gcctgctgcg cgcggagtcg ctacctggcg    180
caggtgggtc gttgacccgc acgccgctga tgtctcagct gatcgaaaag ccggttgccc    240
cctcggtgat gccggcggct gttgccggat cgtcggtgac gggtggcgcc gctccggtgg    300
gtccgggagc gatgggccag ggttcgcaat ccggcggctc caccagcccg ggtctggtcg    360
cgccggcacc gctcgcgcag gagcgtgaag aagacgacga ggacgactgg gacgaagagg    420
acgactggtg agctcccgta atgacaacag acttcccggc cacccgggcc ggaagacttg    480
ccaacatttt ggcgaggaag gtaaagagag aaagtagtcc agcatggcag agatgaagac    540
cgatgccgct accctcgggc aggaggcagg taatttcgag cggatctccg gcgacctgaa    600
aacccagatc gaccaggtgg agtcgacggc aggttcgttg cagggccagt ggcgcggcgc    660
ggcggggacg gccgcccagg ccgcggtggt gcgcttccaa gaagcagcca ataagcagaa    720
gcaggaactc gacgagatct cgacgaatat tcgtcaggcc ggcgtccaat actcgagggc    780
cgacgaggag cagcagcagg cgctgtcctc gcaaatgggc ttctgacccg ctaatacgaa    840
aagaaacgga gcaaaaacat gacagagcag cagtggaatt tcgcgggtat cgaggccgcg    900
gcaagcgcaa tccagggaaa tgtcacgtcc attcattccc tccttgacga ggggaagcag    960
tccctgacca agctcgcagc ggcctgggc ggtagcggtt cggaggcgta ccagggtgtc   1020
cagcaaaaat gggacgccac ggctaccgag ctgaacaacg cgctgcagaa cctgcgcgg   1080 acgatcagcg aagccggtca ggcaatggct tcgaccgaag gcaacgtcac tgggatgttc   1140
gcatagggca acgccgagtt cgcgtagaat agcgaaacac gggatcgggc gagttcgacc   1200
ttccgtcggt ctcgcccttt ctcgtgttta tacgtttgag cgcactctga gaggttgtca   1260
tggcggccga ctacgaggat cc                                           1282
```

<210> SEQ ID NO 39
<211> LENGTH: 229
<212> TYPE: DNA
<213> ORGANISM: Artificial Sequence
<220> FEATURE:
<223> OTHER INFORMATION: multiple cloning site-artificial DNA

<400> SEQUENCE: 39

```
ggaaacagct atgaccatga ttacgccaag cgcgcaatta accctcacta aagggaacaa     60
aagctgggta ccgggccccc cctcgaggtc gacggtatcg ataagcttga tatcgaattc    120
ctgcagcccg ggggatccac tagttctaga gcggccgcca ccgcggtgga gctccaattc    180
gccctatagt gagtcgtatt acgcgcgctc actggccgtc gttttacaa               229
```

US 6,436,409 B1

POLYNUCLEOTIDE FUNCTIONALLY CODING FOR THE LHP PROTEIN FROM *MYCOBACTERIUM TUBERCULOSIS*, ITS BIOLOGICALLY ACTIVE DERIVATIVE FRAGMENTS, AS WELL AS METHODS USING THE SAME

This application is a regular National application claiming priority from Provisional Application, U.S. Application Ser. No. 60/052,631 filed Jul. 16, 1997 now abandoned. The entire disclosure of this application is incorporated herein-by-reference.

BACKGROUND OF THE INVENTION

1. Field of the Invention

The present invention is directed to a polynucleotide comprising an open reading frame coding for a polypeptide from *Mycobacterium tuberculosis*, named LHP capable of inducing an immune response in a host. lhp is placed under the control of its own regulation signals which are functional in mycobacteria, especially in mycobacteria belonging to the *Mycobacterium tuberculosis* complex and also in fast growing mycobacteria such as *Mycobacterium smegmatis* and also in *E. coli*. The *Mycobacterium tuberculosis* complex has its usual meaning, i.e. the complex of mycobacteria causing tuberculosis which are *Mycobacterium tuberculosis*, *Mycobacterium bovis*, *Mycobacterium africanum*, *Mycobacterium microti* and the vaccine strain *M. bovis* BCG.

The invention is also directed to the polypeptide LHP encoded by lhp and most preferably to suitable antigenic portions of LHP as well as to oligomeric polypeptides containing more than one unit of LHP or an antigenic portion of LHP. The invention concerns also immunogenic and vaccine compositions containing a polypeptide or an oligomeric polypeptide such as defined above or live recombinant attenuated mycobacteria transformed with a polynucleotide according to the present invention. The invention also concerns antibodies directed specifically against such polypeptides that are useful as diagnostic reagents. In another embodiment, the present invention is directed to a polynucleotide carrying the natural regulation signals of lhp which is useful in order to express heterologous proteins in mycobacteria as well as functionally active regulatory polynucleotides derived from said regulatory region. Finally, the present invention is directed to oligonucleotides comprising at least 12 consecutive nucleotides which are useful as reagents for detecting the presence of *Mycobacterium tuberculosis* in a biological sample.

2. Related Prior Art

*Mycobacterium tuberculosis* and *M. bovis* cause tuberculosis, a disease which currently kills three million people each year. The virulence of pathogenic mycobacteria is associated with their ability to parasitize and survive within phagocytic cells. Little is known about mechanisms governing gene expression during the intracellular growth stage. This issue is of prime importance as the intracellular stage of pathogenic mycobacteria can be viewed as an adaptative process, involving transcriptional regulatory mechanisms. Mycobacterial genes affecting intracellular growth and virulence are being actively sought (Collins, 1996; Collins, 1995, Quinn, 1996). Using subtractive genomic hybridization between virulent *M. bovis* and the attenuated vaccine strain *M. bovis* BCG, Maheiras et al. (Maheiras et al., 1996) identified three regions of difference (RD1 to RD3). RD1 was detected in all strains of *M. tuberculosis* and *M. bovis* tested but is absent in all BCG substrains, suggesting that it may be an important determinant of virulence.

The or flC gene, encoding the early secreted antigenic target 6 kDa (ESAT-6) lies within RD1. The ESAT-6 protein is a major T-cell antigen which has been purified from *M. tuberculosis* short-term culture filtrates (Harboe et al., 1996; Sorensen et al., 1995). Purified ESAT-6 stimulates the production of gamma interferon from mice memory immune T lymphocytes and may contribute to the development of antituberculous immunity (Andersen et al., 1995; and U.S. Patent Application filed on Jun. 5, 1995).

The Mycobacterium genus encompasses more than 70 recognized bacterial species including *M. tuberculosis* and *M. leprae*, the agents of tuberculosis and leprosy respectively. The development of effective prophylactic vaccine and specific diagnostic reagents is a priority to control the extension of mycobacterial infections. In that context, mycobacterial protein antigens are extensively screened upon their ability to induce B- and T-cell reactivity. Obtaining purified proteins from slow growing pathogenic mycobacteria is labor-intensive and requires important containment facilities. Alternatively, many immunological studies of mycobacterial antigens have been conducted with *E. coli*—expressed recombinant molecules. However, problems related to lipopolysaccharide (LPS) contamination are frequently encountered. Moreover, post-translational modifications such as proteolytic processing, intern removal, lipid acylation and glycosylation of proteins have been reported to occur in mycobacteria. Such modification cannot be mimicked in *E. coli* and may influence dramatically the stability, antigenicity and the immunogenicity of the peptide chain. Thus, it was recently postulated that site-specific mannosylation protects the *M. tuberculosis* 19 kDa lipoprotein antigen against proteolysis (Hermann. et al., 1996). Accordingly, there is a great need in the art of suitable protein expression systems allowing the preparation of mycobacterial immunogenic polypeptides that are useful for diagnostic and vaccine purposes.

SUMMARY OF THE INVENTION

Now, the inventors have discovered a polynucleotide carrying the regulatory expression signals of the ESAT-6 protein as well as an open reading frame coding for a new antigenic protein from *Mycobacterium tuberculosis* that they have named LHP.

The LHP polypeptide of the invention shares a great similarity with a *Mycobacterium tuberculosis* peptide described in the PCT Application No. WO 97/09429 or in the PCT Application No. WO 97/09428 (Corixa Corporation) a partial sequence of which is disclosed in those patent applications.

The present inventors have characterized the portions of the polynucleotide according to the invention that are functional in mycobacteria in order to allow the expression of LHP, as well as the expression of an heterologous polypeptide that is placed under the control of said regulatory region contained in the polynucleotide according to the present invention.

More specifically, the inventors have located the transcription initiation sites of the lhp/or flC operon using *M. tuberculosis* RNA and have precisely mapped the portions of the regulatory region of the lhp/or flC operon that are functional in bacteria in general, being functionally active in *E. coli* as well as in mycobacteria. Further, the inventors have mapped the portions of the polynucleotide according to the present invention that are functionally active in slow growing mycobacteria, such as bacteria belonging to the *Mycobacterium tuberculosis* complex, and in fast-growing mycobacteria, such as *M. smegmatis*.

Further, the present inventors have used the functionally active portions of the regulatory region of the lhp/or flC operon for expressing a polypeptide heterologous with respect to said regulatory region.

In a specific embodiment, the present inventors have constructed a mycobacterial expression vector allowing production of recombinant proteins tagged by a stretch of six histidine. Such vector enables production of virtually any polypeptide in a mycobacterial context and allows easy purification of native proteins by immobilized metal affinity chromatography. Additionally, the availability of monoclonal antibody directed against the (His)6 polypeptide facilitates the detection of proteins for which no specific immune reagent are available. This system is very useful for biochemical and immunological characterization of mycobacterial proteins.

Accordingly, given its high level and constitutive expression of the regulatory polynucleotide according to the present invention in mycobacteria, said promoter is used to construct a novel mycobacterial expression/purification system.

This vector, designated pIPX30, allows versatile gene fusions to produce histidine-tagged proteins in mycobacteria. Additionally, the high affinity of polyhistidine for immobilized metal ions enables one-step chromatographic isolation of native, histidine-tagged polypeptides. As a validation of the system, the inventors have performed the expression of recombinant DES(Histidine)$_6$ *M. tuberculosis* protein antigen and its immunodetection from *M. smegmatis* cultures.

Thus, the present invention is directed to a polynucleotide comprising a functional portion of the regulatory region of the lhp operon and to its use in a recombinant expression vector carrying a polynucleotide encoding a polypeptide of interest.

The invention also concerns recombinant expression vectors containing a polynucleotide according to the invention, and more specifically a polynucleotide carrying one of the regulatory polynucleotides characterized by the inventors.

The invention is also directed to recombinant cell hosts containing a polynucleotide or a recombinant vector as defined above.

In another embodiment, an aspect of the present invention is the entire LHP antigenic polypeptide as well as particular antigenic portions of the LHP polypeptide that have been identified by the inventors.

A further embodiment of the present invention is directed to oligomeric polypeptides that contain at least one unit of an antigenic portion of the LHP polypeptide, that are useful as immunogenic molecules. Consequently, the present invention concerns also immunogenic compositions as well as vaccine compositions that are useful to diagnose and to prevent an infection by mycobacteria belonging to the *M. tuberculosis* complex, and more specifically by *Mycobacterium tuberculosis* in humans and animals.

Another object of the present invention is a polyclonal or a monoclonal antibody directed specifically against the LHP polypeptide or an antigenic portion thereof.

The present invention concerns also methods and corresponding kits containing either a polynucleotide, polypeptide or an antibody according to the invention in order to perform a diagnosis of infection with *Mycobacterium tuberculosis* in a biological sample.

Finally, the invention pertains to immunogenic and vaccine compositions containing at least a polypeptide or a recombinant cell host expressing the LHP polypeptide, preferably in combination with the ESAT-6 antigenic protein and also to vaccine compositions containing live non pathogenic recombinant cell hosts expressing these polypeptides.

When plasmid pIPX26 is transferred in *M. smegmatis* I and *M. bovis*-BCG, the ESAT-6 protein, which is normally absent from these mycobacterial strains is expressed.

This ESAT-6 heterologous expression is detected by Western blot with the monoclonal antibody Hyb 76-8 on protein extracts.

The sequence of the DNA insert of pIPX 26 is present in SEQ ID NO:38 Annex II.

Figure 2:
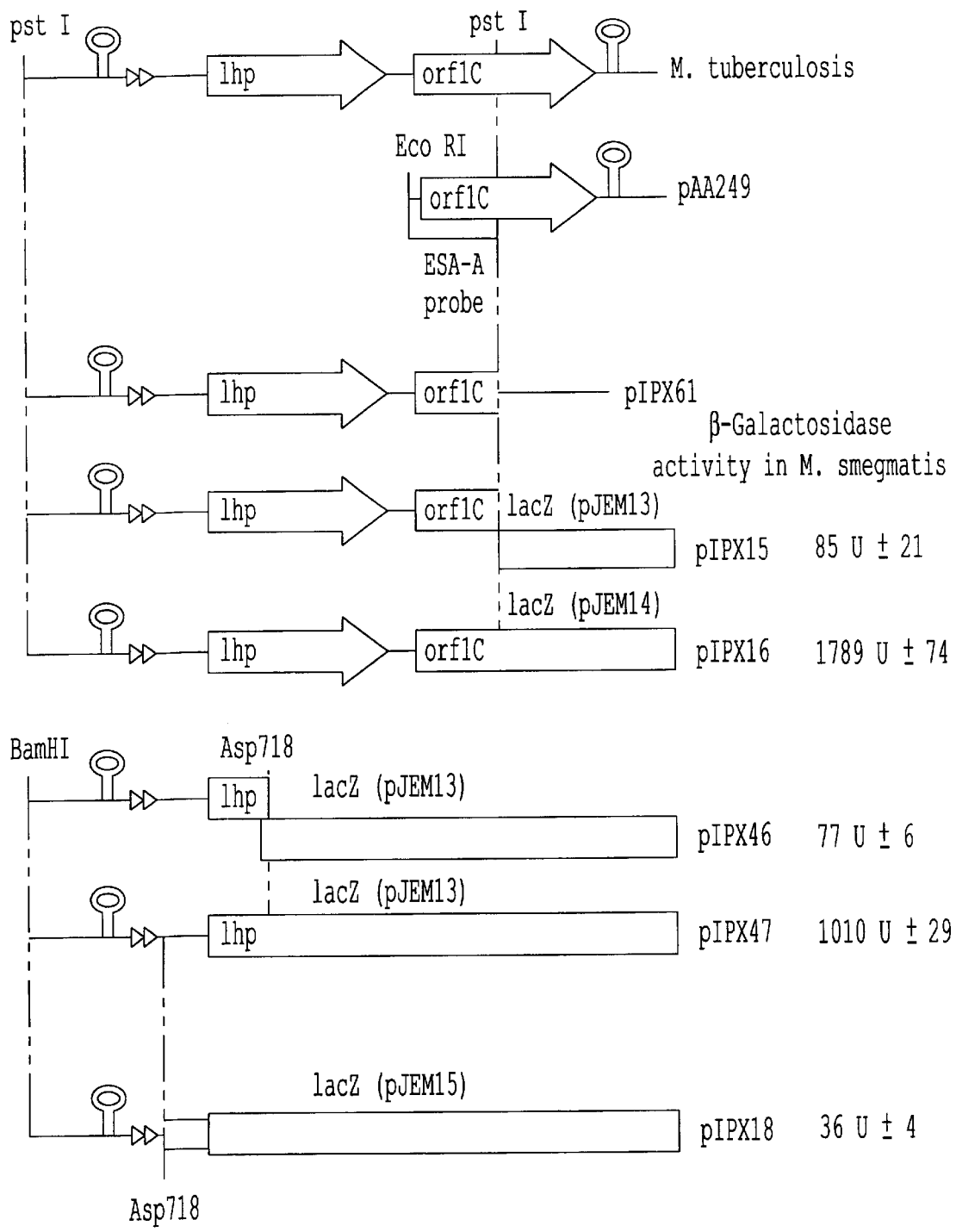

FIG. 2—Gene arrangement upstream from the *M. tuberculosis* or flC gene and lacZ gene fusions used in this study. The 1.1 kb PstI fragment from pAA249 was blunted with T4 DNA polymerase in the conditions described by the supplier (New England Biolabs, Mass. USA). Insert of this DNA fragment into T4-blunted, SnaBI-digested pJEM13 and pJEM14 resulted in pIPX15 and pIPX16 respectively. Oligonucleotide pairs OF1 (5'-GGGGGGATCCCAGGT GACGTCGT TGTTCAGC-3')(SEQ ID NO:23) and OB1 (5'-GGGGGGTACCACGGTGACGTCGTTGTTCAGC-3'),(SEQ ID NO:24) OF1 and OB2 (5'-GGGGGG TACCAACGGTGACGTCGTTGTTCAGC-3')(SEQ ID NO:25) together with PE-1 (5'-GGGGGGTACC GGGTGGCCGGGAAGTCTGTTG-3')(SEQ ID NO:26) and PE-4 (5'-GGGGGGATCCCTGCAGCAGGTG ACGTCGTTG-3')(SEQ ID NO:27) were used for PCR amplification from pIPX61. Plasmids pIPX45, pIPX46 and pIPX18 were obtained by insertion of BamHI/Asp718-digested PCR fragments into the corresponding sites in pJEM13 and pJEM15. Stem/loops represent probable transcription terminators and open triangles indicate 18 bp tandem repeats upstream from lhp. Results of §-galactosidase assays and means and standard deviations of three measurements and were determined in *M. smegmatis* as described in (Timm et al., 1994).

Figure 3A:
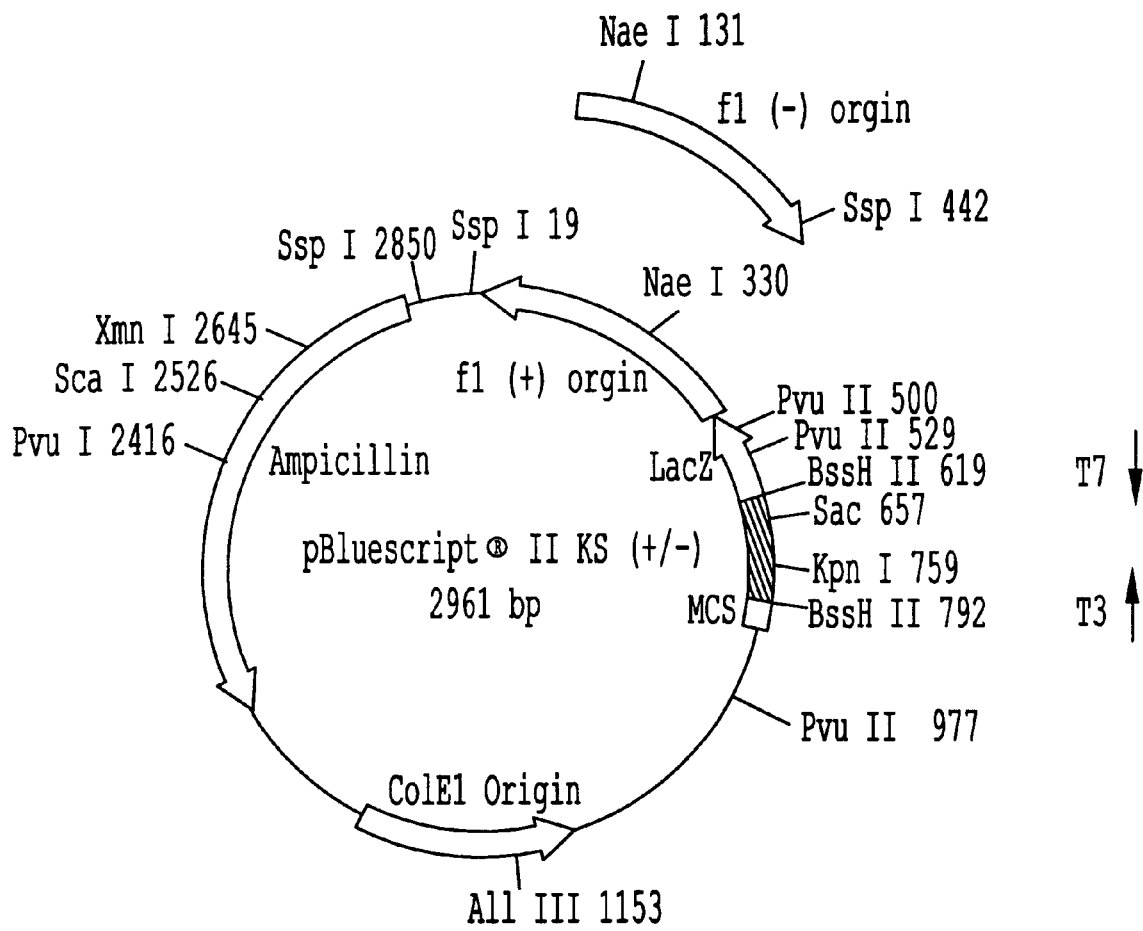
Figure 3B:
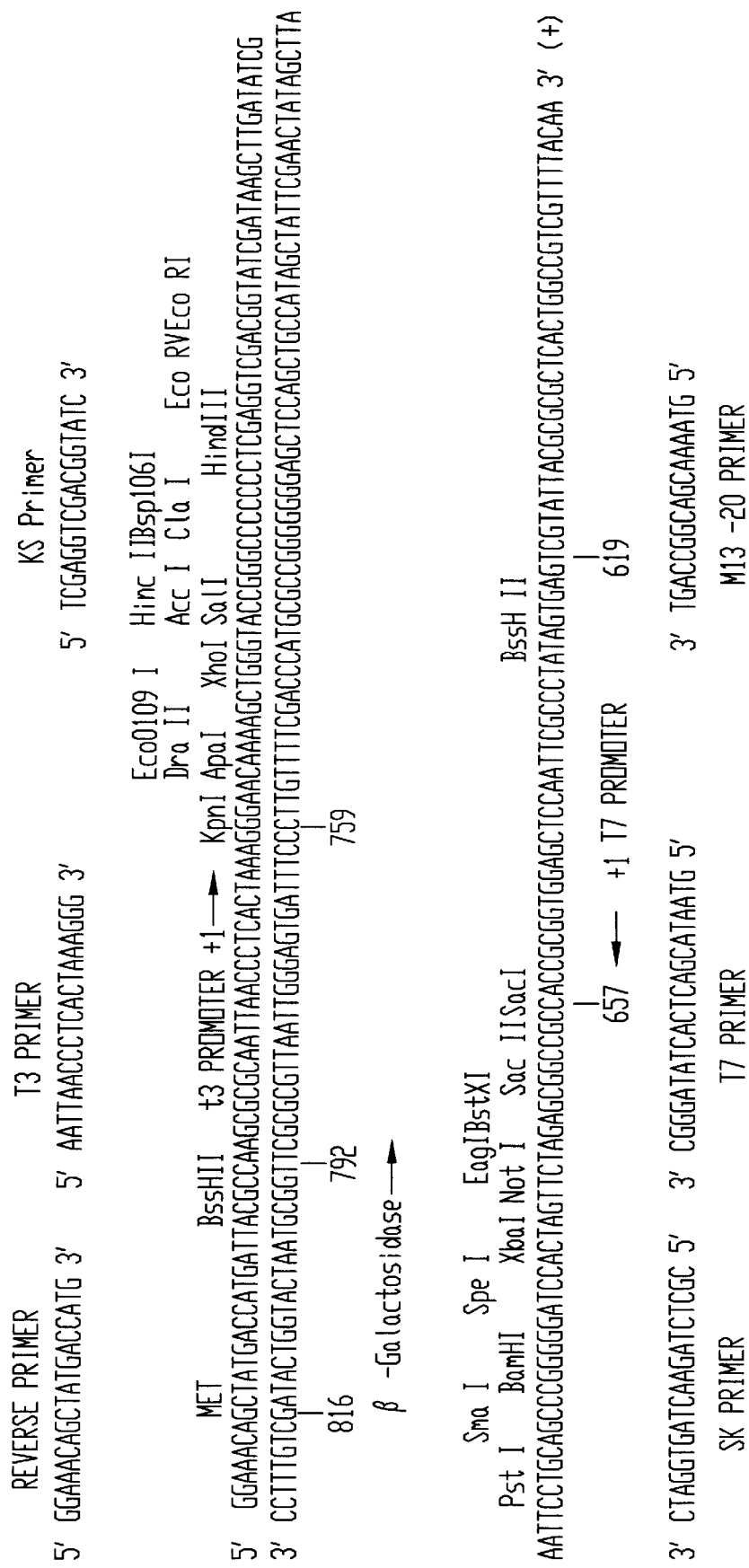

FIG. 3—Map of plasmid pBluescript 11 KS (+/−) phagemid used to construct plasmid pIPX61; shown at the bottom of the figure is SEQ ID NO:39, the complement of nucleotides 1–115 of SEQ ID NO:39, the Reverse primer (nucleotides 1–19 of SEQ ID NO:39, the T3 primer (the complementary sequence of nucleotides 38–55 of SEQ ID NO:39, the KS primer (nucleotides 98–115 of SEQ ID NO:39, the SK primer (the complementary sequence of nucleotides 134–152 of SEQ ID NO:39, the T7 primer (the complementary sequence of nucleotides 181–202 of SEQ ID NO:39), and the M13-20 primer (the complementary sequence of nucleotides 213–227 of SEQ ID NO:39).

Figure 4:
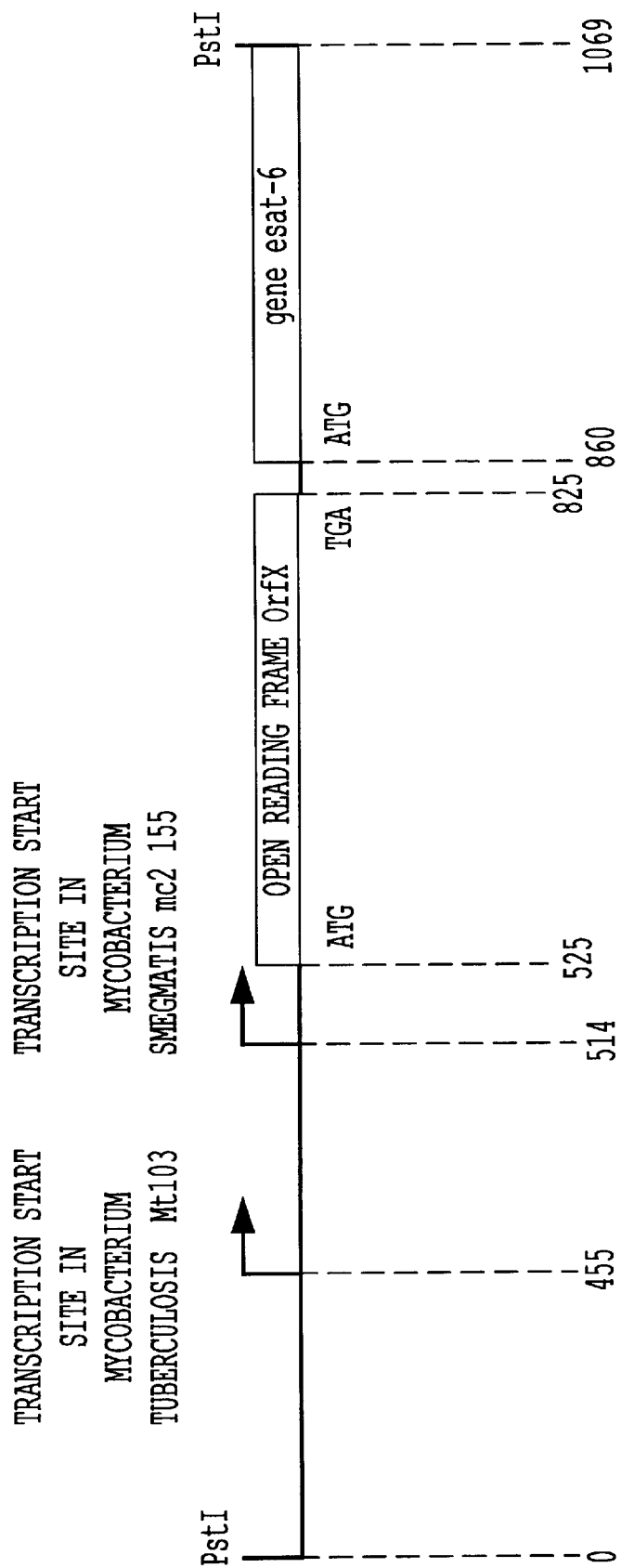

FIG. 4—Main features of the nucleotide insert contained in plasmid pIPX61 that has been deposited at the CNCM on May 14, 1996 under the Accession Number I-1705.

FIG. 5—Nucleotide and amino acids sequence features upstream from the *M. tuberculosis* or flC start codon. (A) nucleotide sequence (nucleotides 1–768 of SEQ ID NO:21) and deduced amino acid sequence (SEQ ID NO:5) of lhp. A potential ribosome binding site (RBS) upstream from the predicted start codon is underlined. Transcriptional start sites identified in *M. tuberculosis* (+1 Mtb) and in *M. smegmatis* (+1 Ms) are indicated by triangles. (B) peptide sequence similarity between the predicted *M. tuberculosis* lhp gene (SEQ ID NO:5) product and the *M. leprae* L45 seroreactive protein antigen (SEQ ID NO:28) (Accession Number X90946).

FIG. 6—mapping of the lhp-or flC promoter activity. (A) primer extension mapping of the transcriptional start sites (T1, T2 and T3) in *M. tuberculosis*. Reverse transcription was performed as described in (Berthet et al., 1995) using the E64 oligonucleotide (5'-CCCTGCAACGAACCTG CCGTCGACTCCACC-3')(SEQ ID NO:29) with (lane 1) or without (lane 2) RNA. The DNA ladder was generated by sequencing pIPX61 with E64 using the T7 sequencing kit (Pharmacia Biotech). (B) structural features of the *M. tuberculosis* or flC promoter (SEQ ID NO:30). (C) primer extension mapping of the transcriptional start sites (S1 and S2) in *M smegmatis* transformed with pIPX16. Experimental conditions were the same as described in (A).

Figure 7A:
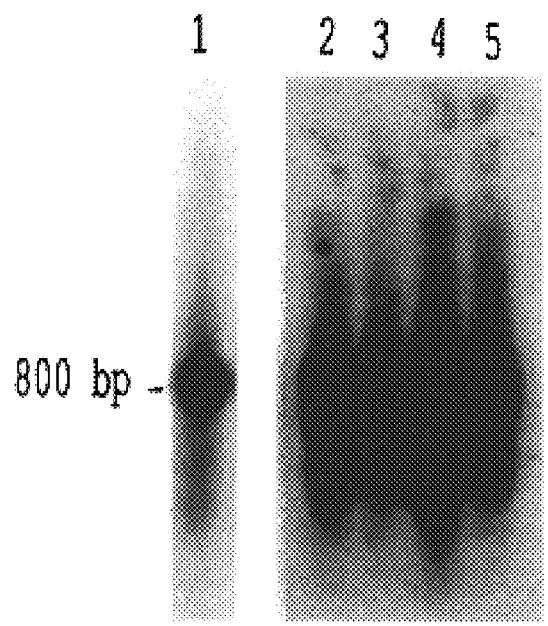
Figure 7B:
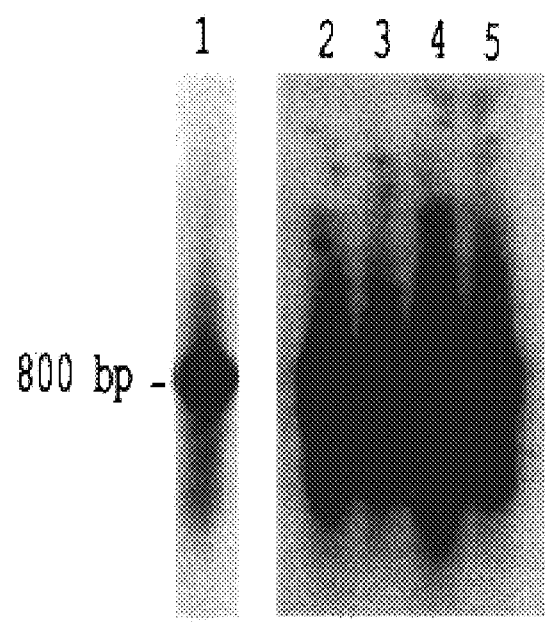

FIG. 7—Analysis of the lhp/or flC messenger RNA transcript. Total RNA was extracted from *M. tuberculosis* broth cultures on day 5 (lane 1 and 2), day 9 (lane 3), day 13 (lane 4) and day 16 (lane 5). Total RNA (5 µg) was separated on 1% agarose gel supplemented with formamide/ formaldehyde and processed for Northern blotting as described in (Sambrook et al., 1989). Hybridization was carried out using the radiolabeled ESA-A probe (See FIG. 2). Autoradiography was performed for 4 (lane 1) to 24 hours (lane 2 to 5).

Figure 8:
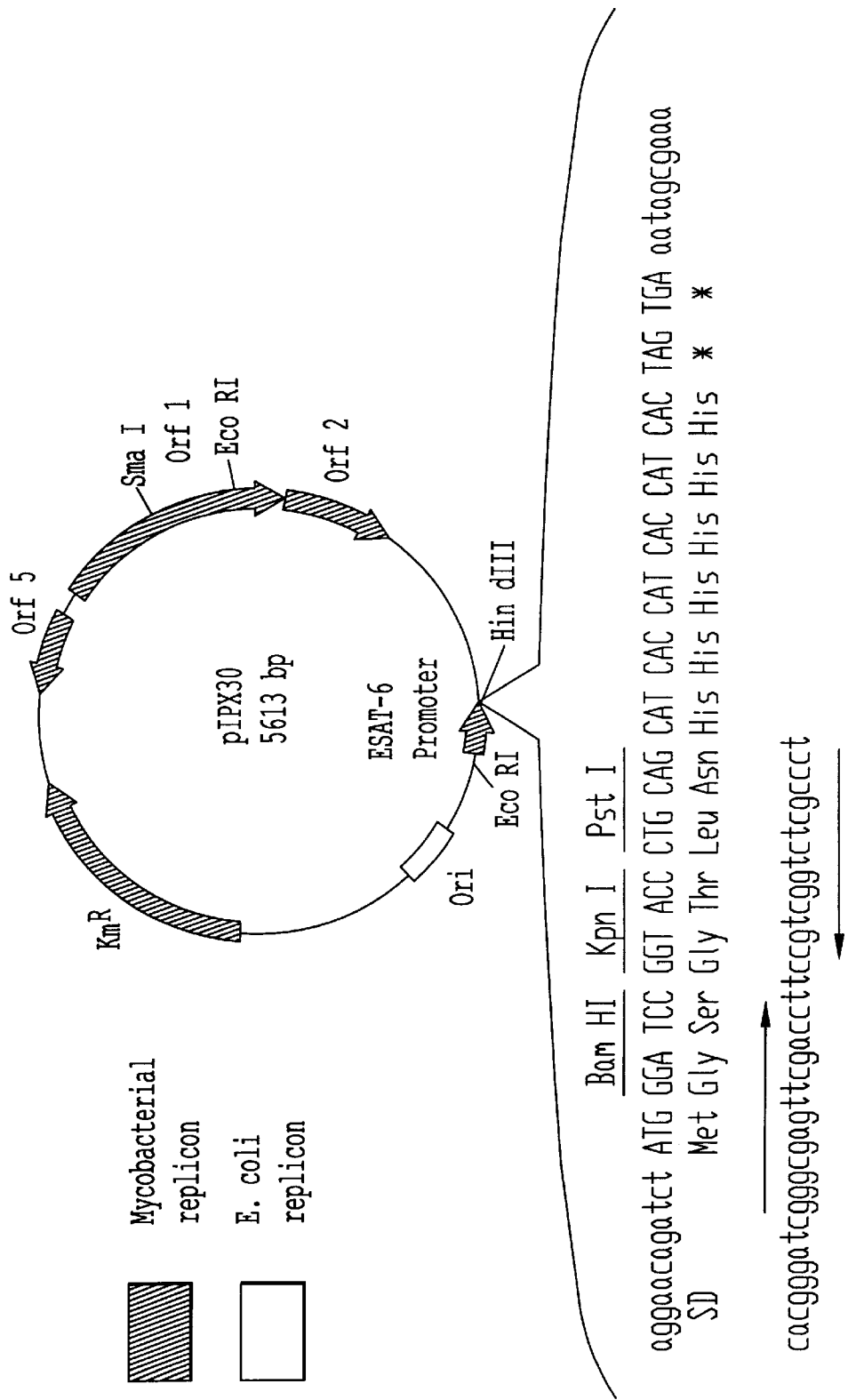

FIG. 8—Features of the pIPX30 expression/tagging plasmid. Plasmid pIPX30 is derived from plasmid pPV24 and is a shuttle plasmid possessing the following features: (1) the origin of replication of pAL5000 for propagation in mycobacteria, the origin of replication from vector pUC19 allowing its propagation in *E. coli,* the aph selection gene conferring resistance to kanamycin; (2) the promoter region of lhp and ESAT-6 from *M. tuberculosis,* functionally active in slow growing (*M. Tuberculosis, M. bovis*-BCG, etc.) and in fast growing mycobacteria (*M. Smegmatis*); (3) an expression cassette consisting in: Shine-Dalgarno site/ATG from plasmid pJEM15, three cloning sites (BamHI, KpnI, PstI), a DNA fragment coding for six Histidine, two translation stop codons and the transcription terminator form ESAT-6 (SEQ ID NO:31,32).

Plasmid pIPX30 has been constructed by digestion of plasmid pPV24 with KpnI/PstI, then treated by phage T4 DNA polymerase and then by insertion of an expression cassette having blunt-ended at 5' and 3' ends.

Plasmid pIPX30 allows the production of proteins having a six Histidine stretch on their NH2 extremity. This feature facilitates their purification by affinity chromatography on columns endowed with immobilized metal ions (IMAC).

Figure 9:
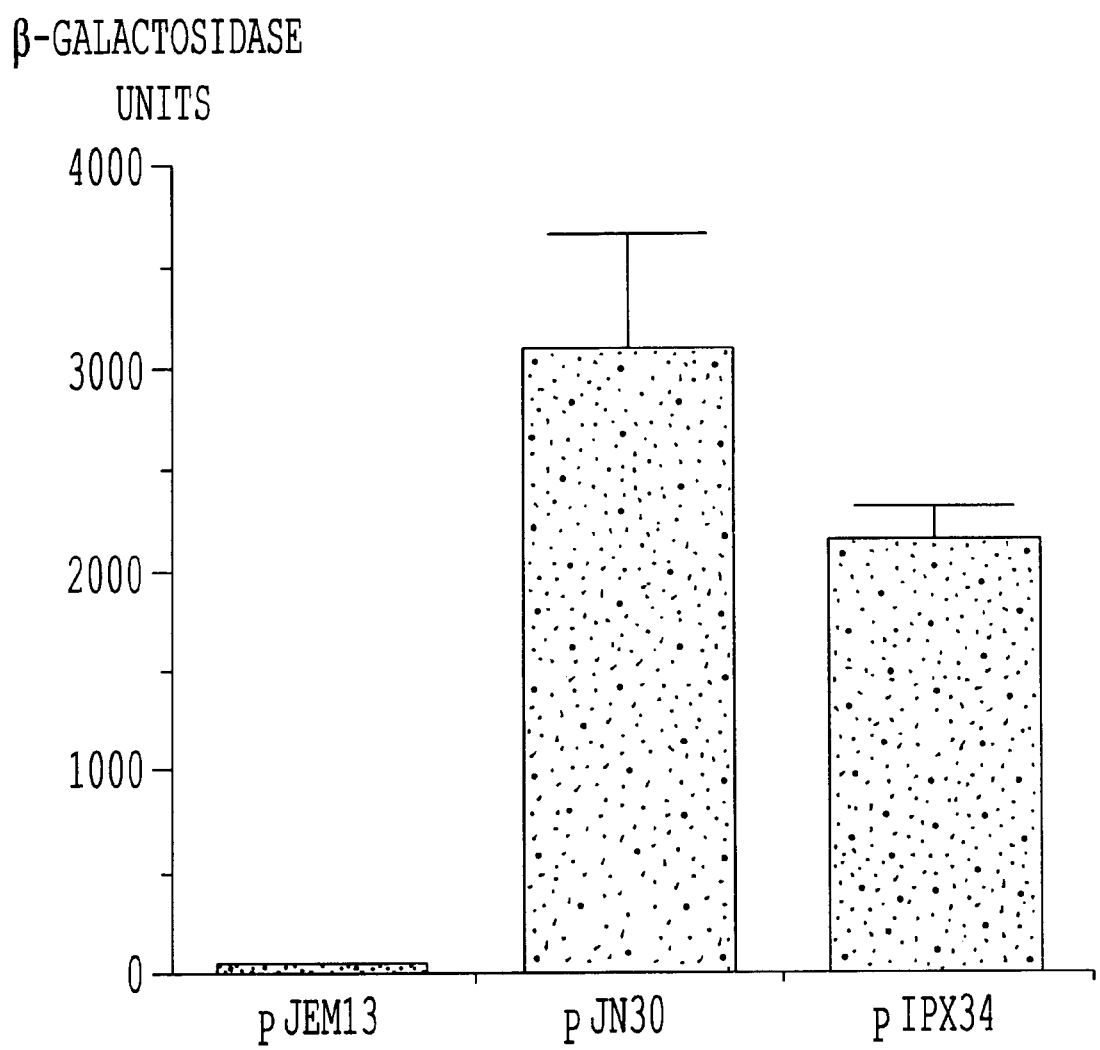

FIG. 9—Beta-galactosidase activities of *M. smegmatis* clones containing pIPX34 or positive (pJN30) and negative (pJEM13) control vectors.

Figure 10A:
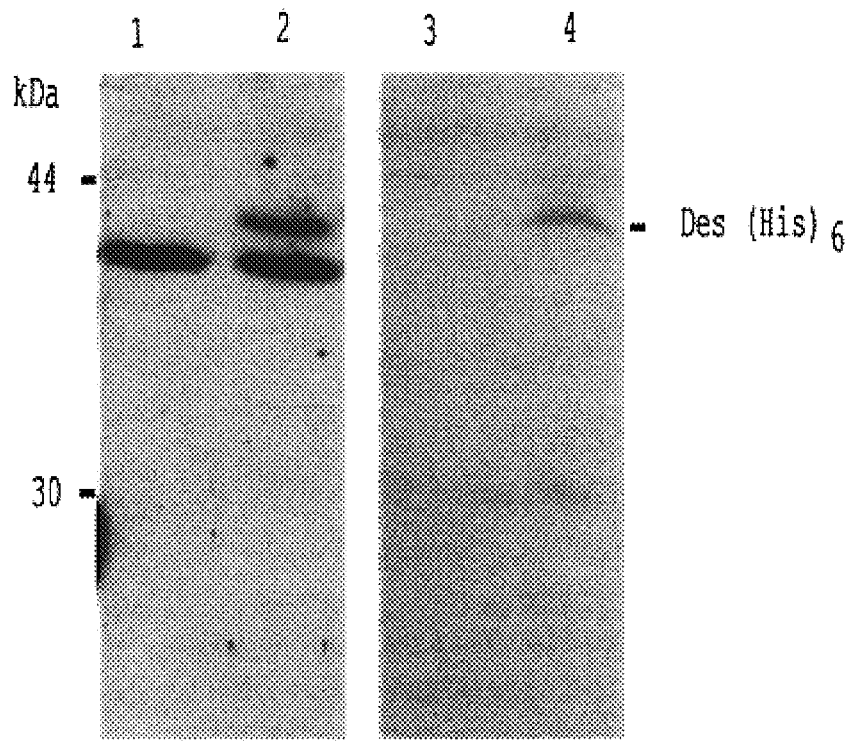
Figure 10B:
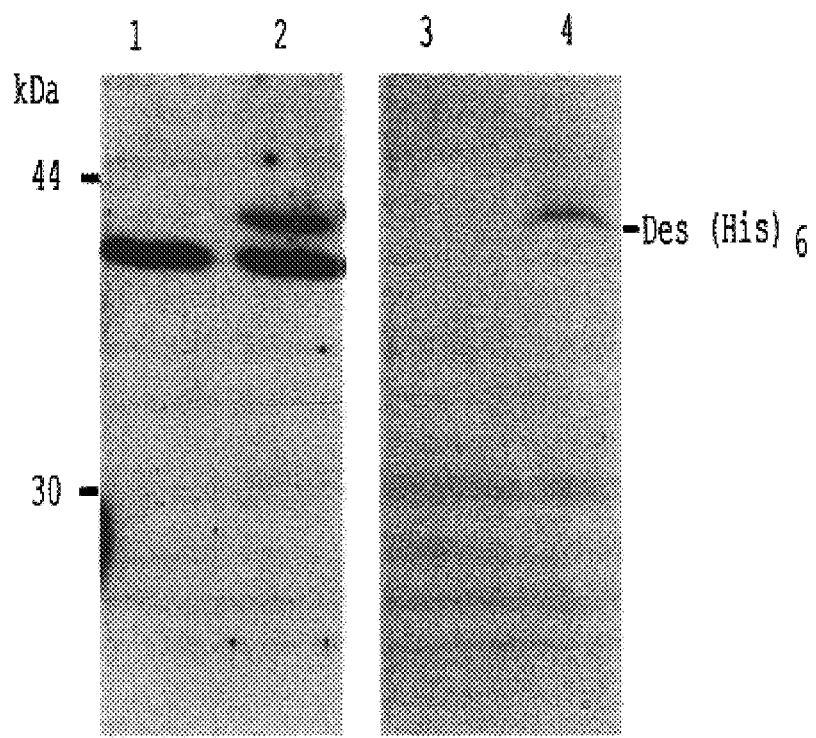

FIG. 10—Immunodetection of DES-(His)6 in *Mycobacterium smegmatis* protein extracts.

Lanes 1–2: revelation with an anti-DES polyclonal antiserum. Lanes 3–4: revelation with a monoclonal antibody directed against X(His)6.

Lanes 1 and 3: mc2 155 w+(wild type)

Lanes 2 and 4: mc2 155 [pIPX30-DES]

Figure 11:
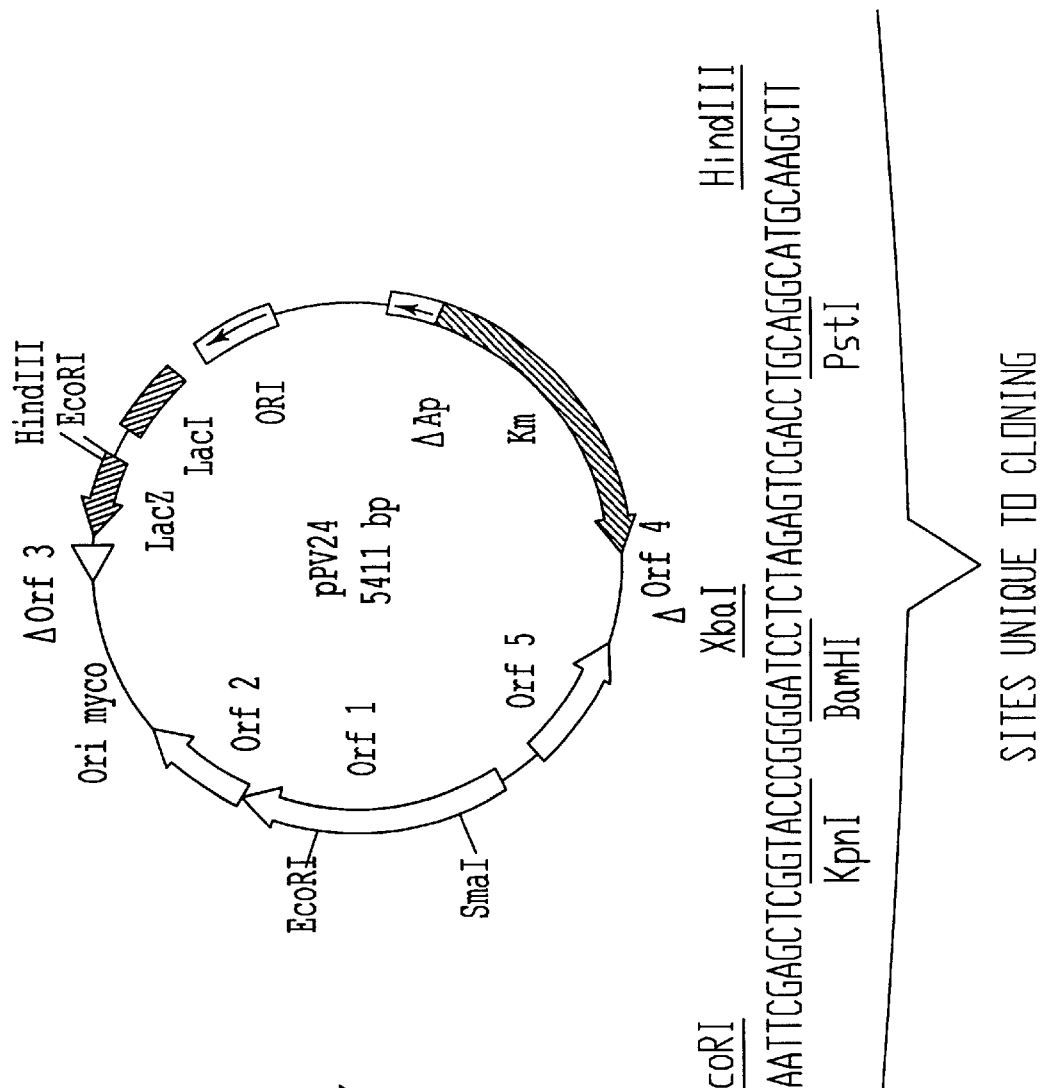

FIG. 11—Map of plasmid pPV24. PPV24 is a shuttle plasmid (*E. Coli*—mycobacteria). This plasmid has been constructed in two steps: (a) a large portion of the ampiciline resistance coding gene as well as the neighboring non-useful sequences of plasmid pUC 18 (NdeI+BsaI fragment) have been replaced by the kanamycin resistance gene from pUC4K (PstI fragment) which also express in mycobacteria. The resulting vector is pPV8 (2.8 kb); (b) the minimal origin of replication of the mycobacterial plasmid pAL500 (EcoRV+HpaI fragment) has been cloned at the StuI site from pPV8. The final vector is pPV24 (5.4 kb), which carries the multiple cloning site (SEQ ID NO:33) from pUC18 and allows the direct detection of recombinant host cells on culture medium supplemented with X-Gal.

Figure 12:
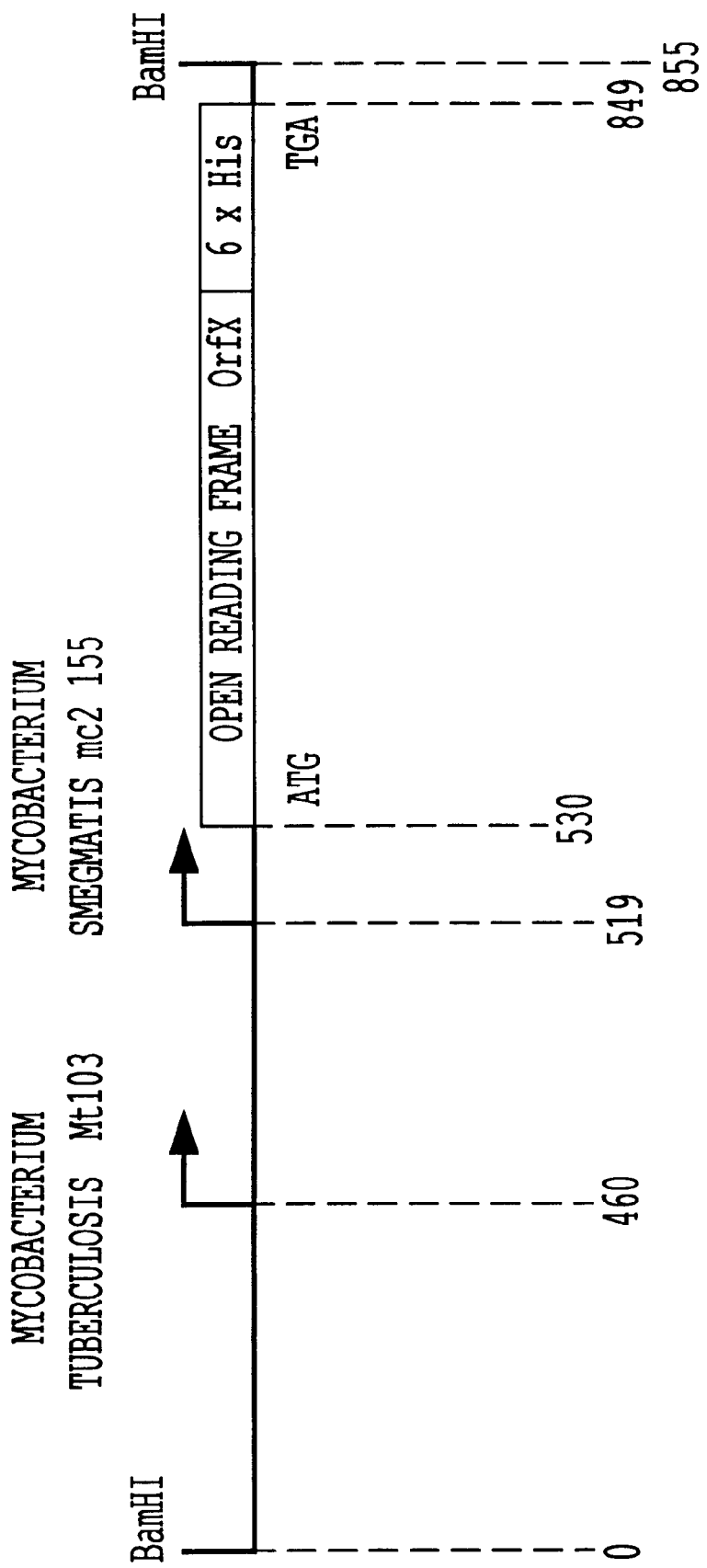

FIG. 12—pPX1 is a shuttle cloning vector (*E. Coli*—mycobacteria) of the pPV24 kind, which confers kanamycin resistance and possessing a 855 bp insert at the BamHI unique cloning site. The 855 bp insert from *Mycobacterium tuberculosis* H37 Rv is generated by PCR amplification using the following primer pair:
ESB-1 (5'-GGGGGGATCCGGTACCAGGTGACGTCGTT GTTCAGCCAG-3')(SEQ ID NO:34) PO-1 (5'-GG GGG-GATCCTCAATGGTGATGGTGATGGTGGAAG CCCATTTGCGAGGACAGCGC-3')(SEQ ID NO:35)
and then by digestion with the restriction enzyme BamHI. This DNA fragment contains the open reading frame referenced or fX (which is the lhp gene) fused to a DNA stretch coding for six Histidine. This DNA fragment carries a promoter region and transcription start sites, allowing gene expression in *Mycobacterium smegmatis* and *Mycobacterium bovis*-BCG and *Mycobacterium tuberculosis.*

Figure 13:
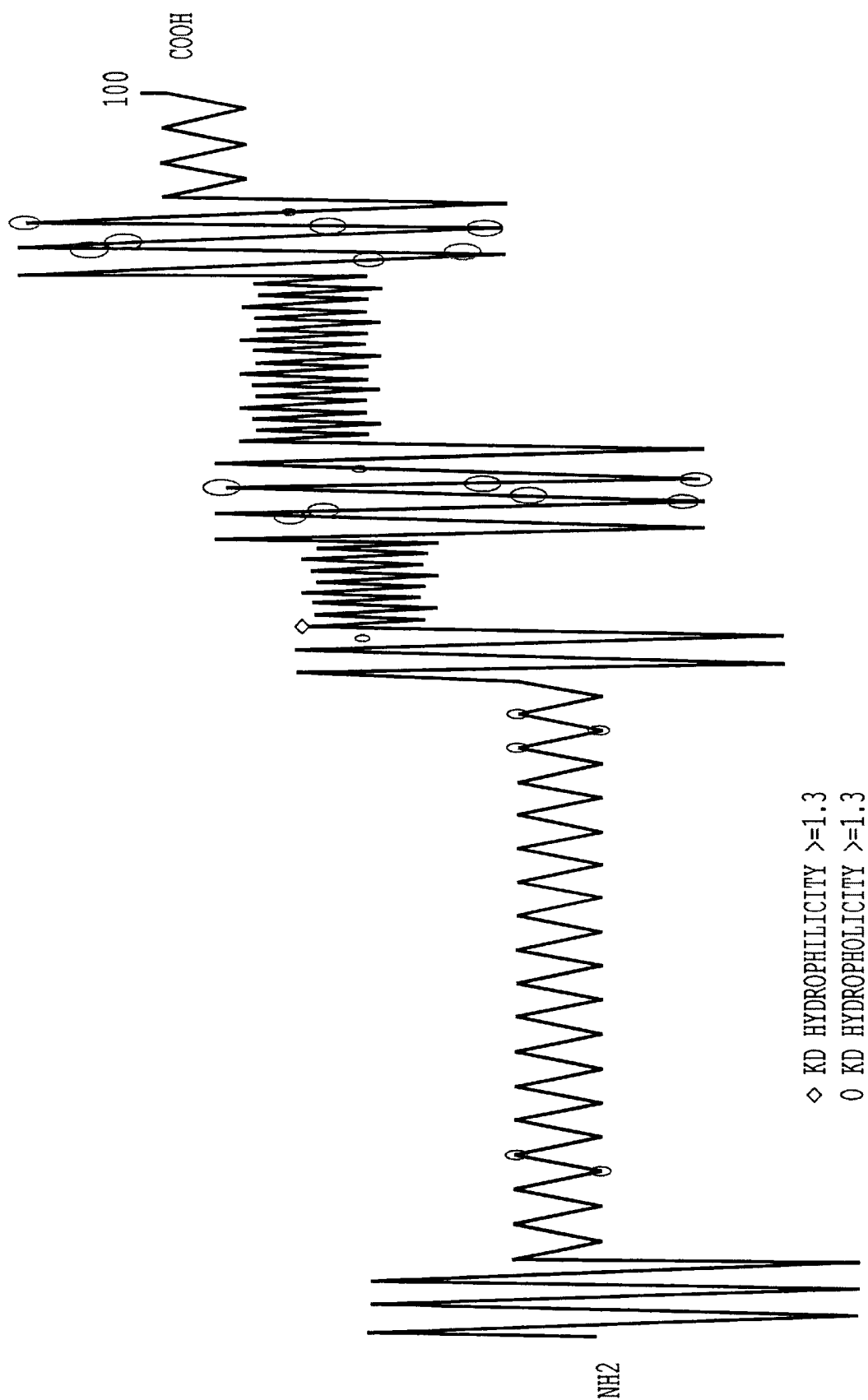

FIG. 13—Predictive analysis of the conformational features and of the hydophilicity/hydrophobicity pattern of the LHP polypeptide (Kyte an Doolitlle, hydrophathy [1982] and Goldman et al., transbilayer helices [1986]). Each point represents one amino acid of the LHP sequence. Long vertical stretches represent alpha helix conformation and short vertical stretches represent beta-turns. Circles represent they hydrophilicity index of a particular amino acid, taking into account of the hydrophilicity/hydrophobicity of the neighboring amino acids.

Figure 14:
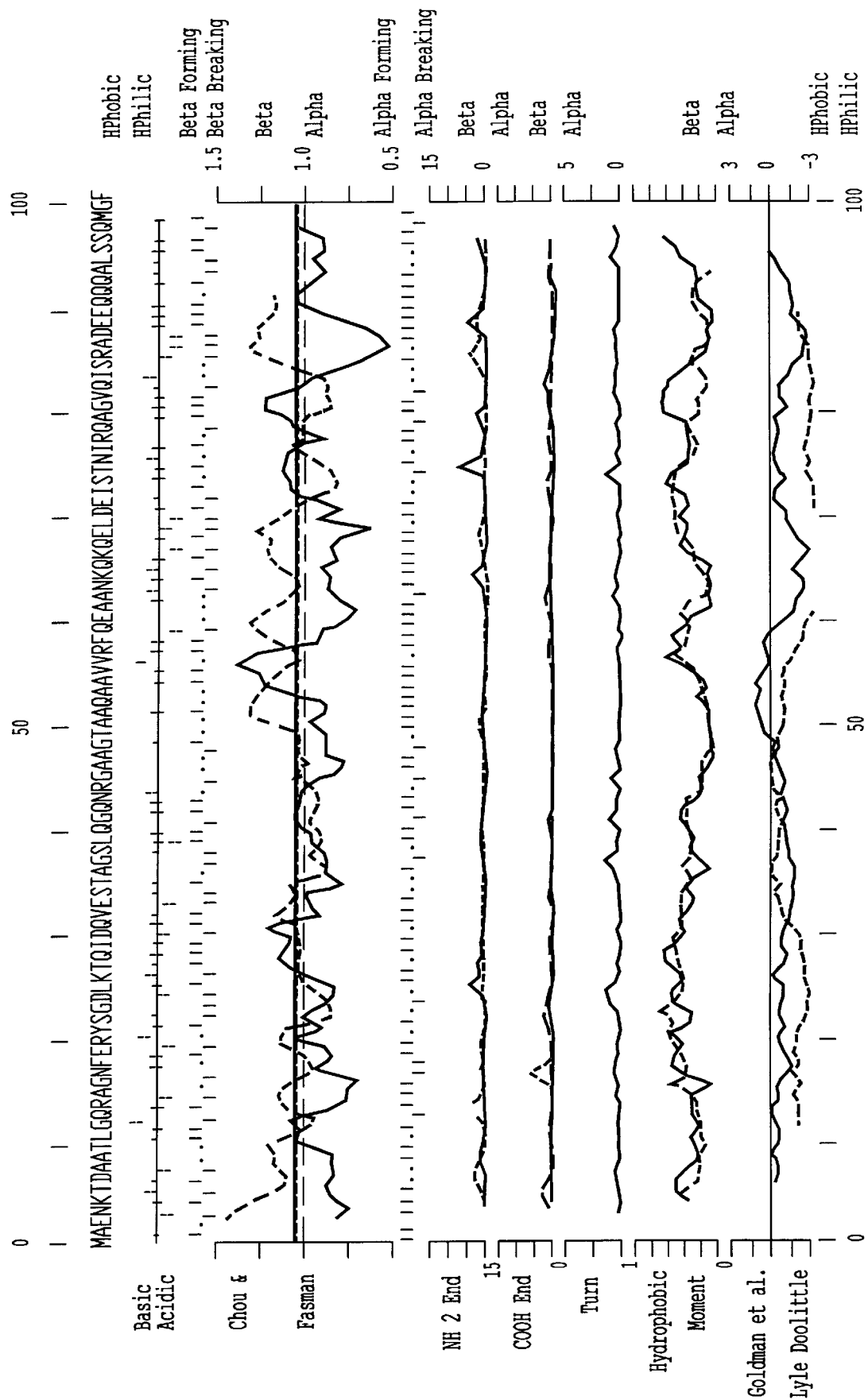

FIG. 14—Predictive analysis of the conformational and physico-chemical properties of the LHP polypeptide, as determined using the PEPPLOT™ software.

DETAILED DESCRIPTION OF THE PREFERRED EMBODIMENTS

The present inventors have discovered a new polynucleotide and have shown that said polynucleotide contains whole operon including a regulatory region containing a functional promoter and a functional ribosome binding site that drives the expression of two structural genes respectively encoding a new polypeptide named LHP and an already known polypeptide named ESAT-6.

Further, the inventors have discovered that the two structural genes are co-transcribed under the control of the said promoter region.

The inventors have further characterized the LHP polypeptide as being a polypeptide produced and excreted by *Mycobacterium tuberculosis*. The inventors have also demonstrated that the polypeptide LHP was produced simultaneously with the antigenic polypeptide ESAT-6 in *Mycobacterium tuberculosis*. As shown herein by the inventors, via a micro sequencing method of the peptides excreted in the culture medium supernatant of *Mycobacterium tuberculosis,* the LHP polypeptide is secreted by said pathogenic bacterium.

Moreover, the present inventors have shown that the regulatory region located at the 5' end of the open reading frame coding for LHP can be successfully used to drive the expression of an heterologous polynucleotide as regards to LHP in a recombinant cell host.

For this purpose, the inventors have designed three plasmids containing the regulatory region of lhp and ESAT-6 (or flC), namely plasmids pIPX30, pIPX26 and pPX1.

pIPX30 has been deposited at the CNCM (Collection de cultures de microorganisms) on Feb. 13, 1997, under the accession number I-1845. A map of plasmid pIPX30 is shown on FIG. 8. The address of the CNCM is Institut Pasteur, 28, rue du Dr Roux, 75724 Paris Cédex 15, France.

pIPX26 has been deposited at the CNCM on May 14, 1996, under the Accession Number I-1706. A map of pIPX26 is shown on FIG. 1. pIPX26 has been designed using a specific plasmid construct named pPV24 (see FIG. 11), that has been deposited at the CNCM on May 14, 1996, under the Accession Number I-1704, which is part of the invention.

pPX 1 contains the regulatory region of lhp/or flC, the open reading frame coding for lhp, the stop codon of which has been replaced by a polynucleotide coding for six histidine and ending with a stop codon. pPX1 has been deposited at the CNCM on May 14, 1996 under the Accession Number I-1707. A map of plasmid pPX1 is shown on FIG. 12. A restriction map of the 855 bp insert of plasmid pPX1 is shown in Annex III (SEQ ID NO:36) of the instant specification.

Taking into account that neither the regulatory region sequence nor the LHP encoding nucleotide sequence were found to have a strong homology with already known nucleotide sequences and then taking into account of their uniqueness in mycobacteria, a further object of the present invention consists in polynucleotides derived from the polynucleotide containing the lhp/or flC operon, or alternatively a polynucleotide hybridizing under stringent hybridization conditions with the polynucleotide containing the lhp/or flC operon, which are useful as primers or probes in order to detect specifically a bacterium of the *Mycobacterium tuberculosis* species in a biological sample.

Thus, the present invention is directed to a purified polynucleotide wherein said polynucleotide is chosen from the group consisting of:

(a) a polynucleotide comprising the following nucleotide sequence of SEQ ID NO 1:

CTGCAGCAGGTGACGTCGTTGTTCAGCCAGGT GGGCGGCACCGGCGGCGGCAACCCAGCCG ACGAGGAAGCCGCGCAGATG

GGCCTGCTCGGCACCAGTCCGCTGTCGAACCATC CGCTGGCTGGTGGATCAGGCCCCAGCGCGG GCGCGGGCCTGCTGCG

CGCGGAGTCGCTACCTGGCGCAGGTGGGTCGT TGACCCGCACGCCGCTGATGTCTCAGCTGA TCGAAAAGCCGGTTGCCC

CCTCGGTGATGCCGGCGGCTGTTGCCGGATCGTC GGTGACGGGTGGCGCCGCTCCGGTGGGTCC GGGAGCGATGGGCCAG

GGTTCGCAATCCGGCGGCTCCACCAGCCCGGGT CTGGTCGCGCCGGCACCGCTCGCGCAGGA GCGTGAAGAAGACGACGA

GGACGACTGGGACGAAGAGGACGACTGGTGAG CTCCCGTAATGACAACAGACTTCCCGGCCA CCCGGGCCGGAAGACTTG

CCAACATTTTGGCGAGGAAGGTAAAGAGAGAAAG TAGTCCAGCATGGCAGAGATGAAGACCGATG CCGCTACCCTCGGGC

AGGAGGCAGGTAATTTCGAGCGGATCTCCGG CGACCTGAAAACCCAGATCGACCAGGTGGAG TCGACGGCAGGTTCGTTG

CAGGGCCAGTGGCGCGGCGCGGCGGGGACGGCCG CCCAGGCCGCGGTGGTGCGCTTCCAAGAAGC AGCCAATAAGCAGAA

GCAGGAACTCGACGAGATCTCGACGAATATTCGTC AGGCCGGCGTCCAATACTCGAGGGCCGACGA GGAGCAGCAGCAGG

CGCTGTCCTCGCAAATGGGCTTCTGACCCGCTAAT ACGAAAAGAAACGGAGCAAAAACATGACAGA GCAGCAGTGGAATT

TCGCGGGTATCGAGGCCGCGGCAAGCGCAATCCAG GGAAATGTCACGTCCATTCATTCCCTCCTTGAC GAGGGGAAGCAG

TCCCTGACCAAGCTCGCAGCGGCCTGGGGCGG TAGCGGTTCGGAGGCGTACCAGGGTGTCCAG CAAAAATGGGACGCCAC

GGCTACCGAGCTGAACAACGCGCTGCAGAACC TGGCGCGGACGATCAGCGAAGCCGGTCAGGC AATGGCTTCGACCGAAG

GCAACGTCACTGGGATGTTCGCATAGGGCAAC GCCGAGTTCGCGTAGAATAGCGAAACACGGGA TCGGGCGAGTTCGACC

TTCCGTCGGTCTCGCCCTTTCTCGTGTTTATACGT TTGAGCGCACTCTGAGAGGTTGTCATGGCGGC CGACTACGA (b) a polynucleotide comprising the following nucleotide sequence of SEQ ID NO 2, starting at its 5' end with the nucleotide in position 1 of SEQ ID NO 1 and ending at its 3' end with the nucleotide in position 524 of SEQ ID NO 1, or a biologically active polynucleotide derivative of SEQ ID NO 2:

CTGCAGCAGGTGACGTCGTTGTTCAGCCAGGTGG GCGGCACCGGCGGCGGCAACCCAGCCGACG AGGAAGCCGCGCAGATG

GGCCTGCTCGGCACCAGTCCGCTGTCGAACCA TCCGCTGGCTGGTGGATCAGGCCCCAGCGCG GGCGCGGGCCTGCTGCG

CGCGGAGTCGCTACCTGGCGCAGGTGGGTCG TTGACCCGCACGCCGCTGATGTCTCAGCTGAT CGAAAAGCCGGTTGCCC

CCTCGGTGATGCCGGCGGCTGTTGCCGGATCGTC GGTGACGGGTGGCGCCGCTCCGGTGGGTCC GGGAGCGATGGGCCAG

GGTTCGCAATCCGGCGGCTCCACCAGCCCGGGTC TGGTCGCGCCGGCACCGCTCGCGCAGGAGCGTG AAGAAGACGACGA

GGACGACTGGGACGAAGAGGACGACTGGTGAGCT
CCCGTAATGACAACAGACTTCCCGGCCACCCGG
GCCGGAAGACTTG
CCAACATTTTGGCGAGGAAGGTAAAGAGAGAAA
GTAGTCCAGC (c) a polynucleotide comprising the following nucleotide sequence of SEQ ID NO 3, starting at its 5' end with the nucleotide in position 1 of SEQ ID NO 1 and ending at its 3' end with the nucleotide in position 481 of SEQ ID NO 1, or a biologically active polynucleotide derivative of SEQ ID NO 3:

CTGCAGCAGGTGACGTCGTTGTTCAGCCAGGTGG
GCGGCACCGGCGGCGGCAACCCAGCCGACGAG
GAAGCCGCGCAGATG
GGCCTGCTCGGCACCAGTCCGCTGTCGAACCATC
CGCTGGCTGGTGGATCAGGCCCCAGCGCG
GGCGCGGGCCTGCTGCG
CGCGGAGTCGCTACCTGGCGCAGGTGGGTC
GTTGACCCGCACGCCGCTGATGTCTCAGCTGATC
GAAAAGCCGGTTGCCC
CCTCGGTGATGCCGGCGGCTGTTGCCGGATCGT
CGGTGACGGGTGGCGCCGCTCCGGTGGGTCCG
GGAGCGATGGGCCAG
GGTTCGCAATCCGGCGGCTCCACCAGCCCGGGTCT
GGTCGCGCCGGCACCGCTCGCGCAGGAGCGTG
AAGAAGACGACGA
GGACGACTGGGACGAAGAGGACGACTGGTGAGC
TCCCGTAATGACAACAGACTTCCCGGCCACCCG
GGCCGGAAGACTTG (d) a polynucleotide comprising the following nucleotide sequence of SEQ ID NO 4, starting at its 5' end with the nucleotide in position 525 of SEQ ID NO 1 and ending at its 3' end with the nucleotide in position 826 of SEQ ID NO 1 coding for the LHP polypeptide:

ATGGCAGAGATGAAGACCGATGCCGCTACCCTC
GGGC
AGGAGGCAGGTAATTTCGAGCGGATCTCCGGC
GACCTGAAAACCCAGATCGACCAGGTGGAGTCG
ACGGCAGGTTCGTTG
CAGGGCCAGTGGCGCGGCGCGGCGGGGACGGC
CGCCCAGGCCGCGGTGGTGCGCTTCCAAGAAG
CAGCCAATAAGCAGAA
GCAGGAACTCGACGAGATCTCGACGAATATTCGTC
AGGCCGGCGTCCAATACTCGAGGGCCGACG
AGGAGCAGCAGCAGG
CGCTGTCCTCGCAAATGGGCTTCTG (e) a polynucleotide comprising at least 12 consecutive nucleotides of a polynucleotide chosen among the group consisting of SEQ ID NO 2, SEQ ID NO 3 or SEQ ID NO 4;

(f) a polynucleotide having a sequence filly complementary to a polynucleotide chosen among the group consisting of SEQ ID NO 2, SEQ ID NO 3 or SEQ ID NO 4;

(g) a polynucleotide hybridizing under stringent hybridization conditions with a polynucleotide chosen among the group consisting of SEQ ID NO 2, SEQ ID NO 3 or SEQ ID NO 4.

By a biologically active polynucleotide derivative of SEQ ID NO 2 or SEQ ID NO 3 according to the present invention is meant a polynucleotide comprising or alternatively consisting in a fragment of said polynucleotide which is functional as a regulatory region for expressing a recombinant polypeptide in a recombinant cell host.

More specifically, a typical biologically active polynucleotide derivative of SEQ ID NO 2 or SEQ ID NO 3 is a polynucleotide comprising at least the nucleotide region containing one transcription start site chosen among the transcription start sites respectively located at the nucleotide in position 454 of SEQ ID NO 1 and at the nucleotide in position 513 of SEQ ID NO 1.

In a particular embodiment of a biologically active derivative of SEQ ID NO 2 or SEQ ID NO 3 the ribosome binding site (shine Dalgarno sequence) which is located from the nucleotide at position 508 to the nucleotide at position 512 of SEQ ID NO 1 may be removed or absent and optionally replaced by a suitable natural or synthetic ribosome binding site, depending on the recombinant cell host in which its expression is desired.

As shown by the inventors, LHP is produced in short term culture filtrates of Mycobacterium tuberculosis, thus in the same time as ESAT-6. LHP and ESAT-6 may have a synergistic action in inducing a protective immune response against a pathogenic mycobacterium, specifically mycobacteria belonging to the tuberculosis-complex. Thus, it is a preferred embodiment of the present invention to obtain a composition containing simultaneously LHP and ESAT-6, optionally in combination with other antigenic proteins from Mycobacterium tuberculosis, such as, for example, the 45/47 kDa protein or the 19 kDa, DES, ERP (28 Kd) or any protein identified by biochemical or genetic means. Such a composition containing both at least LHP and ESAT-6 may be under the form of a polypeptide composition or under the form of a composition of live recombinant cell host expressing both proteins or an admixture of recombinant cell hosts each expressing one protein chosen among LHP or ESAT-6, the whole compositions being useful for immunodiagnostics or vaccine purposes.

Figure 1:
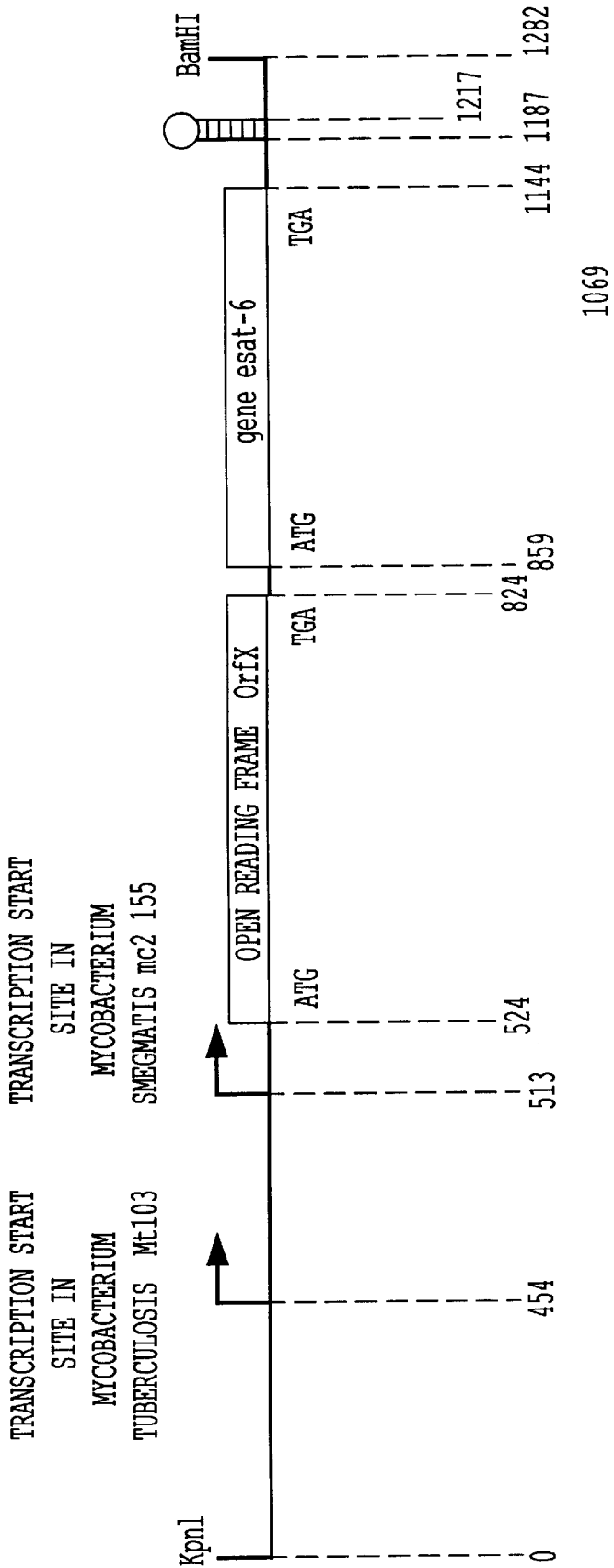
FIG. 1—Main features of the nucleotide insert contained in plasmid pIPX26 that has been deposited at the CNCM on May 14, 1996 under the Accession Number I-1706. This insert contains the whole polynucleotide carrying the lhp-or flC operon. pIPX26 is a shuttle cloning vector (*E. Coli*—mycobacteria) of the pPV24 kind conferring kanamycin resistance and carrying a DNA insert at the unique cloning sites KpnI (Asp718) and BamHI). This DNA insert is a 1282 bp DNA fragment form *Mycobacterium tuberculosis* H37Rv, which has been generated by PCR amplification using the following pair of primers: ESB-1 (5'-GGGGGGATCCGGTACCAGGTGACGTCGTTGTTCAG CCAG-3')(SEQ ID NO:21) AND ESB-2 (5'-GGGGGGTACCGGATCCTCGTAGTCGGCCGCCATGA CAAC-3')(SEQ ID NO:22, and by digestion with the restriction enzymes Asp718 and BamHI. This DNA fragment carries the open reading frame referenced or fX (which is the lhp gene), the ESAT-6 (also referred to as or flC) gene and its own transcription terminator. This DNA fragment comprises also a promoter activity and transcription start sites allowing gene expression, including lhp and ESAT-6 (or flC) in *M. smegmatis* and *M. bovis*-BCG.

In a specific embodiment of a recombinant vector according to the present invention, such a recombinant vector contains a regulatory polynucleotide of the invention which is placed in the suitable frame with regards to a polynucleotide containing two open reading frames encoding respectively LHP and ESAT-6. Such a plasmid may be, for example, pIPX26 that has been deposited at the CNCM under the Accession Number I-1706 (see FIG. 1 and Annex II). Another suitable recombinant plasmid is plasmid pPX1 that is contained in the E. coli strain that has been deposited at the CNCM on May 14, 1996, under the Accession Number I-1707 (see FIG. 12 and Annex III).

In order to identify the relevant biologically active polynucleotide derivatives of the invention that are described hereinbefore, the one skilled in the art will refer to the Example 5 and 6 of the instant specification in order to use a recombinant vector carrying a marker gene the expression of which will be detected when placed under the control of a biologically active derivative polynucleotide of SEQ ID NO 2 or 3.

Said regulatory polynucleotides may be prepared from any of the SEQ ID NO 1, SEQ ID NO 2 or SEQ ID NO 3 by cleavage using the suitable restriction enzymes, the one skilled in the art being guided by the restriction maps presented in Annexes I to III. Annex I represents the 1069 bp nucleotide sequence of the PstI DNA insert contained in plasmid pIPX61 (SEQ ID NO:37) (see FIG. 3). Annex II represents the 1282 bp nucleotide sequence of the KpnI BamHI DNA insert contained in plasmid pIPX26 (SEQ ID NO:38) (see FIG. 1). Annex III represents the 855 bp nucleotide sequence of the DNA insert of plasmid pPX1 (SEQ ID NO:36).

Said regulatory polynucleotides may also be prepared by digestion of any of SEQ ID NO 1, SEQ ID NO 2 or SEQ ID NO 3 by an exonuclease enzyme, such as for example Bal31(Wabiko et al., 1986).

Another object of the present invention is a recombinant vector containing a polynucleotide of SEQ ID NO 2 or SEQ ID NO 3, or a biologically polynucleotide derivative thereof, and a polynucleotide coding for a polypeptide.

In a specific embodiment of the recombinant vector according to the present invention, the polynucleotide of SEQ ID NO 2 or one of its biologically active derivatives, or a biologically active derivative of SEQ ID NO 3 lacking the ribosome binding site sequence will have to be located in the suitable frame with an heterologous Shine-Dalgarno type sequence in order to allow the expression of the polypeptide encoding gene placed under its control.

The preferred expression vectors carrying the polynucleotide of SEQ ID NO 2 or SEQ ID NO 3 or one of their biologically active polynucleotide derivatives are the conventional vectors used for polypeptide expression in bacteria, such as for example plasmids of the pUC family or plasmids of the pAL family.

A specific recombinant vector according to the present invention is the plasmid pIPX30 which has been deposited at the CNCM on Feb. 13, 1997 under the Accession Number I-1845. A map of plasmid pIPX30 is represented on FIG. 8.

The polypeptide encoded by a polynucleotide contained in a recombinant vector according to the present invention may be any kind of polypeptide either of eukaryotic or prokaryotic origin.

Preferably said polynucleotide codes for an antigenic protein of a mycobacterium, and preferably a mycobacterium belonging to the *Mycobacterium tuberculosis* complex.

In a most preferred embodiment, the encoded antigenic polypeptide or protein is a polypeptide which undergoes post translational modifications in the mycobacterium, such as phosphorylation, glycosylation or acylation. Such preferred postranslationally modified antigenic mycobacterial polypeptides are, for example, the 19 kDa antigen from *Mycobacterium tuberculosis*, the expression of which is described by Herrmann et al., 1996, Harris et al., 1994 and by Garbe et al., 1993, and possibly LHP or ESAT-6.

Other antigenic mycobacterial polypeptides of interest that may be expressed under the control of a regulatory polynucleotide according to the present invention are the following: DnaK, GroEL, GroES, the 45/47 kD polypeptide from *Mycobacterium tuberculosis* (Bengard et al., 1994).

The present invention concerns also the polynucleotide insert of a recombinant vector as defined hereinbefore.

The invention also concerns a recombinant cell host containing a purified polynucleotide insert as defined hereinbefore or a recombinant vector according to the invention.

The recombinant cell host may be a bacteria, such as for example *E. coli*.

A recombinant cell host according to the present invention consists in a fast growing or a slow growing mycobacterium. Preferably, it consists in a mycobacterium belonging to the *Mycobacterium tuberculosis* complex, more specifically the species *Mycobacterium tuberculosis* itself or *Mycobacterium bovis*-BCG or mutants of these strains. Another embodiment of a mycobacterium recombinant cell host according to the present invention consists in *Mycobacterium smegmatis*.

Another object of the present invention consists in a purified polypeptide produced by a recombinant cell host according to the invention.

A method for preparing such a recombinant polypeptide comprises typically the steps of: (a) optionally preparing a recombinant vector as described above; (b) optionally introducing said recombinant vector in a suitable eukaryotic or prokaryotic cell host; (c) cultivating the recombinant cell host of step (b); (d) purifying the recombinant polypeptide produced in the culture supernatant medium or in the recombinant cell host cell lysate.

In another aspect of the present invention, polynucleotides of SEQ ID NO 2, SEQ ID NO 3 or SEQ ID NO 4 are useful as starting material in order to design new polynucleotides that hybridize specifically under stringent hybridization conditions with the polynucleotide of SEQ ID NO 1, said new polynucleotides being used as oligonucleotide primers or probes.

Consequently is also part of the present invention a polynucleotide or oligonucleotide comprising at least 12 consecutive nucleotides of a polynucleotide chosen among the group consisting of SEQ ID NO 2, SEQ ID NO 3 or SEQ ID NO 4.

By a polynucleotide or oligonucleotide hybridizing under stringent hybridization conditions according to the present invention is meant a polynucleotide that hybridizes with a polynucleotide of SEQ ID NO 2, SEQ ID NO 3 or SEQ ID NO 4 under the following hybridization conditions:

The hybridization step is realized at 65° C. in the presence of 6×SSC buffer, 5×Denhardt's solution, 0.5% SDS and 100 μg/ml of salmon sperm DNA.

The hybridization step is followed by four washing steps:

two washings during 5 min, preferably at 65° C. in a 2×SSC and 0.1% SDS buffer;

one washing during 30 min, preferably at 65° C. in a 2×SSC and 0.1% SDS buffer;

one washing during 10 min, preferably at 65° C. in a 0.1×SSC and 0.1% SDS buffer.

Thus, the polynucleotides of SEQ ID NO 2, SEQ ID NO 3 and SEQ ID NO 4, or the nucleic fragments obtained from such polynucleotides may be used to select nucleotide primers notably for an amplification reaction such as the amplification reactions further described.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using as nucleic probes the polynucleotides SEQ ID NO 2, SEQ ID NO 3 and SEQ ID NO 4, fragments thereof, oligonucleotides that are complementary to these polynucleotides or fragment thereof or their amplification products themselves.

Amplified nucleotide fragments are used as probes that are useful in hybridization reactions in order to detect the presence of one polynucleotide according to the present invention or in order to detect mutations in the SEQ ID NO 2, SEQ ID NO 3 and SEQ ID NO 4.

Are also part of the present invention the amplified nucleic fragments ("amplicons") defined herein above.

These probes and amplicons may be radioactively or non-radioactively labeled, using for example enzymes or fluorescent compounds.

Such nucleic acid fragments may be used as pairs in order to amplify specific regions of SEQ ID NO 2, SEQ ID NO 3 and SEQ ID NO 4.

Preferred nucleic acid fragments that can serve as primers according to the present invention are the following:

SEQ ID NO 14: 5'-CTGCAGCAGGTGACGTCGTTG-3' (from nucleotide in position 1 to the nucleotide in position 21 of SEQ ID NO 1.

SEQ ID NO 15: 5'-CCGGGTGGCCGGGAAGT CTGTGT-3' (complementary of the sequence from nucleotide in position 468 to the nucleotide in position 446 of SEQ ID NO 1).

SEQ ID NO 16: 5'-ACTACTTTCTCTTTCTACCTTCC-3' (complementary of the sequence from nucleotide in position 519 to the nucleotide in position 497 of SEQ ID NO 1).

The above described primers are used in combination for performing a nucleic acid amplification of one polynucleotide according to the present invention. Suitable pairs of primers used are the following: (a) SEQ ID NO 14 and SEQ ID NO 15; (b) SEQ ID NO 14 and SEQ ID NO 16.

It is no need to say that any one of the above described primers may be also used as specific probes according to the invention.

The primers may also be used as oligonucleotide probes to specifically detect a polynucleotide according to the invention.

The primers may also be used as oligonucleotide probes to specifically detect a polynucleotide according to the invention.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recognition site (which is under a hemiphosphorothioate form) and on the property of a DNA polymerase to initiate the synthesis of a new strand from the 3' OH end generated by the restriction enzyme and on the property of this DNA polymerase to displace the previously synthesized strand being localized downstream. The SDA method comprises two main steps: (a) the synthesis in the presence of dCTP-alpha-S, of DNA molecules that are flanked by the restriction sites that may be cleaved by an appropriate enzyme; (b) the exponential amplification of these DNA molecules modified as such by enzyme cleavage, strand displacement and copying of the displaced strands. The steps of cleavage, strand displacement and copying of the displaced strands. The steps of cleavage, strand displacement and copying are repeated a sufficient number of times in order to obtain an accurate sensitivity of the assay.

The SDA technique was initially realized using the restriction endonuclease HincII but is now generally practiced with an endonuclease from *Bacillus stearothermophilis* (BSOBI) and a fragment of a DNA polymerase which is devoid of and 5'Õ3' exonuclease activity isolated from *Bacillus cladotenax* (exo-Bca) [=exo-minus-Bca]. Both enzymes are able to operate at 60° C. and the system is now optimized in order to allow the use of dUTP and the decontamination by UDG. When using this technique as described by Spargo et al. In 1996, the doubling time of the target DNA is of 26 seconds and the amplification rate is $10^{10}$ after an incubation time of 15 min at 60° C.

The SDA amplification technique is easier to perform than PCR (a single thermostated water bath device is necessary) and is faster than the other amplification methods.

Thus, another object of the present invention consists in using the nucleic acid fragments according to the invention (primers) in a method of DNA or RNA amplification according to the SDA technique. For performing of SDA, two pairs of primers are used: a pair of external primers (B1, B2) consisting in a sequence specific of the target polynucleotide of interest and a pair of internal primers (S1, S2) consisting in a fusion oligonucleotide carrying a site that is recognized by a restriction endonuclease, for example the enzyme BSOBI.

As an illustrative embodiment of the use of the primers according to the invention in a SDA amplification reaction, a sequence that is non specific for the target polynucleotide and carrying a restriction site for HincII or BSOBI is added at the 5' end of a primer specific either for SEQ ID NO 2, SEQ ID NO 3 and SEQ ID NO 4. Such an additional sequence containing a restriction site that is recognized by BSOBI is advantageously the following sequence: GCATCGAATGCATGTCTCGGGT,(SEQ ID NO:17 the nucleotides represented in bold characters corresponding to the recognition site of the enzyme BSOBI. Thus, primers useful for performing SDA amplification may be designed from any of the primers according to the invention as described above and are part of the present invention. The operating conditions to perform SDA with such primers are described in Spargo et al 1996.

More specifically, the following conditions are used when performing the SDA amplification reaction with the primers of the invention designed to contain a BSOBI restriction site: BSOBI/exo⁻Bca [=exo-minus-Bca] SDA reactions are performed in a 50 µl volume with final concentrations of 9.5 mM $MgCl_2$, 1.4 mM each dGTP, dATP, TTP, dCTP-alpha-S, 100 µg/ml acetylated bovine serum albumin, 10 ng/ml human placental DNA, 35 mM $K_2HPO_4$ pH 7.6, 0.5 µM primers $S1_{BSOBI}$ and $B2_{BSOBI}$, 0.05 µM primers $B1_{BSOBI}$ and $B2_{BSOBI}$, 3.2 U/µl BSOBI enzyme, 0.16 U/µl exo⁻Bca [=exo-minus-Bca] enzyme, 3 mM Tris-HCl, 11 mM NaCl, 0.3 mM DTT, 4 mM KCl, 4% glycerol, 0.008 mM EDTA, and varying amounts of target DNA. Prior to the addition of BSOBI and exo⁻Bca, incomplete reactions (35 µl) are heated at 95° C. for 3 min to denature the target DNA, followed by 3 min at 60° C. to anneal the primers. Following the addition of a 15 µl enzyme mix consisting of 4 µl of BSOBI (40 Units/µl), 0.36 µl exo⁻Bca (22 Units/µl), and 10.6 µl enzyme dilution buffer (10 mM Tris HCl, 10 mM $MgCl_2$, 50 mM NaCl, 1 mM DTT), the reactions are incubated at 60° C. for 15 min. Amplification is terminated by heating for 5 min in a boiling water bath. A no-SDA sample is created by heating a sample in a boiling water bath immediately after enzyme addition. Aerosol resistant tips from Continental Laboratory Products are used to reduce contamination of SDA reactions with previously amplified products.

The polynucleotides of SEQ ID NO 2, SEQ ID NO 3 and SEQ ID NO 4 and their above described fragments, especially the primers according to the invention, are useful in performing different target nucleic acid amplification methods such as:

TAS (Transcription-based Amplification system), described by Kwoh et al. in 1989;

SR (Self-sustained Sequence Replication), described by Guatelli et al. in 1990;

NASBA (Nucleic Acid Sequence Based Amplification), described by Kievitis et al. in 1991.

TMA (Transcription Mediated Amplification).

The polynucleotides of SEQ ID NO 2, SEQ ID NO 3 and SEQ ID NO 4 and their above described fragments, especially the primers according to the invention, are also useful as technical means for performing methods for amplification or modification of a nucleic acid used as a probe, such as:

LCR (Ligase Chain Reaction), described by Landegren et al. in 1988 and improved by Barney et al. in 1991 who employ a thermostable ligase.

RCR (Repair Chain Reaction), described by Segev et al. in 1992.

CPR (Cycling Probe Reaction), described by Duck et al. in 1990.

Q-Beta Replicase Reaction, described by Miele et al. in 1983 and improved by Chu et al. in 1986, Lizardi et al. in 1988 and by Burg et al. and Stone et al. in 1996.

When the target polynucleotide to be detected is a RNA, for example, a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

Thus, another object of the present invention consists in a method for detecting *Mycobacterium tuberculosis* in a biological sample comprising the steps of: (a) bringing into contact the nucleic acid molecules contained in the biological sample with a pair of purified polynucleotides primers derived from a polynucleotide of SEQ ID NO 2, SEQ ID NO 3 or SEQ ID NO 4; (b) amplifying said nucleic acid molecules; (c) detecting the nucleic acid fragments that have been amplified, for example, by gel electrophoresis or with a labeled polynucleotide hybridizing specifically with a polynucleotide of SEQ ID NO 2, SEQ ID NO 3 or SEQ ID NO 4.

The invention concerns also the above method, wherein before step (a), the nucleic acid molecules of the biological sample have been made available to a hybridization reaction.

The invention is also related to a kit for detecting a *Mycobacterium tuberculosis* bacterium in a biological sample comprising: (a) a pair of purified oligonucleotides primers according to the invention; (b) reagents necessary to perform a nucleic acid amplification reaction; (c) optionally, a purified polynucleotide according to anyone of claims useful as a probe.

The non-labeled polynucleotides or oligonucleotides of the invention may be directly used as probes. Nevertheless, the polynucleotides or oligonucleotides are generally labeled with a radioactive element ($^{32}$P, $^{35}$S, $^{3}$H, $^{125}$I) or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the French Patent No FR-7810975 or by Urdea et al. or Sanchez-Pescador et al., 1988.

In the latter case, other labeling techniques may be also used such those described in the French Patent Nos. FR-2, 422,956 and 2,518,755. The hybridization step may be performed in different ways (Matthews et al., 1988). The more general method consists in immobilizing the nucleic acid that has been extracted from the biological sample on a substrate (nitrocellulose, nylon, polystyrene) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European Patent No. EP-0225,807 (Chiron).

In another advantageous embodiment of the probes according to the present invention, they may be used as "capture probes", and are for this purpose immobilized on a substrate in order to capture the target nucleic acid contained in a biological sample. The captured target nucleic acid is subsequently detected with a second probe which recognizes a sequence of the target nucleic acid which is different from the sequence recognized by the capture probe.

The oligonucleotide fragments useful as probes or primers according to the present invention may be prepared by cleavage of the polynucleotides of SEQ ID NO 2, SEQ ID NO 3 and SEQ ID NO 4 by restriction enzymes, the one skilled in the art being guided by the restriction maps presented in the annexes I and II of the instant Specification. The experimental procedure conditions suitable for using the restriction enzymes are described in Sambrook et al. (1989).

Another appropriate preparation process of the nucleic acids of the invention containing at most 200 nucleotides (or 200 bp if these molecules are double stranded) comprises the following steps:

synthesizing DNA using the automated method of beta-cyanethylphosphoramidite described in 1986;

cloning the thus obtained nucleic acids in an appropriate vector;

purifying the nucleic acid by hybridizing an appropriate probe according to the present invention.

A chemical method for producing the nucleic acids according to the invention which have a length of more than 200 nucleotides (or 200 bp if these molecules are double stranded) comprises the following steps:

assembling the chemically synthesized oligonucleotides, having different restriction sites at each end;

cloning the thus obtained nucleic acids in an appropriate vector;

purifying the nucleic acid by hybridizing an appropriate probe according to the present invention.

In the case in which the above nucleic acids are used as coding sequences in order to produce a polypeptide according to the present invention, it is important to ensure that their sequences are compatible (in the appropriate reading frame) with the amino acid sequence of the polypeptide to be produced.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary of a distinct sequence of the target nucleic acid. Optionally, the substrate of the matrix may be a material able to act as an electron donor, the detection of the matrix positions in which an hybridization has occurred being subsequently determined by an electronic device. Such matrix libraries of probes and methods of specific detection of a target nucleic acid is described in the European Patent Application No. EP-0713, 016 (Affymax Technologies) and also in the U.S. Pat. No. 5,202,23 1 (Drmanac).

Thus, another object of the present invention consists in a method for detecting the presence of *Mycobacterium tuberculosis* bacteria in a biological sample comprising the steps of: (a) bringing into contact a purified polynucleotide derived from SEQ ID NO 2, SEQ ID NO 3 or SEQ ID NO 4 with a nucleic acid contained in the biological sample; (b) detecting the hybrid nucleic acid molecule formed between said purified polynucleotide and the nucleic acid molecules contained within the biological sample.

In a particular embodiment of the above method, the nucleic acid molecules of the biological sample have been made available to a hybridization reaction before performing step (a).

The invention also concerns a method for detecting a *Mycobacterium tuberculosis* bacterium in a biological sample comprising the steps of: (a) bringing into contact a purified polynucleotide probe according to the invention that has been immobilized onto a substrate with a biological sample; (b) bringing into contact the hybrid nucleic acid molecule formed between said purified polynucleotide and the nucleic acid contained in the biological sample with a labeled polynucleotide probe according to the invention, provided that the probe of step (a) and the probe of step (b) have non-overlapping nucleotide sequences.

The invention pertains also to the above method wherein, before step (a), the nucleic acid molecules of the biological sample have been made available to a hybridization reaction.

The invention is also directed to the above method wherein, before step (b), the nucleic acid molecules that are not hybridized with the immobilized purified polynucleotide are removed.

Another object of the present invention consists in a kit for detecting a *Mycobacterium tuberculosis* bacterium genus in a biological sample comprising; (a) a purified polynucleotide probe according to the invention; (b) reagents necessary to perform a nucleic acid hybridization reaction.

The invention also pertains to a kit for detecting a *Mycobacterium tuberculosis* bacterium in a biological sample comprising: (a) a purified polynucleotide probe according to the invention that is immobilized onto a substrate; (b) reagents necessary to perform a nucleic acid hybridization reaction; (c) a purified polynucleotide probe according to the invention which is radioactively or non-radioactively labeled, provided that the probe of step (a) and the probe of step (b) have non-overlapping nucleotide sequences.

As already specified, the present inventors have characterized a new polypeptide, named LHP, that is encoded by the polynucleotide sequence of SEQ ID NO 1, and more precisely by the polynucleotide of sequence SEQ ID NO 4. The polynucleotide of SEQ ID NO 4 encodes the LHP polypeptide of SEQ ID NO 5 which is described hereunder.

Thus, another object of the present invention consists in a purified polypeptide, named LHP, and having the following amino acid sequence SEQ ID NO 5: MAEMKTDA ATLGQEAGNFERISGDLKTQIDQVESTAGSLQGQ WRGAAGTAAQAAVVRFQEAANKQKQELDEIST NIRQAGVQYSRADEEQQQALSSQMGF.

The correspondence between the one letter-code and the three letter-codes for amino acids is found in the book of Stryer *Biochemistry*, Third Ed. (1988), which is incorporated here by reference for all purposes.

In both immunodiagnostics and vaccine preparation it is often possible and practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analysis or Hopp and Woods (1981) hydrophobicity analysis (see e.g., Jameson-Wolf, 1988; Kyte and Doolittle, 1982; U.S. Pat. No. 4,554, 101). Hydrophobicity analysis assigns average hydophilicity values to each amino acid residue from these values average hydrophilicities can be calculated and regions of greatest hydrophilicity determined. Using one or more of these methods, regions of predicted antigenicity are derived from the amino acid sequence assigned to the polypeptides according to the present invention.

The present invention is also directed to portions of the polypeptide of amino acid sequence of SEQ D NO 5 that are highly immunogenic and which may thus serve as components of an immunogenic composition or a vaccine composition for the purpose of diagnosing or preventing an *Mycobacterium tuberculosis* infection in a patient.

In order to identify the relevant antigenic or immunogenic portions of the polypeptide of SEQ ID NO 5, one skilled in the art may bring a specific peptide derived from the polypeptide of SEQ ID NO 5 in the presence of a serum sample of a patient infected with *Mycobacterium tuberculosis* and then detect the complex eventually formed between the antibodies contained in the serum sample and the peptide being assayed. Such a screening assay used to define the relevant immunogenic portions of the polypeptide of SEQ ID NO 5 is advantageously a conventional ELIZA type assay, wherein, as an illustrated embodiment, radioactively or fluorescently anti-Ig antibodies are used for detecting the antigen-antibody complexes formed.

Antigenic portions of the LHP polypeptide may be obtained by enzymatic cleavage of the parent purified polypeptide, one skilled in the art being guided by the digestion map of the polypeptide of SEQ ID NO 5 represented in Annex IV.

Preferred antigenic portion of the polypeptide according to the present invention are comprising the hydrophilic parts of the LHP polypeptide as determined notably in FIGS. 13 and 14.

Thus, the preferred antigenic portions of a polypeptide according to the invention comprise peptides or pseudopeptides derived from the following peptides consisting in: (a) amino acid in position 1 to amino acid in position 48 of SEQ ID NO 5; (b) amino acid in position 60 to amino acid in position 100 of SEQ ID NO 5; which represent the most hydrophilic regions of the LHP polypeptide of the invention.

Specific immunogenic portions of the polypeptide of SEQ ID NO 5 characterized by the inventors are the following:

(a) SEQ ID NO 6: NH2-MAEMKTDAATLGQEAGNFER ISGDLKTQIDQVESTAGSLQGQWRGAAGT-COOH;

(b) SEQ ID NO 7: NH2-QEAANKQKQELDEISTNI RQAGVQYSRADEEQQQALSSQMGF-COOH;

(c) SEQ ID NO 8: NH2-QEAGNFERISGDLKTQIDQV-COOH;

(d) SEQ ID NO 9: NH2-GDLKTQIDQVESTAGS-COOH;

(e) SEQ ID NO 10: NH2-GSLQGQWRGAAGTAAA-COOH;

(f) SEQ ID NO 11: NH2-QEAANKQKQELDEIST-COOH;

(g) SEQ ID NO 12: NH2-STNIRQAGVQYSRADEE QQQALSSQMGF-COOH;

(h) SEQ ID NO 13: NH2-RADEEQQQALSSQMGF-COOH.

In a preferred embodiment of the immunogenic polypeptide according to the present invention, the epitope unit of said polypeptide is from 6 to 50 amino acids in length, preferably from 6 to 20 amino acids in length and most preferably from 6 to 15 amino acids in length, and is able to induce in vivo a protective immune response against the LHP antigen which is expressed by *Mycobacterium tuberculosis*. An immunogenic polypeptide having a long amino acid chain (from 25 to 50 amino acids in length) is preferably used in case of conformational epitope units. Furthermore, a large epitope unit is expected to carry both a B-epitope and a T-epitope.

By an epitope or an epitope unit according to the present invention is meant a portion of the LHP polypeptide which is delinated by the area of interaction with antibodies that are specific to LHP, in particular monoclonal antibodies directed against LHP. The above disclosed immunogenic portions of the LHP polypeptide of SEQ ID NO 5 all bear at least one epitope unit.

Are also part of the immunogenic polypeptides of the present invention those polypeptides which comprise, but are not limited to, at least one epitope unit recognized by a monoclonal antibody directed against the LHP polypeptide or a peptide fragment thereof.

Specifically, the monoclonal or polyclonal antibody according to the invention recognizes the LHP polypeptide of SEQ ID NO 5 or one peptide fragment thereof.

The antibodies may be prepared from hybridomas according to the technique described by Phalipon et al. in 1995 or also by Kohler and Milstein in 1975. The polyclonal antibodies may be prepared by immunization of a mammal, especially a mouse or a rabbit, with a polypeptide according to the invention that is combined with an adjuvant of immunity, and then by purifying of the specific antibodies contained in the serum of the immunized animal on an affinity chromatography column on which has previously been immobilized the polypeptide that has been used as the antigen.

The present invention is also directed to a diagnostic method for detecting the presence of a *Mycobacterium tuberculosis* is a biological sample, said diagnostic method comprising the steps of: (a) bringing into contact the biological sample expected to contain a *Mycobacterium tuberculosis* bacterium with a purified monoclonal or polyclonal antibody according to the invention; (b) detecting the antigen-antibody complexes formed.

In a specific embodiment of the above diagnostic method, step (a) is preceded by preparing a purified preparation of the said anti-immunogenic polypeptide monoclonal or polyclonal antibody.

In a preferred embodiment of the above diagnostic method, said method consists in an immunoassay including enzyme linked immunoassay (ELIZA), immunoblot techniques, as well as radio-immunoassays (RIA) which preceding techniques are all available from the prior art.

A typical preferred immunoassay according to the invention comprises the following steps: (a) incubating microtitration plate wells with increasing dilutions of the biological sample to be assayed; (b) introducing in said microtitration plate wells with a given concentration of a monoclonal or polyclonal antibody according to the invention; (c) adding a labeled antibody directed against human or animal immunoglobulins, the labeling of said antibodies being, for example, an enzyme that is able to hydrolyze a substrate molecule, the substrate molecule hydrolysis inducing a change in the light absorption properties of said substrate molecule at a given wavelength, for example at 550 nm.

The present invention also concerns a diagnostic kit for the in vitro diagnosis of an infection by *Mycobacterium tuberculosis*, comprising the following elements: (a) a purified preparation of a monoclonal or a polyclonal antibody according to the invention; (b) suitable reagents allowing the detection of the antigen/antibody complexes formed, these reagents preferably carrying a label compound (a marker), or being recognized themselves by a labeled reagent; (c) optionally, a reference biological sample containing the pathogenic microorganism antigen recognized by the purified monoclonal or polyclonal antibody (positive control); (d) optionally, a reference biological sample that does not contain the pathogenic microorganism antigen recognized by the purified monoclonal or polyclonal antibody (negative control).

The present invention is also directed to a polyclonal or a monoclonal antibody directed against an immunogenic peptide according to the invention.

Polypeptides that are homologous to the initially selected polypeptide bearing at least an epitope unit are another aspect of the invention. By homologous peptide according to the present invention is meant a polypeptide containing one or several amino acid substitutions in the amino acid sequence of the initially selected polypeptide carrying an epitope unit. In the case of an amino acid substitution, one or several—consecutive or non-consecutive—amino acids are replaced by "equivalent" amino acids. The expression "equivalent" amino acid is used herein to name any amino acid that may substituted for one of the amino acids belonging to the initial polypeptide structure without decreasing the binding properties of the corresponding peptides to the monoclonal antibody that has been used to select the parent peptide and without decreasing the immunogenic properties against the specified pathogenic microorganism. Thus, an homologous polypeptide according to the present invention has the same immunological characteristics as the parent polypeptide (for example as the polypeptide of SEQ ID NO 5) with respect to the ability to confer increases resistance to infection with bacteria belonging to the tuberculosis complex.

These equivalent aminoacyles may be determined either by their structural homology with the initial aminoacyles to be replaced, by the similarity of their net charge, and by the results of the cross-immunogenicity between the parent peptides and their modified counterparts.

The peptides containing one or several "equivalent" amino acids must retain their specificity and affinity properties to the biological targets of the parent protein, as it can be assessed by a ligand binding assay or an ELIZA assay.

For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

The Different Classes of Amino Acids

| Class of Amino Acid | Examples of Amino Acids |
|---|---|
| Non Polar | A, V, L, I, P, G, F, W |
| Uncharged Polar | M, S, T, C, Y, N, Q |
| Acidic | D, E |
| Basic | K, R, H |

By modified amino acid according to the present invention is also meant the replacement of a residue in the L-form by a residue in the D-form or the replacement of a Glutamic acid (E) residue by a Pyro-glutamic acid compound. The synthesis of peptides containing at least one residue in the D-form is, for example, described by Koch et al. in 1977.

As an illustrative example, it should be mentioned the possibility to realize substitutions without a deep change in the immunogenic polypeptide binding properties of the correspondent modified peptides by replacing, for example, leucine by valine, it being understood that the reverse substitutions are permitted in the same conditions.

In order to design peptides homologous to the immunogenic polypeptides according to the present invention, one skilled in the art can also refer to the teachings of Bowie et al. (1990).

A specific, but not limitative, embodiment of a modified peptide molecule of interest according to the present invention, which consists in a peptide molecule, named herein also "pseudopeptide", which is resistant to proteolysis, is a peptide in which the —CONH— peptide bond is modified and replaced by a ($CH_2NH$) reduced bond, a (NHCO) retro inverso bond, a ($CH_2$—O) methylene-oxy bond, a ($CH_2$—S) thiomethylene bond, a ($CH_2CH_2$) carba bond, a (CO—$CH_2$) cetomethylene bond, a (CHOH—$CH_2$) hydroxyethylene bond), a (N—N) bond, a E-alcene bond or also a —CH=CH— bond.

The immunogenic polypeptides according to the present invention may be prepared in a conventional manner by peptide synthesis in liquid or solid phase by successive coupling of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merrifield may be used in particular. Alternatively, the technique described by Houbenweyl in 1974 may also be used or generally any chemical synthesis method well known by one skilled in the art, such as for example a chemical synthesis method performed with a device commercialized by the Applied Biosystems firm.

In order to produce a peptide chain using the Merrifield process, a highly porous resin polymer is used, on which the first C-terminal amino acid of the chain is fixed. This amino acid is fixed to the resin by means of its carboxyl groups and its amine function is protected, for example, by the t-butyloxycarbonyl group.

A peptide or pseudopeptide according to the present invention is advantageously combined with or contained in an heterologous structure, or polymerized in such a manner as to enhance their ability to induce a protective immune response against the pathogenic microorganism.

As a particular embodiment of the immunogenic polypeptide according to the present invention, said immunogenic polypeptide may comprise more than one epitope unit, preferably from 2 to 20 epitope units, more preferably from 2 to 15 epitope units and most preferably 3 to 8 epitope units per polypeptide molecule, usable as an active principle of a vaccine composition.

The immunogenic polypeptides of the invention that comprise more than one epitope unit are herein termed "oligomeric polypeptides". The said polymers may be obtained by the technique of Merrifield or any other conventional peptide polymer synthesis method well known by one skilled in the art.

The peptides thus obtained may be purified, for example by high performance liquid chromatography, such as reverse phase and/or cationic exchange HPLC, as described by Rougeot et al. in 1994.

As another particular embodiment of the oligomeric immunogenic polypeptides according to the present invention, the peptides or pseudopeptides are embedded within a peptidic synthetic matrix in order to form a MAP (Multi-branched Associated Peptide) type structure. Such MAP structures as well as their method of preparation are described by Tam in 1988 or in the PCT Patent Application No. WO094/28915 (Hovanessian et al.). The embedding of the peptides or pseudopeptides of therapeutic value according to the present invention within MAP type structures are expected to cause an increase in the immunogenic and/or protective properties of the initial molecules as regards to the pathogenic microorganism infection.

In order to improve the antigenic presentation of the immunogenic polypeptides according to the present invention to the immune system, said immunogenic polypeptides are presented via a MAP (Multiple Antigen Peptide) construct. This kind of presentation system is able to present more than one copy of a selected epitope unit per molecule (4 to 8 immunogenic polypeptide mimic per MAP construct molecule) embedded in a non immunogenic "carrier" molecule.

Thus, another object of the present invention consists in peptide constructs that are able to ensure an optimal presentation of the LHP immunogenic portions of the invention to the immune system.

In a specific embodiment of the peptide constructs according to the invention, the immunogenic polypeptides (the epitope units) are part of a MAP construct as defined above, such MAP construct comprising from four to eight epitope units per molecule, for example grafted on a lysine core.

Generally, an immunogenic polypeptide according to the present invention will comprise an additional T-epitope that is covalently or non-covalently combined with said polypeptide of the invention. In a preferred embodiment, the additional T-epitope is covalently linked to the immunogenic polypeptide.

Illustrative embodiments of a suitable T-cell epitope to be combined with an immunogenic peptide mimic according to the invention are, for example, the following:

hepatitis delta T-cell epitopes (Nisini et al., 1997);

a T-cell epitope from the Influenza virus (Fitzmaurice et al., 1996);

a T-cell epitope of woodchuck hepatitis virus (Menne et al., 1997);

a T-cell epitope from the rotavirus VP6 protein (Banos et al., 1997)

a T-cell epitope from the structural proteins of entroviruses, specifically from the VP2, VP3 and VP1 capsid proteins (Cello et al., 1996);

a T-cell epitope from Streptococcus mutans (Senpuku et al., 1996); or also a T-cell epitope from the VP1 capsid protein of the foot and mouth disease virus (Zamorano et al., 1995);

Preferred additional T-epitopes used according to the present invention are for example universal T-epitopes, such as tetanus toxoid or also the VP1 poliovirus capsid protein (Graham et al., 1993).

In a most preferred embodiment, the T-cell epitope used consists in a peptide comprised between amino acid in position 103 and amino acid in position 115 of the VP1 poliovirus capsid protein.

Thus, the MAP construct may comprise an additional T-epitope which is covalently linked to the immunogenic polypeptide of the MAP, the orientation being chosen depending on the immunogenic polypeptide to be used to prepare the MAP construct. Accordingly, the additional T-epitope may be located at the external end (opposite to the core) of the MAP or conversely, the additional T-epitope may be directly linked to the core of the MAP construct, thus preceding the immunogenic polypeptide which is then external to the MAP construct.

In another embodiment of the peptide constructs according to the present invention, the immunogenic polypeptide is directly coupled with a carrier molecule such as KLH (Keyhole Limpet Hemocyanin) or preferably with tetanus toxoid.

The immunogenic polypeptide according to the invention may be presented in different additional ways to the immune system.

In one specific embodiment the immunogenic polypeptide of the invention may be presented under the form of ISCOMs (Immunostimulating complexes) that are composed of Quil A (a saponin extract from Quilaja saponaria olina bark), cholesterol and phospholpids associated with the immunogenic polypeptide (Mowat et al., 1991; Morein, 1990; Kersten et al., 1995).

The immunogenic polypeptides of the invention may also be presented under the form of biodegradable microparticles (microcapsules or microspheres) such as for example lactic and glutamic acid polymers as described by Aguado et al. in 1992, also termed Poly(lactide-co-glycolide) microcapsules or microspheres.

Other microparticles used to present the LHP-derived polypeptide antigens of the invention are synthetic polymer microparticles carrying on their surface one or more immunogenic polypeptides covalently bonded to the material of the microparticles, said immunogenic polypeptide(s) each carrying one or more epitope units and being present at a density of between $10^4$ and $5.10^5$ molecules/$\mu m^2$. These microparticles have an average diameter of between about 0.25 $\mu$m and 1.5 $\mu$m, and preferentially of about 1 $\mu$m so as to be able to be presented to CD4+ T lymphocytes by phagocytic cells. Said microparticles are more particularly characterized in that the covalent bond is formed by reaction between the NH2 and/or CO groups of the immunogenic peptide mimic and the material making up the microparticle. Advantageously, such bond is created by bridging reagent as intermediate, such as for example glutaraldehyde or carbodiimide. The material of the microparticle can advantageously be a biocompatible polymer, such as acrylic polymer, for example polyacrolein or polystyrene or the poly)alpha-hydroxy acids), copolymers of lactic and glycolide acids or lactic acid polymers, said polymers being a homopolymer or hetero-or co-polymer. The above described microparticles characteristics are found in the French Patent Application No. FR 92-10,879 filed on Sep. 11, 1992 (Leclerc et al).

The immunogenic polypeptide of the invention may also be included within or absorbed onto liposomes particles, such as those described in the PCT Patent Application No. PCT/FR 95/00215 published on Aug. 31, 1995 (Riveau et al.).

The present invention is also directed to an immunogenic composition comprising an immunogenic polypeptide according to the invention, notably under the form of a MAP construct or a peptide construct as defined above, and including the oligomeric immunogenic polypeptides described hereinbefore, or also under a microparticle preparation.

The invention also pertains to a vaccine composition for immunizing human and mammal animals against a *Mycobacterium tuberculosis* infection, comprising an immunogenic composition as described above in combination with a pharmaceutically compatible excipient (such as saline buffer), optionally in combination with at least one adjuvant of the immunity such as aluminium hydroxide or a compound belonging to the muramyl peptide family.

A vaccine according to the present invention is preferably one which is capable of inducing a substantial and specific acquired immune resistance in a mouse or guinea pig against tuberculosis caused by mycobacteria belonging to the tuberculosis-complex, which acquired immune resistance corresponds to at least 20% of the protective immune resistance elicited by *Mycobacterium bovis*-BCG, as assessed by the observed reduction in mycobacterial counts from spleen, lung or other organ homogenates isolated from the mouse or guinea pig receiving a challenge infection with a virulent strain of *M. tuberculosis.*

The preferred acquired immune resistance corresponds to at least 50% of the protective immune response elicited by *M. bovis*-BCG, such as at least 60%, or even more preferred to at least 80% of the protective immune resistance elicited by *M. bovis*-BCG, such as at least 90% and advantageously 100%.

Various methods of achieving adjuvant effect for the vaccine include the use of agents such as aluminium hydroxide or phosphate (alun), commonly used as 0.05 to 0.1 percent solution in phosphate buffered saline, admixture with synthetic polymers of sugars (Carbopol) used as 0.25% solution. Another suitable adjuvant compounds consist in DDA (dimethyldioctadecylammonium bromide), as well as immune modulating substances, such as lymphokines (e.g. gamma-IFN, IL-1, IL-2 and IL-12) or also gamma-IFN inducers compounds, such as poly I:C.

Preparation of vaccines which contain polypeptides as active ingredients is generally well understood in the art, as exemplified by U.S. Pat. Nos. 4,608,251; 4,601,903; 4,599,231; 4,599,230; 4,596,792 and 4,578,770, all incorporated herein by reference.

The vaccine composition according to the present invention is advantageously prepared as injectable either as liquid solution or suspension; solid forms suitable for solution in or suspension in, liquid prior injection may also be prepared.

The active immunogenic polypeptide contained in the vaccinal composition is generally mixed with excipients which are pharmaceutically acceptable and compatible, such as for example, water saline, dextrose, glycerol, ethanol, or a combination of more than one of the above excipients.

In addition, if desired, the vaccine composition may contain minor amounts of auxiliary substances such as wetting or emulsifying agents, pH buffering agents, or adjuvants which enhance the effectiveness of the vaccines.

The vaccines are conventionally administered parentally, by injection, for example, either subcutaneously or intramuscularly. Additional formulations are suitable for other modes of administration include suppositories and, in some cases, oral formulations, which may be preferred embodiments for the development of a desired mucosal immunity.

The immunogenic polypeptide of the invention may be formulated into the vaccine as neutral or salt forms. Pharmaceutically acceptable salts include acid addition salts (formed with free amino groups of the peptide) and which are formed with inorganic acids such as, for example, hydrochloric or phosphoric acids, or such organic acids as acetic oxalic, tartaric or mandelic acid. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine or procaine.

The vaccine compositions of the invention are administered in a manner compatible with the dosage formulation, and in such amounts as will be therapeutically effective and immunogenic. The quantity to be administered depends on the subject to be treated, including, e.g., the capacity of the individual's immune system to mount an immune response.

Suitable dosage ranges are of the order of several hundred micrograms active immunogenic polypeptide with a preferred range from about 0.1 $\mu$g to 1000 $\mu$g, such as in the range from about 1 $\mu$g to 300 $\mu$g, and especially in the range from about 10 $\mu$g to 50 $\mu$g.

The dosage of the vaccine will depend on the route of administration and will vary according to the age of the patient to be vaccinated and, to a lesser degree, the size of the person to be vaccinated.

Preferably, both in the case of an immunogenic polypeptide carrying a single epitope unit and in the case of an immunogenic polypeptide carrying several epitope units, the vaccine composition is administered to humans in the range from 0.1 to 1 µg immunogenic polypeptide per kilogram patient's body weight, preferably in the range from 0.5 µg/kg of body weight, this representing a single vaccinal dose for a given administration.

In the case of patients affected with immunological disorders, such as, for example, immunodepressed patients, each injected dose preferably contains half the weight quantity of the immunogenic polypeptide contained in a dose for a healthy patient.

In many instances, it will be necessary to proceed with multiple administrations of the vaccine composition according to the present invention, usually not exceeding six administrations, more usually not exceeding four vaccinations, and preferably one or more, usually at least about three administrations. The administrations will normally be at from two to twelve week intervals, more usually from three to five week intervals. Periodic boosters at intervals of 1–5 years, usually three years, will be desirable to maintain the desired levels of protective immunity.

Preferably, the vaccine composition is administered several times. As an illustrative example, three vaccinal doses as defined herein above are respectively administered to the patient at time t0, at time t0+1 month and at time t0+12 months.

Alternatively, three vaccinal doses are respectively administered at time t0, at time t0+1 month and at time t0+6 months.

The course of the immunization may be followed by in vitro proliferation assays of PBL (peripheral blood lymphocytes) co-cultured with the immunogenic polypeptide of the invention, and especially by measuring the levels of gamma-IFN released from the primed lymphocytes. The assays may be performed using conventional labels, such as radionuclides, enzymes or fluorescent compounds. These techniques are well known from one skilled in the art and found notably in U.S. Pat. Nos. 3,731,932; 4,174,384 and 3,949,064, which are herein incorporated by reference.

As described above, a measurement of the effect of the polypeptides in the vaccine compositions according to the present invention may be to assess the gamma-IFN released from memory T-lymphocytes. The stronger immune response the more gamma-IFN will be released, accordingly, a vaccine composition according to the invention comprises a polypeptide capable of releasing from the memory T-lymphocytes at least 15000 pg/ml, such as 2000 pg/ml, preferably 3000 pg/ml gamma-IFN, in the above described in vitro assays.

In mice, that are administered with a dose comparable to the dose used in humans, the antibody production is assayed after recovering the immune serum and revealing the immune complex formed between the antibodies present in the serum samples and the immunogenic polypeptide contained in the vaccine composition, using the usual methods well known from one skilled in the art.

The immunogenic polypeptides used in the vaccinal strategy according to the present invention may also be obtained using genetic engineering methods. One skilled in the art will refer to the known sequence of DNA insert that expresses a specific antigenic portion (epitope unit) of an immunogenic polypeptide of the invention and also to the general literature to determine which appropriate codons may be used to synthesize the desired peptide.

There is no need to say that the expression of the polynucleotide that encodes the immunogenic polypeptide of interest may be optimized, according to the organism in which the sequence has to be expressed and the specific codon usage of this organism (mammal, plant, bacteria, etc.). For bacteria and plant, respectively, the general codon usages may be found in the European Patent Application No. EP-0359472 (Mycogen).

As an alternative embodiment, the epitope unit of the immunogenic polypeptide contained in a vaccine composition according to the present invention is recombinantly expressed as a part of longer polypeptide that serves as a carrier molecule.

Specifically, the polynucleotide coding for the immunogenic polypeptide of the invention, for example a polypeptide having an amino acid length between 100 and 200 amino acid residues, is inserted at least one permissive site of the polynucleotide coding for the Bordetella cyaA adenylate cyclase, for example at a nucleotide position located between amino acids 235 and 236 of the Bordetella adenylate cyclase. Such a technique is fully described in U.S. Pat. No. 5,503,829 granted on Apr. 2, 1996 (Leclerc et al.).

In another embodiment of the vaccine composition according to the present invention, the nucleotide sequence coding for the desired immunogenic polypeptide carrying one or more epitope units is inserted in the nucleic sequence coding for a surface protein of *Haemophilus influenza,* such as described in the PCT Application No. PCT/US 96/17698 (the Research Foundation of State University of New York), which is herein incorporated by reference.

In a further embodiment of the vaccine composition according to the present invention, the latter is based upon a live recombinant cell host expressing the entire LHP polypeptide of sequence SEQ ID NO 5 or alternatively a polypeptide containing an immunogenic portion of LHP according to the invention or also an oligomeric immunogenic LHP-derived polypeptide such as those described hereinbefore.

The microorganism in the vaccine may be a bacterium such as bacteria selected from the group consisting of the genera Mycobacterium, Salmonella, Pseudomonas or *E. coli.*

A preferred embodiment of a vaccine composition containing a live recombinant cell host according to the invention consists in a *Mycobacterium bovis*-BCG strain which has been transformed with a polynucleotide encoding the entire LHP polypeptide or alternatively a polypeptide containing an immunogenic portion of LHP or also an oligomeric immunogenic LHP-derived polypeptide.

An advantageous method used to transform a *Mycobacterium bovis*-BCG strain with a polynucleotide coding for an immunogenic polypeptide according to the present invention consists in introducing the polynucleotide of interest via an allelic exchange event (homologous recombination involving a double cross-over) or via an homologous recombination involving a single cross-over, using a recombinant vector.

Such a recombinant vector carries the gene encoding the immunogenic polypeptide or interest which has been introduced in a polynucleotide counterpart of a gene not essential for the growth of *Mycobacterium bovis*-BCG on the vector, such as for example the urease gene. Said vector carries advantageously also a conditional lethal selection marker such as SacB gene. The relevant transformation methods and vectors are fully described by Reyrat et al. (1995) or Pelicic et al. (1996).

Another embodiment of the live vaccine compositions according to the present invention consists in compositions containing live mycobacteria, and preferably live *Mycobac-* terium bovis-BCG or mutant derived from *Mycobacterium tuberculosis* or *Mycobacterium bovis*-BCG transformed with a recombinant vector containing an antigenic protein placed under the control of a regulatory polynucleotide according to the present invention.

The live vaccine compositions of the invention are administered in a manner compatible with the dosage formulation, and in such amount as will be therapeutically effective and immunogenic. The quantity to be administered depends on the subject to be treated, including, e.g., the capacity of the individual's immune system to induce an immune response.

Suitable dosage ranges are of the order of $10^4$ to $10^6$ cfu (colony forming units) at an attenuated recombinant mycobacteria concentration of about $10^6$ cfu/mg. Most preferably, the effective dose is about $10^5$ cfu.

The dosage of the vaccine will depend on the route of administration and will vary according to the age of the patient to be vaccinated and, to a lesser degree, the size of the person to be vaccinated. Most preferably, the vaccine composition according to the present invention is administered via an intradermal route and in a single boost.

In the case of patients affected with immunological disorders, such as for example immunodepressed patients, each injected dose preferably contains half the weight quantity of the attenuated mycobacteria contained in a dose for a healthy patient.

In the case of neonates, the dose will be four times less than for an adult, and in case of young children (4–6 years old), the dose will be half the dose used for an adult healthy patient.

In some instances, it will be necessary to proceed with multiple administrations of the vaccine composition according to the present invention, usually not exceeding six administrations, more usually not exceeding four vaccinations, and preferably one or more, usually at least about three administrations. The administrations will normally be at from two to twelve week intervals, more usually from three to five week intervals. Periodic boosters at intervals of 1–5 years, usually three years, will be desirable to maintain the desired levels of protective immunity.

Immunization by DNA-based vaccines has been the object of several studies since the beginning of the 1990s. A DNA-based vaccine involves the transfer of a gene or at least a portion of a gene, by direct or indirect means, such that the protein subsequently produced acts as an antigen and induces a humoral-and/or cellular mediated immunological response.

Ulmer et al.—Science, 259: 1745–1749 [1993] obtained protection against the influenza virus by induction of the cytotoxic T-lymphocytes through injection of a plasmid coding for an influenza A nucleoprotein into the quadriceps of mice. The plasmid used carries either the Rous sarcoma virus promoter or the cytomegalo virus promoter.

Raz et al.—Proc. Natl. Acad. Sci. USA 90: 45234527 [1993] injected vectors comprising the Rous sarcoma virus promoter and a gene coding for interleukin-2, interleukin4, or the β1-type transforming growth factor (TFG-β1). The humoral and cell-mediated immune response of the mice to which these plasmids have been intramuscularly administered are improved.

To Wang et al.—Proc. Natl. Acad. Sci. USA 90: 4156–5160 [1993] injected a plasmid carrying a gene coding for the envelope protein of the HIV-1 virus into mice muscles. The plasmid injection was preceded by treatment with bupivacaine in the same area of the muscle. The authors demonstrated the presence of antibodies capable of neutralizing the HIV-1 virus infection. However, the DNA was injected twice a week for a total of four injections.

Davis et al. (Compte-Rendu du 28eme Congres Europeen sur le muscle, Bielefeld, Germany, Sep. 21–25 1992) injected plasmids carrying a luciferase or β-galactosidase gene by pre-treating the muscle with sucrose or a cardiotoxin. The authors observed the expression of luciferase or β-galactosidase.

More recently, an article published in Science et Avenir (September 1993: 22–25) indicates that Whalen and Davis succeeded in immunizing mice against the hepatitis B virus by injecting pure DNA from the virus into their muscles. An initial injection of snake venom toxin, followed 5 to 10 days later by a DNA injection, is generally described. However, the authors specify that this method is not practical.

These studies were preceded by other experiments in which various DNAs were injected, in particular into muscle tissues. For example, U.S. Pat. Nos. 5,589,466 and 5,580,859 (VICAL INC) and the International Application PCT/US90/01515 (published under No. WO/90/11092) disclose various plasmid constructions which can be injected in particular into muscle tissues for the treatment of muscular dystrophy. However, this later document specifies that DNA is preferentially injected in liposomes.

Additionally, Canadian Patent CA 362 96630 (published under No. 1,169,793) discloses the intramuscular injection of liposomes containing DNA coding, in particular, for HBs or HBc antigens. The results described in this patent mention the HBs antigen expression. The presence of anti-HBs antibodies was not investigated.

International Application PCT/FR92/00898 (published under No. WO93/06223) discloses viral vectors which can be conveyed to target cells by blood. These vectors are recognized by the cell receptors, such as the muscle cells, and can be used in the treatment of muscular dystrophy or thrombosis.

The present invention relates to a composition capable of inducing an immune response, and more particularly, an humoral or/and a cytotoxic response comprising a nucleotide sequence expressed in muscle cells. The nucleotide sequence comprises a gene or complementary DNA coding for at least a portion of nucleotidic sequence comprised in the pIPX61 insert preferably the lhp polynucleotide coding region and a promoter and/or regulatory region allowing for the expression of the gene or complementary DNA in the muscle cells.

The invention further relates to the vector, which serves as a vehicle for the gene or complementary DNA coding for at least lhp polynucleotide coding region and a promoter allowing for the expression of the gene or cDNA which is administered to an individual to be immunized.

The present invention will be fully illustrated by the examples described below, although the scope of the invention cannot in any way be limited to these embodiments.

EXAMPLES

Example 1

Genetic Organization Upstream from the *M. tuberculosis* or flC Gene

To isolate potential promoter region, the inventors have cloned the 1.1 kb DNA sequence upstream from the *M. tuberculosis* or flC gene. A 150 bp DNA fragment covering the first half of the or flC gene was obtained by digestion of the plasmid pAA249 with EcoRI/PstI, radioactively labeled and used to probe a cosmid library of *Mycobacterium tuberculosis* strain H37Rv by colony hybridization (Sambrook et al., 1989). A 1.1 kb PstI restriction fragment shared by three strongly hybridizing cosmids, was transferred to pBluescript II KS+to give pIPX 61 (FIG. 2).

Double-stranded DNA sequencing revealed perfect nucleotide identity between the 1069 bp insert of pIPX61 and its counterpart in *M. bovis* RD1 (Maheiras et al., 1996). It included a 285 bp open reading frame preceded by a potential ribosomal binding site (AGAGA) in the same transcriptional orientation as or flC (FIG. 5A). This ORF was designated lhp (L45 homologous protein) since its deduced product shared 40% peptide identity with the *M. leprae* L45 seroreactive antigen (FIG. 5B). L45 seroreactive antigen is strongly recognized by sera from lepromatous leprosy patients (Sathish et al., 1990) but its function is currently unknown. lhp was not annotated in the *M. bovis* RD1 sequence published by Maheriras et al. (Maheiras et al., 1996) and overlaps with the 3' end of the predicted but uncharacterized or flB gene.

Example 2

Analysis of lhp- and or flC-lacZ Gene Fusions

To investigate promoter activity, the inventors have constructed translational fusions between or flC, lhp and the lacZ reporter gene, or flC and lhp were inserted into promoter probe vectors of the pJEM series (Timm et al., 1994), out- or in frame with regard to lacZ. The resulting plasmids were named pIPX15, pIPX16 and pIPX46, pIPX47 respectively (FIG. 2). These constructs were introduced by electroporation in *M. smegmatis* $mc^2$ 155 and §-galactosidase activity was assayed in bacterial cell extracts. Strong §-galactosidase activity was detected in extracts of cells carrying in frame fusions (pIPX16 and pIPX47) but not in extracts of cells carrying out-of-frame fusions (pIPX15 and pIPX46). Thus (i) lhp is expressed and translated (ii) there is a mycobacterial promoter activity somewhere in the 900 bp upstream from the or flC start codon. The differences in levels of §-galactosidase activity produced from pIPX16 and pIPX47 may reflect differences in the stability of lacZ fusion proteins. Alternatively, this may be attributable to differences in the efficiency of lhp and or flC translation signals. In that respect, a long (A+G)-rich stretch upstream from the or flC ATG and overlapping the predicted ribosomal binding site may potentially alter the translation of or flC-lacZ.

Example 3

Mapping of the lhp/or flC Promoter Activity

The inventors have performed primer extension experiments to map the site(s) of lhp/or flC transcription initiation. Total RNA was extracted (Bashyam et al., 1994) from *M. tuberculosis* and *M. smegmatis* $mc^2155$ transformed with pIPX16. By walking upstream from the start codon, we identified one major and two secondary transcriptional start sites in *M. tuberculosis* (FIG. 6A). The sites are close together within a region of 30 bp about 430 nucleotides upstream from the or flC ATG start codon. The (A+T)-rich [TAATGA] region may correspond to the −10 hexcamer motif identified in promoters of other bacterial genera. The corresponding −35 region contains two tandem repeats of a 18 nucleotide motif extending from positions −25 to −60 (FIG. 6B). The significance of this organization is unknown but may serve a regulatory function (Collado-Vides et al., 1991). The positions of the transcriptional start sites detected in *M. tuberculosis* are consistent with lhp and or flC being cotranscribed.

Surprisingly, the transcription start sites detected with RNA extracted from *M. smegmatis* $mc^2155$ [pIPX16] differed from those in *M. tuberculosis* (FIG. 6C). The major *M. smegmatis* start site was immediately downstream from the predicted lhp ribosome binding site (FIG. 5A). This suggests that the genuine lhp-or flC promoter may not be recognized and that alternative transcription signals are used in *M. smegmatis*. To test this, a 480 bp DNA fragment encompassing the transcription start sites identified in *M. tuberculosis* was inserted into the vector pJEM15, creating a transcriptional fusion with lacZ. The resulting plasmid (pIPX18) was introduced into *M. bovis* BCG and lacZ. The resulting plasmid (pIPX18) was introduced into *M. bovis* BCG and lacZ activity was detected by the appearance of blue colonies on 7H10 X-Gal indicator plates. In contrast, no activity was observed with colonies of *M. smegmatis* $mc^2155$ [pIPX18] grown on the same plates. The absence of significant galactosidase activity in $mc^2155$[pIPX18] was confirmed by standard galactosidase assays (FIG. 2). This data suggests that correct expression of lhp-or flC required facto (s) absent from or not functional in *M. smegmatis.*

Example 4 lhp/or flC are Organized as an Operon

To confirm that lhp and or flC belong to the same transcriptional unit, the inventors used the ESA-A probe (see FIG. 2) for Northern blotting hybridization with total *M. tuberculosis* RNA. A strong hybridization signal migrating at about 800 bp (estimated using RNA molecular weight standards) was detected (FIG. 7, lanes 1 and 2). Moreover, comparable amounts of this transcript were detected in early (day 5) and late (day 16) cultures (FIG. 7, lanes 3 to 6). Consequently the lhp-or flC transcript appears to be produced in *M. tuberculosis* from a constitutive high level promoter, and/or alternatively, is very stable. In view of the position of the +1 sites, a transcript of 800 bp covers both lhp and or flC. Furthermore, there is a structure similar to a Rho-independent transcription terminator, 790 bp downstream from the lhp/or flC major transcriptional start site.

Example 5

Construction of the pIPX30 Expression/Tagging Vector

The design of the pIPX30 was carried out in two steps. First, we constructed a small sized *E. coli*—mycobacteria shuttle plasmid harboring a convenient multiple cloning site and a selectable marker gene conferring resistance to kanamycin. The PstI fragment from pUC4K together with the NdeI/BsaI-digested pUC18 were blunted with phage T4 polymerase (Amersham) and ligated to each other. The resulting plasmid designated pPV8 was digested by StuI and ligated to the EcorRV/HpaI fragment from pAL5000 to give pPV24. The pPV24 plasmid is a multipurpose shuttle cloning vector harboring four unique restriction sites (KpnI, BamHI, XbaI, PstI). It allows alpha complementation and blue/white selection of recombinants in *E. coli.*

In a second time, a fragment containing the ESAT-6 promoter region, was amplified by PCR under standard condition using XP1 ( ) and XP2 ( ) oligonucleotides. A linker fragment was generated by PCR-driven in vitro extension and amplification of the two overlapping oligonucleotides XL1 ( ) and XL2 ( ). Since the promoter and linker fragments carried a 12 bp overlapping region, they were recombined in vitro by PCR amplification using the XP1 and XL2 oligonucleotides. This PCR-tailored fragment was inserted in pPV24 previously digested with KpnI/PstI and blunted with T4 polymerase, resulting in the plasmid pIPX30. As presented FIG. 1, the pIPX30 expression cassette is composed of (i) a Shine Dalgarno motif functional in mycobacteria (ii) a translation initiation codon followed by three unique cloning sites, allowing gene fusions with a stretch of DNA coding for six histidine (iii) two translational termination codons and the ESAT-6 transcription terminator.

2.2. pIPX30 Promotes High Level Express of Galactosidase in Mycobacteria

To characterize this novel express vector, a truncated lacZ reporter gene, generated by Asp718/PstI digestion of promoter-probe plasmid pJEM13, was inserted into the corresponding sites of pIPX30. In the resulting plasmid designated pIPX34, the lacZ gene is in frame with regard to the pIPX30 ATG initiation codon. When introduced into *M. smegmatis* mc²155, pIPX34 produced a high level of galactosidase activity (FIG. 2). This level of galactosidase activity is comparable to the one obtained in pJN30 extracts, where lacZ is under the control of the strong pBlaF* promoter of *Mycobacterium fortuitum*. When transformed in *Mycobacterium bovis* BCG, the pIPX34 construct resulted in dark blue colonies in presence of the §-galactosidase X-gal chromogenic substrate. These observations indicated that the combination of promoter/expression cassette used in pIPX30 is functional in representative members of fast- and slow-growing mycobacteria.

Example 6

Expression and Immunodetection of DES (His6) in *M. smegmatis*.

To validate pIPX30 as an expression/tagging vector, we expressed in this system the DES antigen of *M tuberculosis*. The DES gene was recently cloned from *Mycobacterium tuberculosis* and encodes DES, a protein sharing conserved motifs characteristic of the class II diiron-oxoprotein family. DES is putative Δ-9 (delta 9) desaturase and could potentially be involved in the biosynthesis of mycobacterial lipids and mycolic acids. Moreover, DES is strongly recognized by sera from tuberculosis patients and represent a potential diagnostic reagent. To express DES in a mycobacterial context, the model *M. smegmatis* was chosen as a host because it is innocuous and can be grown to high cell density (up to $10^8$ CFU/ml) in overnight broth cultures. Oligonucleotides JD 15 (5'-CCCGGATCCTCAGCCAAGCTGAC CGACCTG-3') (SEQ ID NO;18) and JD16 (5'-GCCGGTACCACGACGGCTCATCGCCAGTTTGCC-3') (SEQ ID NO;19) were used to amplify by PCR the DES coding region cloned in plasmid pBS-DES. The resulting PCR fragment was digested with BAMHI and KpnI and cloned into the corresponding sites of pIPX30 to give pIPX30-DES. Protein extracts corresponding to the bacterial cell sonicate were prepared from *M. smegmatis* harboring pIPX30 or pIPX30-DES, and analyzed by Western blotting using anti-DES mouse polyclonal serum. As reported FIG. 3A, a protein band migrating at about 38 kDa, was detected specifically in *M. smegmatis* transformed with pIPX34 plasmid but not in extracts corresponding to the pIPX30 control vector. An additional 36 kDa band detected in both protein extracts, was attributed to the endogenous *M. smegmatis* DES protein or alternatively to a molecule cross reacting with the anti-DES mouse serum. The same results (FIG. 3B) were obtained with a commercially available monoclonal antibody directed against the (His)6 peptide, supporting the presence of six histidine at the carboxyl terminus of DES.

Example 7

Identification of LHP Polypeptide in Short Term Culture Filtrate (ST-CF)

ST-CF was produced as previously described (Anderson. et al., 1991). Briefly, *M. tuberculosis* ($8 \times 10^6$ CFU/ml) were grown in modified Sauton medium on an orbital shaker for 7 days. The culture supernatants were sterile-filtrated and concentrated on an Amicon YM3 membrane (Amicon, Danvers, Mass.). The ORFX protein was purified from ST-CF by preparative SDS-PAGE using the Prepcell system (BioRad, Richmond, Calif.). 1 ml containing 8 mg of ST-CF was applied on a matrix of 16% polyacrylamide and separation was performed under an electrical gradient for 22 hours. 3 ml fractions were collected and analyzed on silver-stained SDS-PAGE. 3 ml of the fractions containing the ORFX protein was concentrated in the presence of 0.1 SDS in a Centricon-3 unit (Amicon) followed by acetone precipitation. The precipitate was redissolved in Tricine SDS-PAGE gel (Novex, San Diego, USA). After electrophoresis the gel was blotted to Problott PVDF membrane (Applied Biosystems, Foster City, Calif.) by semidry electroblotting in 10 mM CAPS, 10% methanol, pH 11. The PVDF membrane was stained with 0.1% Coomassie R-250 in 40% methanol, 1% acetid acid, and destained in 50% methanol. The band of interest was excised and subjected to N-terminal sequence analysis by automated Edman degradation using a Procise 494 sequencer (Applied Biosystems) as described by the manufacturer.

By N-terminal amino acid sequencing, the inventors have obtained the following sequence. A-E-M-K-T-D-A-A-T-L-X-Q-E-A-G (SEQ ID NO:20), wherein X represents any amino acid, said sequence corresponding to the N-terminal sequence of LHP, the methionine residue located at the NH2-terminal position having been naturally removed by the bacterial enzymatic machinery.

As it appears from the teachings of the Specification, the invention is not limited in scope to one or several of the above detailed embodiments; the present invention also embraces all the alternatives that can be performed by one skilled in the same technical field, without deviating from the subject or from the scope of the instant invention.

REFERENCES

1. Aguado et al., Immuno Biol., 184:113–125.
2. Andersen, P., A. B. Andersen, Sorensen, A. L. and S. Nagai. 1995. Recall of long-lived immunity to *Mycobacterium tuberculosis* infection in mice. J. Immunol. 154:3359–3372.
3. Andersen, P., D. Askgaard, L. Ljungqvist, W. M. Bentzon, and I. Heron. (1991) Infect. Immun. 59:1905–1910
4. Barany, F., 1911, Proc. Natl. Acad. Sci, USA, 88:189–193.
5. Bashyam, M. D. and A. K. Tyagi. 1994. An efficient and high-yielding method for isolation of RNA from mycobacteria. BioTechniques 17:834–836.
6. Bashyam, M. D., Kaushal, D., Dasgupta, K. K. and A. K. Tyagi. 1996. A study of the mycobacterial transcriptional apparatus: Identification of novel features in promoter elements. J. Bacteriol 178:4847–4853.
7. Bengard A. et al., 1994, In: Tuberculosis: Pathogenesis, Protection and Control, Barry R. Bloom, Ed., American Society for Microbiology, Washington, D.C. 20005, Chapter 21, 307–332.
8. Berthet, F.-X., Rauzier, J., Lim, E. M., Philipp, W., Giequel, B. and D. Portnoï. 1995. Characterization of the *Mycobacterium tuberculosis* erp gene encoding a potential cell surface protein with repetitive structures. Microbiology 141:2123–2130.
9. Bowie J. U. et al., 1990, Science, 47:1306–1310.
10. Burg J. L. et al., 1996, Mol. And Cell. Probes, 10:257–271.
11. Chu B. C. F. et al., 1986, Nucleic Acids Res., 14:5591–5603.
12. Collado-Vides, J., Magasanik, B. and J. D. Gralla. 1991. Control site location and transcriptional regulation in *Escherichia coli*. Microbiol. Rev. 55:371–394.
13. Collins, D. M. 1996. In search of tuberculosis virulence genes. Trends Microbiol. 4:426430.
14. Collins, D. M., Kawakami, R. P., De Lisle, G. W., Pascopella, L., Bloom, B. R. and W. Jacobs Jr. 1995. Mutation of the principal sigma factor causes loss of virulence in a strain of the *Mycobacterium tuberculosis* complex. Proc. Natl. Acad. Sci. USA 92:8036–8040.
15. Duck P. et al., 1990, Biotechniques, 9:142–147.
16. Garbe T. et al., 1993, Infect. Immun., 61(1):260–267.
17. Goldman et al., 1986, Ann. Rev. Biophys. Chem., 15:321–353.
18. Guateli J. C. et al., 1990, Proc. Natl. Acad. Sci. USA, 87:1874–1878.
19. Harboe, M., Oettinger, T., Gotten Wiker, H., Rosenkrands, I. and P. Andersen. 1996. Evidence for occurrence of the ESAT-6 protein in *Mycobacterium tuberculosis* and virulent *Mycobacterium bovis* and for its absence in *Mycobacterium bovis*-BCG. Infect. Immun. 64:16–22.
20. Harris D. P. et al., 1994, Infect. Immun., 62(7): 2963–2972.
21. Herrmann J. L. et al., 1996, The EMBO J., 15(14): 3547–3554.
22. Houbenweyl, 1974, in Meuthode der Organischen Chemie, E. Wunsch Ed., Volume 15-I et 15 II, Thieme, Stuttgart.
23. Kenney, T. J. and G. Churchward. 1996. Genetic analysis of the *Mycobacterium smegmatis* rpsL promoter. J. Bacteriol. 178:3564–3571.
24. Kersten G. F. et al., 1995, Biochem. Biophys. Acta, 1241:117–138.
25. Kievitis T. et al., 1991, J. Virol. Methods, 35:273–286.
26. Kremer, L., Baulard, A., Estaquier, J., Content, J., Capron, A. and C. Locht. 1995. Analysis of the *Mycobacterium tuberculosis* antigen 85A promoter region. J. Bacteriol. 177:642–653.
27. Kwoh D. Y. et al., 1989, Proc. Natl. Acad. Sci. USA, 86:1173–1177.
28. Kyte et al., 1982, J. Mol. Biol., 157:105–132
29. Landegren U. et al., 1988, Science, 241:1077–1080.
30. Lizardi P. M. et al., 1988, Bio Technology, 6:1197–1202.
31. Maheiras, G. G., Sabo, P. J., Hickey, M. J., Devinder, C. S. and C. K. Stover. 1996. Molecular analysis of genetic differences between *Mycobacterium bovis*-BCG and virulent *M. bovis* J. Bacteriol. 178:1274–1284.
32. Matthews J. A. et al., 1988, Anal. Biochem., 169:1–25.
33. Merrifield, 1963, J. Am. Chem. Soc., 85:2149–2154.
34. Miele E. A. et al., 1983, J. Mol. Biol., 171:281–295.
35. Morein b., 1990, Immunol. Letters, 25:281–283.
36. Mowat A. M. et al., 1991, Immunol. Today, 12:383–385.
37. Pelicic V. et al., 1996, Mol. Microbiol., 20(5):919–925.
38. Quinn, F. D., Newmann, G. W. and c. H. King. 1996. Virulence determinant of *Mycobacterium tuberculosis* in Tuberculosis Ed. T. Shinnik, Springer verlag.
39. Reyrat J-M. et al., 1995, Proc. Natl. Acad. Sci. USA, 92:8768–8772.
40. Rougeot, C., I. Rosinski-Chupin, e. Njamkepo, and F. Rougeon. Eur. J. Biochem. 219(3):765–773, 1994.
41. Sambrook, J. Fritsch, E. F., and T. Maniatis. 1989. Molecular cloning: a laboratory manual. 2ed. Cold Spring Harbor Laboratory, Cold Spring Harbor, N.Y.
42. Sanchez-Pescador R., 1988, J. Clin. Microbiol., 26(10): 1934–1938.
43. Sathish, M., Esser, R. E., Tholle, J. E. R. and J. E. Clark-Curtiss. 1990. Identification and characterization of antigenic determinants of *Mycobacterium leprae* that react with antibodies in sera of leprosy patients. Infect. Immun. 58:1327–1336.
44. Segev D., 1992, in <<Non-radioactive Labeling and Detection of Biomolecules >>. Kessler C. Springer Verlag, Berlin, New York, 197–205.
45. Sørensen, A. L., Nagai, S., Houen, G., Andersen, P. and A. B. Andersen. 1995. Purification and characterization of a low-molecular-mass T-cell antigen secreted by *Mycobacterium tuberculosis* Infect. Immun. 63:1710–1717.
46. Spargo C. A. et al., 1996, Mol. and Cell. Probes, 10:247–256
47. Stone B. B. et al., 1996, Mol. and Cell. Probes, 10:359–370.
48. Tam J. P., 1988, Proc. Natl. Acad. Sci., 85:5409–5413.
49. Timm, J., Lim, E. M. and B. Giequel. 1994. *Escherichia coli*-mycobacteria shuttle vectors for operon and gene fusions to lacZ: the pJEM series. J. Bacteriol. 176:6749–6753.
50. Urdea M. S. et al., 1991, Nucleic Acids Symp. Ser., 24:197–200.
51. Urdea M. S., 1988, Nucleic Acids Research, 11:4937–4957.
52. Wabiko et al., 1986, DNA, 5(4):305–314.
53. Walker G. T. et al., 1992, Nucleic Acids Res., 20:1691–1696.

Annex I

DNA sequence    1069 b.p.    CTGCAGCAGGTG ... aacgcgctgcag    linear

Positions of Restriction Endonucleases sites (unique sites underlined)

```
                              Msp I
                              Hpa II
                    ScrF I    Cfr10 I
                    EcoR II   SgrA I
         Mae II     Dsa V     BspW I
BspM I              BstN I    Nla IV
Fnu4H I  Aha II     BstK I    Ban I
Bbv I    Aat II     BspW I    Fnu4H I                          HinP I
Sfe I    Mae III    Bgl I     BspW I    Fnu4H I                Hha I
Pst I    Hph I                BspW I    Fnu4H I      Mnl I     Fnu4H I
| |  |   || ||      ||        | |||||   | |         |         | || BstU I
CTGCAGCAGGTGACGTCGTTGTTCAGCCAGGTGGGCGGCACCGGCGGCGGCAACCCAGCCGACGAGGAAGCCGCGCAGAT  80
GACGTCGTCCACTGCAGCAACAAGTCGGTCCACCCGCCGTGGCCGCCGCCGTTGGGTCGGCTGCTCCTTCGGCGCGTCTA
| |  |   || ||      ||  •     | |||||   | •        •         | ||  •
1    9              26        35                             64     72
1    10             26        35        47                   70
   3                27        37                                    73
   3  6             27        37                                    73
         12         27        38
         12         27        39
             13     27        40
                              41
                              41
```

```
                                                    Sau96 I
                                                    Nla IV
                                                    Hae III  Fau I       BspW I
                              NspB II               EcoO109 I            Hae III    BstU I
BspW I                        Fok I       SauJA I            BstU I      Sau96 I    HinP I
Bgl I              Bsr I      Xcm I       Mbo I              HinP I Fau I           Hha I
Hae III  Nla IV               PflM I      Dpn II             Hha I BstU I           BssH II
Sau96 I  Ban I     Taq I      BsiY I      Dpn I     BsiY I         HinP I  Fnu4H I
|||      |        |     |      ||          ||    || ||     |||    ||| |||  | ||    Bbv I
GGGCCTGCTCGGCACCAGTCCGCTGTCGAACCATCCGCTGGCTGGTGGATCAGGCCCCAGCGCGGGCGCGGGCCTGCTGC  160
CCCGGACGAGCCGTGGTCAGGCGACAGCTTGGTAGGCGACCGACCACTAGTCCGGGGTCGCGCCCGCGCCCGGACGACG
|||      •|       |       •|    | •      || • || ||    |||   ||| |||        | ||
81       91      100       111          127      135              146              156
82       91               106           128      136              146              156
83             95                       128                             147         159
83                                      128              140            148         159
                                        128              140   141      150         159
                                                 112     115            141                  160
                                                         115
                                                                  132
                                                                  133   142         152
                                                                  133
                                                                  133
```

```
                    BspM I
                    HinP I
                    Hha I
                    ScrF I
                    EcoR II
         Ple I      EcoN I                                            Taq I
         Hinf I     Dsa V                                             SauJA I
BstU I              BstN I                                            Mbo I
HinP I              BstK I                                Alu I
Hha I               BsiY I        Fau I     NspB II       Pvu II      Msp I
| |                 | |    Hinc II  Fnu4H I Dde I  Dpn II BsmA I Dpn I Hpa II
                                                                      Cfr10 I
||           | •|        |         ||      | |||   | |         ||
GCGCGGAGTCGCTACCTGGGCAGGTGGGTCGTTGACCCGGCACGCCGCTGATGTCTCAGCTGATCGAAAAGCCGGTTGCC  240
CGCGCCTCAGCGATGGACCGTCCACCCAGCAACTGGGCGTGCGGCGACTACAGAGTCGACTAGCTTTTCGGCCAACGG
||           |  •|       |         ||  • | |||  • | |         ||   •
161          175        192        204     213    222                  231
161          175                    197     205    215    222          232
162          175                                   217                 232
     166     175                                   217
     166     175                                   218
             175
             175                                          222
                    179                                   222
                    179                                          224
                    181
```

```
                                          Fnu4H I
                                          HinP I         ScrF I
                                          Hha I          Nci I
                              Sau3A I     Nla IV         Msp I         ScrF I
                  Fnu4H I     Mbo I       Nar I          Hpa II        EcoR II
                  BspW I      Dpn II      Kas I          Dsa V         Dsa V
                  Msp I       Msp I       Hae II         Sau96 I       BstN I
             Nae I  Fnu4H I   Alw I       Fhe I          Ava II        BstK I
      Hph I  Hpa II Fnu4H I               Bbe I          Nla IV        BsaJ I
  Mnl I SfaN I      Bbv I  Hpa II         Ban I    Msp I  BstK I       Hae III
  BsaJ I  Cfr10 I   Bbv I  Dpn I          Aha II   Hpa II Bcn I        Sau96 I
  |   |   |  ||  |   | •|    | ||•          ||     ||     ||    •       ||| •
  CCCTCGGTGATGCCGGCGGCTGCTGCCGGATCGTCGGCGACGGGTGGCGCCGCTCCGGTGGGTCCGGGAGCGATGGGCCA  320
  GGGAGCCACTACGGCCGCCGACGACGGCCTAGCAGCCGCTGCCCACCGCGGCGAGGCCACCCAGGCCCTCGCTACCCGGT
  |   |   | •||   | •|    | ||•     •        ||•     ||      ||   •      ||| •
  242     252       262   269              286     295     304           315
  242    249      259    266               286     295     304           316
       246    253     262                  286            300            318
            252    259       268           286                 301       318
               253       266               286                 301       318
                    256        269         286                     304   318
                    256        269         286                     304   318
                               269         286                     304   318
                                           287                     304
                                           287                     304
                                           289
```

```
                         ScrF I
                         Nci I
                         Msp I
                         Hpa II           BspW I
                         Dsa V            Nla IV
                         BstK I           Ban I
                         Bcn I            Msp I
                  Xcm I                   Hpa II
                  ScrF I                  Nae I
                  EcoR II                 Cfr10 I
          Nla IV  Hae III                 BspW I
  HinP I  Fnu4H I Dsa V       HinP I      HinP I        Mbo II
  Hha I   Msp I   BstN I      Hha I       Hha I         Bbs I
  Fsp I   Hpa II  BstK I      BstU I      BstU I        Mbo II    Mnl I
  ||   •  |  |    |  | •      || ||  ||   ||     •       | •          |
  GGGTGCGCAATCCGGCGGCTCCACCAGGCCGGGTCTGGTCGCGCCGGCACCGCTCGCGCAGGAGCGTGAAGAAGACGACG  400
  CCCACGCGTTAGGCCGCCGAGGTGGTCCGGCCCAGACCAGCGCGGCCGTGGCGAGCGCGTCCTCGCACTTCTTCTGCTGC
  ||   •  |  |•   |  | •      || ||  ||   ||     •       |•|          |
  324     332    344          360         375           388           400
  325     332    344          361         376           391
  325         335 344          361        376           391
                  337     347
                         344     363
                         344     363
                         344     363
                                 364
                                 349    364
                                 349        366
                                 349        366
                                 349            367
                                 349
                                 349
                                 349
```

```
                                                                ScrF I
                                                                Nci I
                                                                Msp I
                                                                Hpa II
                                                                Dsa V
                                                                Xma I
                                                                Sma I
                                                                ScrF I
                                                   BspW I
                                                     Bgl I      Msp I
                                                     Sfi I      Hpa II
                                                     Hae III  Hae III
                                                     Gdi II   Sau96 I
                                                     Eae I   BstK I
                                  Sac I              Msp I    Nci I
                                  HgiA I             Hpa II   Bcn I
                                  Ecl136 I           ScrF I   Dsa V
                                  Bsp1286 I          Nci I   BstK I
                   Mnl I          Ban II             Dsa V   BsaJ I
            Mbo II                Bph I              BstK I  Bcn I           Mbo II
     Bsr I    Ear I       Bsr I   Alu I              Bcn I   Ava I           Bbs I
       |       |           |      | |                |||||   || || |           |
     AGGACGACTGGGACGAAGAGGACGACTGGTGAGCTCCCGTAATGACAACAGACTTCCCGGCCACCCGGGCCGAAGACTT  480
     TCCTGCTGACCCTGCTTCTCCTGCTGACCACTCGAGGGCATTACTGTTGTCTGAAGGGCCGGTGGGCCCGGCCTTCTGAA
       |      |    | |     |  |  ||         .        ||||  || ||  |        .
      407    415  425   432                          456   464  473
             415       428                           456   464  473
                  418  431                           456   464
                       431                           456   464
                       431                           456   464
                       431                           457   465
                       431                           457   464
                                                     458   465
                                                     458   467
                                                     459   468
                                                     459   470
                                                     460   470
                                                     460
                                                     464
                                                     464
                                                     464
                                                     465
                                                     465
                                                     465
                                                     465
                                                     465

HinP I
                                                                           Hha I
                                                                  Mnl I
                                                                  EcoN I
                                                       BspW I             BspW I
      BstX I      Mnl I                     Nla III   Mbo II  Bbs I SfaN I   Fnu4H I   BsiY I BstU I
       |           |                         |         |   |     |    |      | ||
     GCCAACATTTTGGCGAGGAAGGTAAAGAGAGAAAGTAGTCCAGCATGGCAGAGATGAAGACCGATGCCGCTACCCTCGCG  560
     CGGTTGTAAAACCGCTCCTTCCATTTCTCTCTTTCATCAGGTCGTACCGTCTCTACTTCTGGCTACGGCGATGGGAGCGC
       |        .  |             .       |           |    |        |   | | |   .
      482       495                     524         536  543      554
                                                    536           549  557
                                                                       554  558
                                                                       554
                                                                            558
                                                                            558

ScrF I
                                                        EcoR II
                                            Msp I       Dsa V
                                            Hpa II      BstN I         BceF I
                                        Sau3A I         BstK I         Taq I
                                        Mbo I           Taq I           Sal I
                                        Dpn II          Sau3A I        Bioc II
                                        BstY I          Mbo I          Acc I
                          -             Alw I           Dpn II         Ple I
       BspM I             Taq I         Dpn I           Dpn I          Hinf I    BspM I
     Mnl I                  |             ||  |          | |            ||||       |
       |                    |             ||  |          | |            ||||       |
     CAGGAGGCAGGTAATTTCGAGCGGATCTCCGGCGACCTGAAAACCCAGATCGACCAGGTGGAGTCGACGGCAGGTTCGTT  640
     GTCCTCCGTCCATTAAAGCTCGCCTAGAGGCCGCTGGACTTTTGGGTCTAGCTGGTCCACCTCAGCTGCCGTCCAAGCAA
       |                    |           |            |         .| ||   |       .
      564                  577          584          608        621    630
             567                        583                     621
                                        583                     623
                                        584          608        623
                                        584          608        623
                                        584          610        624
                                                                627
                                        589         614
                                        589         614
                                                    614
                                                    614
                                                    614
```

-71-

```
                                    ScrF I
                                    EcoR II
                                    BsaJ I
                                    BspW I
                         Fnu4H I            BstU I
                         BspW I             Sac II
                         Bgl I              NspB II
                         Sfi I              Dsa I
              BstU I     McrI  Dsa V
              HinP I     Gdi II        BsaJ I
              HinP I  Fau I    FagI  BstN I
   Bsr I      Hha I     Eae I  BstK I
   BspW I   Fnu4H I     BsiE I      Fnu4H I
   Hae III  BstU I   BspW I  Hae III Hae III Hae III       HinP I      Fnu4H I
   Sau96 I  Hha I  Fnu4H I  BceF I  BsiY I                  Hha I       Bbv I
   ||||     |||    |||    |  ||||   |||  ||||                |           |
GCAGGGCCAGTGGCGCGGCGCGGCGGGGACGGCCGCCCAGGCCGCGGTGGTGCGCTTCCAAGAAGCAGCCAATAAGCAGA  720
CGTCCCGGTCACCGCGCCGCGCCGCCCCTGCCGGCGGGTCCGGCGCCACCACGCGAAGGTTCTTCGTCGGTTATTCGTCT
    ||||  •  |||   |||   |    |||| |||  ||||            •  |           •   |           •    •
    644       653    660     669    677                      692             705
    645       654    663     671    680                      692             705
    646       655            670    681
    647              658            670    677
                     653    663     670    677
                            658             670            682
                            659             670    677
                                            671            682
                                            672            682
                                            672    682
                                            672            683
                                                    675
                                                    676
                                                    677
                                                    677

Taq I              Hga I       Hae III
                Sau3A I            Aha II      Sau96 I
                Mbo I              Msp I       Mnl I                       Fnu4H I
                Dpn II             Hpa II      Taq I                       BspW I
                BstY I             Nae I       Xho I            Fnu4H I    Hae II
                Bgl II             Cfr10 I     PaeR7 I          Bbv I      AlwN I
   Taq I  Dpn I         Ssp I      Hae III     Ava I     Mnl I  Bbv I      | |
    ||     ||            |         ||| ||      || ||       ||   || ••|      | |
AGCAGGAACTCGACGAGATCTCGACGAATATTCGTCAGGCCGGCGTCCAATACTCGAGGGCCGACGAGGAGCAGCAGCAG  800
TCGTCCTTGAGCTGCTCTAGAGCTGCTTATAAGCAGTCCGGCCGCAGGTTATGAGCTCCCGGCTGCTCCTCGTCGTCGTC
    |       ||    •|      |    •       |||  ||       || |  ||•     |       |  | |
    730     737         747          758      773             786     794
             736                     759      773                     791     798
             736                     759      773                     791    800
             737                     760      774                            794
             737                     760      776                            794
             737                             778
                741                     762   779
                                        763

BspW I
    HinP I                                                                    Fnu4H I
    Hha I    Mnl I          Fau I                              Nla III       Bbv I
    | |      |              |                                  |              |
GCGCTGTCCTCGCAAATGGGCCTTCTGACCCGCTAATACGAAAAGAAACGGAGCAAAAACatgacagagcagcagtggaat  880
CGCGACAGGAGCGTTTACCCGAAGACTGGGCGATTATGCTTTTCTTTGCCTCGTTTTTGtactgtctcgtcgtcaccttta
    | |      |      •         |  •              |•          |•       |•        •
    801     808             828                              859           868
    801                                                                    868
    803

Fnu4H I
                    BspW I
                    Sac II
                    NspB II
                    Dsa I         ScrF I
                    BsaJ I        EcoR II
                    Fnu4H I       Dsa V
                    Hae III       BstN I
   Fau I   Mnl I                  BstK I                              EcoN I
   BstU I  Taq I    BstU I  HinP I         Mae II              Mnl I  BsiY I
   | |     |        |||||•  | |  BsaJ I    Mae III    Mnl I    | |    AlwN I
   | |     |        |||||•  | |  | |       | |       | |      | |     |
ttcgcgggtatcgaggccgcggcaagcgcaatccagggaaatgtcacgtccattcattccctccttgacgagggggaagca  960
aagcgcccatagctccggcgccgttcgcgttaggtcccctttacagtgcaggtaagtaagggaggaactgctcccccttcgt
    ||     •| | |||||•    |   •                • |    •    •        |•        | •
    883   891     898    906    913          923           940      950       959
          884     893    906    913          926                    943
                  895            913                                943
                  896            913
                  897            913
                  897            913
                  897
                  897
                         899
                         899
```

```
                              ScrF I
                              EcoR II
                              Dsa V                    ScrF I
                              BstN I                   EcoR II
                              BstK I                   Dsa V
                          Hae III                      BstN I                    BceF I
                        NspB II                        BstK I                    Dsa I
                        Fnu4H I                        Rsa I                     BsaJ I
                        Bbv I  BsaJ I                  Csp6 I                    Hga I
                 Alu I  Fnu4H I                  Mnl I  BsaJ I                   Aha II
                   |    ||||                       |      ||                       ||
        gtccctgaccaagctcgcagcggcctggggcggtagcggttcggaggcgtaccagggtgtccagcaaaaatgggacgcca  1040
        cagggactggttcgagcgtcgccggaccccgccatcgccaaggcctccgcatggtcccacaggtcgttttttaccctgcggt
        . |     . |     ||||                       . |       . |               . ||
          972     980                              1004      1012              1034    1040
                  977    984                              1009                 1034
                  977                                     1009
                  978                                                          1038
                         982                                     1012          1038
                         984                                     1012                  1040
                         984                                     1012
                         984                                     1012
                         984
                         984
                         Sfe I
                         Pst I
                         Fnu4H I
                         Bbv I
                         HinP I
                         Hha I
                 Alu I   BstU I
                   |     ||  ||
        cggctaccgagctgaacaacgcgctgcag 1069
        gccgatggctcgacttgttgcgcgacgtc
          |                ||  ||
          1050             1060
                           1061
                           1061
                           1063
                           1063
                           1064
                           1064
```

Restriction Endonucleases site usage

| | | | | | | | |
|---|---|---|---|---|---|---|---|
| Aat II | 1 | BssH II | 1 | Hga I | 2 | Pml I | - |
| Acc I | 1 | BstB I | - | HgiA I | 1 | PpuM I | - |
| Afl II | - | BstE II | - | Hha I | 17 | PshA I | - |
| Afl III | - | BstK I | 14 | Hinc II | 2 | Pst I | 2 |
| Age I | - | BstN I | 9 | Hind III | - | Pvu I | - |
| Aha II | 4 | BstU I | 14 | Hinf I | 2 | Pvu II | 1 |
| Alu I | 4 | BstX I | 1 | HinP I | 17 | Rma I | - |
| Alw I | 3 | BstY I | 2 | Hpa I | - | Rsa I | 1 |
| AlwN I | 2 | Bsu36 I | - | Hpa II | 14 | Rsr II | - |
| Apa I | - | Cfr10 I | 5 | Hph I | 3 | Sac I | 1 |
| ApaL I | - | Cla I | - | Kas I | 1 | Sac II | 2 |
| Ase I | - | Csp6 I | 1 | Kpn I | - | Sal I | 1 |
| Asp718 | - | Dde I | 1 | Mae II | 2 | Sap I | - |
| Ava I | 2 | Dpn I | 6 | Mae III | 2 | Sau3A I | 6 |
| Ava II | 1 | Dpn II | 6 | Mbo I | 6 | Sau96 I | 8 |
| Avr II | - | Dra I | - | Mbo II | 5 | Sca I | - |
| BamH I | - | Dra III | - | Mcr I | 1 | ScrF I | 14 |
| Ban I | 4 | Drd I | - | Mlu I | - | SfaN I | 2 |
| Ban II | 1 | Dsa I | 3 | Mme I | - | Sfe I | 2 |
| Bbe I | 1 | Dsa V | 14 | Mnl I | 14 | Sfi I | 2 |
| Bbs I | 3 | Eae I | 2 | Msc I | - | SgrA I | 1 |
| Bbv I | 10 | Eag I | 1 | Mse I | - | Sma I | 1 |
| BceF I | 3 | Ear I | 1 | Msp I | 14 | Sna I | - |
| Bcl I | - | Ecl136 I | 1 | Nae I | 3 | SnaB I | - |
| Bcn I | 5 | Eco47 III | - | Nar I | 1 | Spe I | - |
| Bgl I | 4 | Eco57 I | - | Nci I | 5 | Sph I | 1 |
| Bgl II | 1 | EcoN I | 3 | Nco I | - | Spl I | - |
| Bsa I | - | EcoO109 I | 1 | Nde I | - | Sse8337 I | - |
| BsaA I | - | EcoR I | - | Nhe I | - | Ssp I | 1 |
| BsaB I | - | EcoR II | 9 | Nla III | 2 | Stu I | - |
| BsaJ I | 10 | EcoR V | - | Nla IV | 7 | Sty I | - |
| Bsg I | - | Ehe I | 1 | Not I | - | Swa I | - |
| BsiE I | 1 | Esp I | - | Nru I | - | Taq I | 9 |
| BsiY I | 8 | Fau I | 6 | Nsi I | - | Tfi I | - |
| Bsm I | - | Fse I | - | Nsp I | - | Tth111 I | - |
| BsmA I | 1 | Fnu4H I | 26 | Nsp7524 I | - | Tth111 II | - |
| Bsp120 I | - | Fok I | 1 | NspB II | 7 | Xba I | - |
| Bsp1286 I | 1 | Fsp I | 1 | NspC I | - | Xca I | - |
| BspE I | - | Gdi II | 2 | Pac I | - | Xcm I | 2 |
| BspH I | - | Gsu I | - | PaeR7 I | 1 | Xho I | 1 |
| BspM I | 4 | Hae I | - | PflM I | 1 | Xma I | 1 |
| BspW I | 18 | Hae II | 2 | Ple I | 2 | Xmn I | - |
| Bsr I | 4 | Hae III | 14 | | | | |

| Enzyme | Site | Use | Site position (Fragment length) Fragment order | | | | |
|---|---|---|---|---|---|---|---|
| Aat II | gacgt/c | 1 | 1( 11) 2 | 12( 1058) 1 | | | |
| Acc I | gt/mkac | 1 | 1( 622) 1 | 623( 447) 2 | | | |
| Ava II | g/gwcc | 1 | 1( 300) 2 | 301( 769) 1 | | | |
| Ban II | grgcy/c | 1 | 1( 430) 2 | 431( 639) 1 | | | |
| Bbe I | ggcgc/c | 1 | 1( 285) 2 | 286( 784) 1 | | | |
| Bgl II | a/gatct | 1 | 1( 735) 1 | 736( 334) 2 | | | |
| BsiE I | cgry/cg | 1 | 1( 669) 2 | 670( 400) 1 | | | |
| BsmA I | gtctc 1/5 | 1 | 1( 212) 2 | 213( 857) 1 | | | |
| Bsp1286 I | gdgch/c | 1 | 1( 430) 2 | 431( 639) 1 | | | |
| BssH II | g/cgcgc | 1 | 1( 158) 2 | 159( 911) 1 | | | |
| BstX I | ccannnnn/ntgg | 1 | 1( 481) 2 | 482( 588) 1 | | | |
| Csp6 I | g/tac | 1 | 1( 1008) 1 | 1009( 61) 2 | | | |
| Dde I | c/tnag | 1 | 1( 214) 2 | 215( 855) 1 | | | |
| Eag I | c/ggccg | 1 | 1( 669) 2 | 670( 400) 1 | | | |
| Ear I | ctcttc 1/4 | 1 | 1( 414) 2 | 415( 655) 1 | | | |
| Ecl136 I | gag/ctc | 1 | 1( 430) 2 | 431( 639) 1 | | | |
| EcoO109 I | rg/gnccy | 1 | 1( 131) 2 | 132( 938) 1 | | | |
| Ehe I | ggc/gcc | 1 | 1( 285) 2 | 286( 784) 1 | | | |
| Fok I | ggatg 9/13 | 1 | 1( 111) 2 | 112( 958) 1 | | | |
| Fsp I | tgc/gca | 1 | 1( 323) 2 | 324( 746) 1 | | | |
| HgiA I | gwgcw/c | 1 | 1( 430) 2 | 431( 639) 1 | | | |
| Kas I | g/gcgcc | 1 | 1( 285) 2 | 286( 784) 1 | | | |
| Mcr I | c/grycg | 1 | 1( 669) 1 | 670( 400) 2 | | | |
| Nar I | gg/cgcc | 1 | 1( 285) 2 | 286( 784) 1 | | | |
| PaeR7 I | c/tcgag | 1 | 1( 772) 1 | 773( 297) 2 | | | |
| PflM I | ccannnn/ntgg | 1 | 1( 110) 2 | 111( 959) 1 | | | |
| Pvu II | cag/ctg | 1 | 1( 216) 2 | 217( 853) 1 | | | |
| Rsa I | gt/ac | 1 | 1( 1008) 1 | 1009( 61) 2 | | | |
| Sac I | gagct/c | 1 | 1( 430) 2 | 431( 639) 1 | | | |
| Sal I | g/tcgac | 1 | 1( 622) 1 | 623( 447) 2 | | | |
| SgrA I | cr/ccggyg | 1 | 1( 38) 2 | 39( 1031) 1 | | | |
| Sma I | ccc/ggg | 1 | 1( 463) 2 | 464( 606) 1 | | | |
| Ssp I | aat/att | 1 | 1( 746) 1 | 747( 323) 2 | | | |
| Xho I | c/tcgag | 1 | 1( 772) 1 | 773( 297) 2 | | | |
| Xma I | c/ccggg | 1 | 1( 463) 2 | 464( 606) 1 | | | |
| AlwN I | cagnnn/ctg | 2 | 1( 797) 1 | 798( 161) 2 | 959( 111) 3 | | |
| Ava I | c/ycgrg | 2 | 1( 463) 1 | 464( 309) 2 | 773( 297) 3 | | |
| BstY I | r/gatcy | 2 | 1( 582) 1 | 583( 153) 3 | 736( 334) 2 | | |
| Eae I | y/ggccr | 2 | 1( 457) 1 | 458( 212) 3 | 670( 400) 2 | | |
| Gdi II | yggccg -5/-1 | 2 | 1( 457) 1 | 458( 212) 3 | 670( 400) 2 | | |
| Hae II | rgcgc/y | 2 | 1( 285) 2 | 286( 514) 1 | 800( 270) 3 | | |
| Hga I | gacgc 5/10 | 2 | 1( 762) 1 | 763( 271) 2 | 1034( 36) 3 | | |
| Hinc II | gty/rac | 2 | 1( 191) 3 | 192( 431) 2 | 623( 447) 1 | | |
| Hinf I | g/antc | 2 | 1( 165) 3 | 166( 455) 1 | 621( 449) 2 | | |
| Mae II | a/cgt | 2 | 1( 12) 3 | 13( 913) 1 | 926( 144) 2 | | |
| Mae III | /gtnac | 2 | 1( 9) 3 | 10( 913) 1 | 923( 147) 2 | | |
| Nla III | catg/ | 2 | 1( 523) 1 | 524( 335) 2 | 859( 211) 3 | | |
| Ple I | gagtc 4/5 | 2 | 1( 165) 3 | 166( 455) 1 | 621( 449) 2 | | |
| Pst I | ctgca/g | 2 | 1( 0) 3 | 1( 1063) 1 | 1064( 6) 2 | | |
| Sac II | ccgc/gg | 2 | 1( 681) 1 | 682( 215) 2 | 897( 173) 3 | | |
| SfaN I | gcatc 5/9 | 2 | 1( 248) 3 | 249( 294) 2 | 543( 527) 1 | | |
| Sfe I | c/tryag | 2 | 1( 0) 3 | 1( 1063) 1 | 1064( 6) 2 | | |
| Sfi I | ggccnnnn/nggcc | 2 | 1( 458) 1 | 459( 212) 3 | 671( 399) 2 | | |
| Xcm I | ccannnnn/nnnntgg | 2 | 1( 110) 3 | 111( 233) 2 | 344( 726) 1 | | |
| Alw I | ggatc 4/5 | 3 | 1( 126) 4 | 127( 141) 3 | 268( 315) 2 | 583( 487) 1 | |
| Bbs I | gaagac 2/6 | 3 | 1( 390) 2 | 391( 82) 3 | 473( 63) 4 | 536( 534) 1 | |
| BceF I | acggc 12/13 | 3 | 1( 626) 1 | 627( 42) 3 | 669( 371) 2 | 1040( 30) 4 | |
| Dsa I | c/crygg | 3 | 1( 681) 2 | 682( 215) 3 | 897( 141) 1 | 1038( 32) 4 | |
| EcoN I | cctnn/nnnagg | 3 | 1( 174) 3 | 175( 379) 1 | 554( 389) 2 | 943( 127) 4 | |
| Hph I | ggtga 8/7 | 3 | 1( 8) 4 | 9( 237) 2 | 246( 182) 3 | 428( 642) 1 | |
| Nae I | gcc/ggc | 3 | 1( 251) 3 | 252( 111) 4 | 363( 396) 1 | 759( 311) 2 | |
| Aha II | gr/cgyc | 4 | 1( 11) 5<br>1034( 36) 4 | 12( 274) 2 | 286( 476) 1 | 762( 272) 3 | |
| Alu I | ag/ct | 4 | 1( 217) 2<br>1050( 20) 5 | 218( 214) 3 | 432( 540) 1 | 972( 78) 4 | |
| Ban I | g/gyrcc | 4 | 1( 36) 5<br>366( 704) 1 | 37( 54) 4 | 91( 195) 2 | 286( 80) 3 | |
| Bgl I | gccnnnn/nggc | 4 | 1( 25) 5<br>672( 398) 1 | 26( 57) 4 | 83( 377) 2 | 460( 212) 3 | |
| BspM I | acctgc 4/8 | 4 | 1( 5) 5<br>630( 440) 1 | 6( 175) 3 | 181( 386) 2 | 567( 63) 4 | |
| Bsr I | actgg 1/-1 | 4 | 1( 94) 4<br>647( 423) 1 | 95( 312) 2 | 407( 18) 5 | 425( 222) 3 | |
| Bcn I | ccs/gg | 5 | 1( 303) 2<br>464( 1) 6 | 304( 45) 4<br>465( 605) 1 | 349( 107) 3 | 456( 8) 5 | |
| Cfr10 I | r/ccggy | 5 | 1( 39) 5<br>363( 396) 1 | 40( 191) 3<br>759( 311) 2 | 231( 21) 6 | 252( 111) 4 | |
| Mbo II | gaaga 8/7 | 5 | 1( 387) 2<br>473( 63) 3 | 388( 3) 6<br>536( 534) 1 | 391( 24) 5 | 415( 58) 4 | |
| Nci I | cc/sgg | 5 | 1( 303) 2<br>464( 1) 6 | 304( 45) 4<br>465( 605) 1 | 349( 107) 3 | 456( 8) 5 | |
| Dpn I | ga/tc | 6 | 1( 127) 4<br>584( 24) 7 | 128( 94) 5<br>608( 129) 3 | 222( 47) 6<br>737( 333) 1 | 269( 315) 2 | |
| Dpn II | /gatc | 6 | 1( 127) 4 | 128( 94) 5 | 222( 47) 6 | 269( 315) 2 | |

| Enzyme | Site | Cut | N | | | | | | | | | |
|---|---|---|---|---|---|---|---|---|---|---|---|---|
| Fau I | cccgc | 4/6 | 6 | 584( | 24) 7 | 608( | 129) 3 | 737( | 333) 1 | | | |
| | | | | 1( | 141) 4 | 142( | 6) 7 | 148( | 49) 6 | 197( | 466) 1 | |
| | | | | 663( | 165) 3 | 828( | 56) 5 | 884( | 186) 2 | | | |
| Mbo I | /gatc | | 6 | 1( | 127) 4 | 128( | 94) 5 | 222( | 47) 6 | 269( | 315) 2 | |
| | | | | 584( | 24) 7 | 608( | 129) 3 | 737( | 333) 1 | | | |
| Sau3A I | /gatc | | 6 | 1( | 127) 4 | 128( | 94) 5 | 222( | 47) 6 | 269( | 315) 2 | |
| | | | | 584( | 24) 7 | 608( | 129) 3 | 737( | 333) 1 | | | |
| Nla IV | ggn/ncc | | 7 | 1( | 36) 6 | 37( | 54) 3 | 91( | 42) 4 | 133( | 153) 2 | |
| | | | | 286( | 14) 8 | 300( | 37) 5 | 337( | 29) 7 | 366( | 704) 1 | |
| NspB II | cmg/ckg | | 7 | 1( | 99) 3 | 100( | 15) 7 | 115( | 90) 5 | 205( | 12) 8 | |
| | | | | 217( | 465) 1 | 682( | 215) 2 | 897( | 81) 6 | 978( | 92) 4 | |
| BsiY I | ccnnnnn/nngg | | 8 | 1( | 110) 5 | 111( | 4) 8 | 115( | 20) 7 | 135( | 1) 9 | |
| | | | | 136( | 39) 6 | 175( | 379) 1 | 554( | 123) 4 | 677( | 266) 2 | |
| | | | | 943( | 127) 3 | | | | | | | |
| Sau96 I | g/gncc | | 8 | 1( | 80) 6 | 81( | 52) 7 | 133( | 17) 8 | 150( | 151) 4 | |
| | | | | 301( | 14) 9 | 315( | 152) 3 | 467( | 177) 2 | 644( | 134) 5 | |
| | | | | 778( | 292) 1 | | | | | | | |
| BstN I | cc/wgg | | 9 | 1( | 26) 9 | 27( | 148) 3 | 175( | 143) 4 | 318( | 26)10 | |
| | | | | 344( | 270) 1 | 614( | 63) 6 | 677( | 236) 2 | 913( | 71) 5 | |
| | | | | 984( | 28) 8 | 1012( | 58) 7 | | | | | |
| EcoR II | /ccwgg | | 9 | 1( | 26) 9 | 27( | 148) 3 | 175( | 143) 4 | 318( | 26)10 | |
| | | | | 344( | 270) 1 | 614( | 63) 6 | 677( | 236) 2 | 913( | 71) 5 | |
| | | | | 984( | 28) 8 | 1012( | 58) 7 | | | | | |
| Taq I | t/cga | | 9 | 1( | 105) 6 | 106( | 118) 3 | 224( | 353) 1 | 577( | 33) 7 | |
| | | | | 610( | 14) 9 | 624( | 106) 5 | 730( | 11)10 | 741( | 33) 8 | |
| | | | | 774( | 117) 4 | 891( | 179) 2 | | | | | |
| Bbv I | gcagc | 8/12 | 10 | 1( | 2)11 | 3( | 153) 2 | 156( | 103) 4 | 259( | 3) 9 | |
| | | | | 262( | 443) 1 | 705( | 86) 5 | 791( | 3)10 | 794( | 74) 7 | |
| | | | | 868( | 109) 3 | 977( | 86) 6 | 1063( | 7) 8 | | | |
| BsaJ I | c/cnngg | | 10 | 1( | 241) 1 | 242( | 76) 5 | 318( | 146) 4 | 464( | 212) 3 | |
| | | | | 676( | 6)11 | 682( | 215) 2 | 897( | 16)10 | 913( | 71) 6 | |
| | | | | 984( | 28) 8 | 1012( | 26) 9 | 1038( | 32) 7 | | | |
| BstK I | c/cngg | | 14 | 1( | 26)10 | 27( | 148) 3 | 175( | 129) 4 | 304( | 14)12 | |
| | | | | 318( | 26)11 | 344( | 5)14 | 349( | 107) 5 | 456( | 8)13 | |
| | | | | 464( | 1)15 | 465( | 149) 2 | 614( | 63) 7 | 677( | 236) 1 | |
| | | | | 913( | 71) 6 | 984( | 28) 9 | 1012( | 58) 8 | | | |
| BstU I | cg/cg | | 14 | 1( | 71) 6 | 72( | 69) 7 | 141( | 6)13 | 147( | 13)11 | |
| | | | | 160( | 2)15 | 162( | 198) 2 | 360( | 15) 9 | 375( | 182) 3 | |
| | | | | 557( | 97) 5 | 654( | 5)14 | 659( | 24) 8 | 683( | 200) 1 | |
| | | | | 883( | 15)10 | 898( | 162) 4 | 1060( | 10)12 | | | |
| Dsa V | /ccngg | | 14 | 1( | 26)10 | 27( | 148) 3 | 175( | 129) 4 | 304( | 14)12 | |
| | | | | 318( | 26)11 | 344( | 5)14 | 349( | 107) 5 | 456( | 8)13 | |
| | | | | 464( | 1)15 | 465( | 149) 2 | 614( | 63) 7 | 677( | 236) 1 | |
| | | | | 913( | 71) 6 | 984( | 28) 9 | 1012( | 58) 8 | | | |
| Hae III | gg/cc | | 14 | 1( | 81) 7 | 82( | 51) 9 | 133( | 18)13 | 151( | 165) 2 | |
| | | | | 316( | 31)10 | 347( | 112) 4 | 459( | 9)14 | 468( | 177) 1 | |
| | | | | 645( | 26)11 | 671( | 9)15 | 680( | 78) 8 | 758( | 21)12 | |
| | | | | 779( | 116) 3 | 895( | 87) 6 | 982( | 88) 5 | | | |
| Hpa II | c/cgg | | 14 | 1( | 40) 6 | 41( | 191) 2 | 232( | 21) 9 | 253( | 13)12 | |
| | | | | 266( | 29) 7 | 295( | 9)13 | 304( | 28) 8 | 332( | 17)10 | |
| | | | | 349( | 15)11 | 364( | 93) 5 | 457( | 8)14 | 465( | 5)15 | |
| | | | | 470( | 119) 4 | 589( | 171) 3 | 760( | 310) 1 | | | |
| Mnl I | cctc | 7/7 | 14 | 1( | 63) 7 | 64( | 178) 2 | 242( | 158) 3 | 400( | 18)12 | |
| | | | | 418( | 77) 5 | 495( | 59) 8 | 554( | 10)13 | 564( | 212) 1 | |
| | | | | 776( | 10)14 | 786( | 22)11 | 808( | 85) 4 | 893( | 47)10 | |
| | | | | 940( | 10)15 | 950( | 54) 9 | 1004( | 66) 6 | | | |
| Msp I | c/cgg | | 14 | 1( | 40) 6 | 41( | 191) 2 | 232( | 21) 9 | 253( | 13)12 | |
| | | | | 266( | 29) 7 | 295( | 9)13 | 304( | 28) 8 | 332( | 17)10 | |
| | | | | 349( | 15)11 | 364( | 93) 5 | 457( | 8)14 | 465( | 5)15 | |
| | | | | 470( | 119) 4 | 589( | 171) 3 | 760( | 310) 1 | | | |
| ScrF I | cc/ngg | | 14 | 1( | 26)10 | 27( | 148) 3 | 175( | 129) 4 | 304( | 14)12 | |
| | | | | 318( | 26)11 | 344( | 5)14 | 349( | 107) 5 | 456( | 8)13 | |
| | | | | 464( | 1)15 | 465( | 149) 2 | 614( | 63) 7 | 677( | 236) 1 | |
| | | | | 913( | 71) 6 | 984( | 28) 9 | 1012( | 58) 8 | | | |
| Hha I | gcg/c | | 17 | 1( | 72) 7 | 73( | 67) 8 | 140( | 6)16 | 146( | 13)14 | |
| | | | | 159( | 2)18 | 161( | 18)12 | 179( | 108) 4 | 287( | 38) 9 | |
| | | | | 325( | 36)10 | 361( | 15)13 | 376( | 182) 1 | 558( | 95) 6 | |
| | | | | 653( | 5)17 | 658( | 34)11 | 692( | 109) 3 | 801( | 105) 5 | |
| | | | | 906( | 155) 2 | 1061( | 9)15 | | | | | |
| HinP I | g/cgc | | 17 | 1( | 72) 7 | 73( | 67) 8 | 140( | 6)16 | 146( | 13)14 | |
| | | | | 159( | 2)18 | 161( | 18)12 | 179( | 108) 4 | 287( | 38) 9 | |
| | | | | 325( | 36)10 | 361( | 15)13 | 376( | 182) 1 | 558( | 95) 6 | |
| | | | | 653( | 5)17 | 658( | 34)11 | 692( | 109) 3 | 801( | 105) 5 | |
| | | | | 906( | 155) 2 | 1061( | 9)15 | | | | | |
| BspW I | gcnnnnn/nngc | | 18 | 1( | 25)11 | 26( | 9)13 | 35( | 3)18 | 38( | 45)10 | |
| | | | | 83( | 69) 9 | 152( | 104) 4 | 256( | 107) 3 | 363( | 4)17 | |
| | | | | 367( | 93) 6 | 460( | 89) 7 | 549( | 9)14 | 558( | 88) 8 | |
| | | | | 646( | 17)12 | 663( | 9)15 | 672( | 3)19 | 675( | 119) 2 | |
| | | | | 794( | 9)16 | 803( | 96) 5 | 899( | 171) 1 | | | |
| Fnu4H I | gc/ngc | | 26 | 1( | 2)27 | 3( | 32)11 | 35( | 9)17 | 44( | 3)21 | |
| | | | | 47( | 23)15 | 70( | 86) 3 | 156( | 48) 9 | 204( | 52) 8 | |
| | | | | 256( | 3)22 | 259( | 3)23 | 262( | 27)13 | 289( | 46)10 | |
| | | | | 335( | 211) 1 | 546( | 109) 2 | 655( | 5)20 | 660( | 12)16 | |
| | | | | 672( | 9)18 | 681( | 24)14 | 705( | 86) 4 | 791( | 3)24 | |
| | | | | 794( | 74) 7 | 868( | 28)12 | 896( | 3)25 | 899( | 78) 6 | |

No Sites found for the following Restriction Endonucleases

| | | | | | |
|---|---|---|---|---|---|
| Afl II | c/ttaag | Eco47 III | agc/gct | Pac I | ttaat/taa |
| Afl III | a/crygt | Eco57 I | ctgaag 16/14 | Pml I | cac/gtg |
| Age I | a/ccggt | EcoR I | g/aattc | PpuM I | rg/gwccy |
| Apa I | gggcc/c | EcoR V | gat/atc | PshA I | gacnn/nngtc |
| ApaL I | g/tgcac | Esp I | gc/tnagc | Pvu I | cgat/cg |
| Ase I | at/taat | Fse I | ggccgg/cc | Rma I | c/tag |
| Asp718 | g/gtacc | Gsu I | ctggag 16/14 | Rsr II | cg/gwccg |
| Avr II | c/ctagg | Hae I | wgg/ccw | Sap I | gcttcttc 1/4 |
| BamH I | g/gatcc | Hind III | a/agctt | Sca I | agt/act |
| Bcl I | t/gatca | Hpa I | gtt/aac | Sna I | gta/tac |
| Bsa I | ggtctc 1/5 | Kpn I | ggtac/c | SnaB I | tac/gta |
| BsaA I | yac/gtr | Mlu I | a/cgcgt | Spe I | a/ctagt |
| BsaB I | gatnn/nnatc | Mme I | tccrac 20/18 | Sph I | gcatg/c |
| Bsg I | gtgcag 16/14 | Msc I | tgg/cca | Spl I | c/gtacg |
| Bsm I | gaatgc 1/-1 | Mse I | t/taa | Sse8337 I | cctgca/gg |
| Bsp120 I | g/ggccc | Nco I | c/catgg | Stu I | agg/cct |
| BspE I | t/ccgga | Nde I | ca/tatg | Sty I | c/cwwgg |
| BspH I | t/catga | Nhe I | g/ctagc | Swa I | attt/aaat |
| BstB I | tt/cgaa | Not I | gc/ggccgc | Tfi I | g/awtc |
| BstE II | g/gtnacc | Nru I | tcg/cga | Tth111 I | gacn/nngtc |
| Bsu36 I | cc/tnagg | Nsi I | atgca/t | Tth111 II | caarca 11/9 |
| Cla I | at/cgat | Nsp I | rcatg/y | Xba I | t/ctaga |
| Dra I | ttt/aaa | Nsp7524 I | r/catgy | Xca I | gta/tac |
| Dra III | cacnnn/gtg | NspC I | rcatg/y | Xmn I | gaann/nnttc |
| Drd I | gacnnnn/nngtc | | | | |

Annex II

KpnI BamHI DNA insert of plasmid pIPX26

```
                                    Fnu4H I
                                    HinP I
                                    Hha I            ScrF I
                                    Nla IV           Nci I          ScrF I
                      Fnu4H I   SauJA I   Nar I      Msp I          EcoR II
                      BspW I    Mbo I     Kas I      Hpa II         Osa V
              Msp I   Opn II    Hae II    Dsa V      BscN I
              Nae I   Dpn I     Ehe I     Sau96 I    BscK I
       Hph I  Hpa II  Alw I     Mae III   Sbe I      Ava II         BsaJ I
  Mnl I SfaN I        Msp I     Hph I     Ban I      Nla IV         Hae III
  BsaJ I Cfr10 I      Hpa II    Aha II    Msp I      BscK I         Sau96 I
  | |   | || |  | |   |   ||     | | |    |  ||      | |            | | |
CCTCGGTGATGCCGGCGGCTGTTGCCGGATCGTCGGTGACGGGTGGCGCCGCTCCGGTGGGTCCGGGAGCGATGGGCCAG 320
GGAGCCACTACGGCCGCCGACAACGGCCTAGCAGCCACTGCCCACCGCGGCGAGGCCACCCAGGCCCTCGCTACCCGGTC
  | |   | ||| |  | |   |   ||     | | |    |  ||      | |            | | |
  241   251      265        275    285    294        303             314
  241   248      265        276    285    294        303             315
        245      252        267    285    299        303             317
             251 252        268    285    300        303             317
                 255        268    285    300        303             317
                 255        268    285           303    317
                            268    285           303    317
                                   285           303    317
                                   285           303    317
                                   286           303
                                   286
                                   288

ScrF I
                         Nci I
                         Msp I
                         Hpa II
                         Osa V
                         BscK I
                         Bcn I          BspW I
                         Xma I          Nla IV
                         Sma I          Ban I
                         ScrF I         Msp I
                         Nci I          Hpa II
                         Osa V          Nae I
                         BscK I         Cfr10 I
              BspW I     BsiY I         BspW I
              Nla IV     BsaJ I         HinP I    HinP I    Mbo II
       Fnu4H I           Bcn I          Hha I     Hha I     Sbs I
   Msp I                 Ava I          BscU I    BscU I    Mbo II    Mnl I
   Hpa II  Xcm I         ||             ||        ||        ||        |
   | | |    ||           ||             ||        ||        ||        |
GGTTCGCAATCCGGCGGGTCCACCAGCCCGGGTCTGGTCGCGCCGGCACCGCTCGCGCAGGAGCGTGAAGAAGACGACGA 400
CCAAGCGTTAGGCCGCCGAGGTGGTCGGGCCCAGACCAGCGCGGCCGGTGGCGAGCGCGTCCTCGCACTTCTTCTGCTGCT
   | | |    ||           ||             ||        ||        ||        |
   331      343          359            374       387       399
   331                   360            375       390
        334              360            375       390
        336              362
        337              362
                         362
                         362
                         363
                         363
                         365
                         365
                         366
                         347
                         347
                         347
                         347
                         347
                         347
                         347
                         347
                         347
                         348
                         348
                         348
                         348
                         348
                         348
                         348
```

```
                                                                    ScrF I
                                                                    Nci I
                                                                    Msp I
                                                                    Hpa II
                                                                    Dsa V
                                                                    Xma I
                                                                    Sma I
                                                                    ScrF I
                                                        BspW I
                                                        Bgl I      Msp I
                                                        Sfi I      Hpa II
                                                        Hae III  Hae III
                                                        Gdi II   Sau96 I
                                                        Eae I    BstK I
                                      Sac I             Msp I    Nci I
                                      HgiA I            Hpa II   Bcn I
                                      Ecl116 I          ScrF I   Dsa V
                                      Bsp1286 I         Nci I    BstK I
                             Mnl I    Ban II            Dsa V    BsaJ I
          Mbo II             Hph I                      BstK I   Bcn I         Mbo II
     Bsr I  Ear I   Bsr I    Alu I                      Bcn I    Ava I         Bbs I
     |  |   | |     |  |     |  |                       |||||    || ||         || |
GGACGACTGGGACGAAGAGGACGACTGGTGAGCTCCCGTAATGACAACAGACTTCCGGGCCACCCGGGCCGGAAGACTTG   480
CCTGCTGACCCTGCTTCTCCTGCTGACCACTCGAGGGCATTACTGTTGTCTGAAGGCCCGGTGGGCCCGGCCTTCTGAAC
|    .    |  . | |   |  |    |   |                     |||||    || || | .       |
406       414  414    424   431                         455      463             472
              417            427                        455      463             472
                            430                         455      463
                            430                         455      463
                            430                         455      463
                            430                         456      464
                            430                         456      463
                                                        457      464
                                                        457      466
                                                        458      467
                                                        458           469
                                                        459           469
                                                        459
                                                        463
                                                        463
                                                        463
                                                        464
                                                        464
                                                        464
                                                        464
                                                        464
                                                                                  Mnl I
                                                                                  EcoN I
                                                                                  BsiY I
                                                          Mbo II   Fnu4H I  Ava I
  BstX I       Mnl I                      Nla III         Bbs I    SfaN I   BsaJ I
  |            |                          |               ||       |        ||
CCAACATTTTGGCGAGGAAGGTAAAGAGAGAAAGTAGTCCAGCATGGCAGAGATGAAGACCGATGCCGCTACCCTCGGGC    560
GGTTGTAAAACCGCTCCTTCCATTTCTCTCTTTCATCAGGTCGTACCGTCTCTACTTCTGGCTACGGCGATGGGAGCCCG
|       . |       .         .        .         |       |   .    |    .   ||
481         494                                 523     535      542       553
                                                        535               554
                                                                          553
                                                                          553
                                                                          553
                                                   ScrF I
                                                   EcoR II
                                                   Dsa V
                                  Msp I            BstN I          BceF I
                                  Hpa II           BstK I          Taq I
                          Sau3A I                                  Sal I
                          Mbo I                     Taq I          Hinc II
                          Dpn II                    Sau3A I        Acc I
                          BscY I                    Mbo I      Ple I
           BspM I         Alw I                     Dpn II     Hinf I   BspM I
  Mnl I    Taq I  Dpn I                             Dpn I      |  |     |
  |  |     |      -||                               |  |       |||      |
AGGAGGCAGGTAATTTCGAGCGGATCTCCGGCGACCTGAAAACCCAGATCGACCAGGTGGAGTCGACGGCAGGTTCGTTG   640
TCCTCCGTCCATTAAAGCTCGCCTAGAGGCCGCTGGACTTTTGGGTCTAGCTGGTCCACCTCAGCTGCCGTCCAAGCAAC
|   .     |       .         .         .         |    .     |  . |       ||   .
563       576     583                           607          620         629
   566             582                          607          620
                   582                          607          622
                   583                          607          622
                   583                          609          622
                   583                                       623
                   583                                 613         626
                          588                          613
                          588                          613
                                                       613
                                                       613
```

```
                                              ScrF I
                                              EcoR II
                                              BsaJ I
                                              BspW I
                                    Fnu4H I           BstU I
                                    BspW I            Sac II
                                    Bgl I             NspB II
                                    Sfi I             Dsa I
                         BstU I     Mcr I    Dsa V
                         Hin? I     Gdi II            BsaJ I
              HinP I     Fau I      Sag I    BstN I
    Bsr I     Hha I                 Eae I    BscK I
    BspW I    Fnu4H I               BsiE I            Fnu4H I
    Hae III   BstU I    BspW I      Hae III  Hae III  HinP I    Fnu4H I
    Sau96 I   Hha I     Fnu4H I     BceF I   BsiY I   Hha I     Bbv I
     ||||      |||       |||         ||||     |||     ||||       ||
CAGGGCCAGTGGCGCGGGCGCGGGGGACGGCCGCCCAGGCCGCGGTGGTCGCTTCCAAGAAGCAGCCAATAAGCAGAA  720
GTCCCGGTCACCGCGCCCGCGCCCCTGCCGGCGGGTCCGGCGCCACCAGCGAAGGTTCTTCGTCGGTTATTCGTCTT
  ||||      ||       |||·|       ||||     |||    ||||      ·|        ·     ·
  643     652  653        668    676     679         691          704
    644     653      662     670      679         691         704
      645      654         669     680
        646       657         669     676
                 652     662       669     676
                   657             669             681
                     658             669     676
                                     670             681
                                       671             681
                                         671             681
                                           671             682
                                             674
                                              .675
                                               676
                                                676
                         Taq I                        Hga I               Hae III
                         Sau3A I                      Aha II              Sau96 I            HinP I
                         Mbo I                        Msp I               Mnl I              Fnu4H I
                         Dpn II                       Hpa II              Taq I              BspW I
                         BstY I                       Nae I               Xho I              Fnu4H I   Hae II
                         Bgl II                       Cfr10 I             PaeR7 I            Bbv I    AlwN I
              Taq I      Dpn I    Ssp I    Hae III    Ava I               Mnl I    Bbv I     Hha I
                ||        ||        |        ||||      ||| ||  ·   ·        ||| ·   |||       |||
GCAGGAACTCGACGAGATCTCGACGAATATTCGTCAGGCCGGCGTCCAATACTCGAGGGCCGACGAGGAGCAGCAGCAGG  800
CGTCCTTGAGCTGCTCTAGAGCTGCTTATAAGCAGTCCGGCCGCAGGTTATGAGCTCCCGGCTGCTCCTCGTCGTCGTCC
  |·       ||        |     ·         ·  ||·||        |||·||  ·   ·         | ||      |||
  729       736         746              757            772         785       793      800
     735              746                  758              772           790      797
       735                                   758              772           790        799
         736                                   759              773             793
           736                                    759              775               793
             736                                     761              777
                 740                                   762              778
```

```
         Mnl I
         BspW I
           |     Fau I                              Nla III  Bbv I
                   |                                  |      |
CGCTGTCCTCGCAAATGGGCTTCTGACCCGCTAATACGAAAAGAAACGGAGCAAAAACATGACAGAGCAGCAGTGGAATT  880
GCGACAGGAGCGTTTACCCGAAGACTGGGCGATTATGCTTTTCTTTGCCTCGTTTTTGTACTGTCTCGTCGTCACCTTAA
  |      |·     ·        |                               |  ·            |   |
  802       807               827                           858      867
                                                              867
```

```
              Fnu4H I
              BspW I
              Sac II
              NspB II
              Dsa I              ScrF I
              BsaJ I             EcoR II
              Fnu4H I            Dsa V
              Hae III            BstN I                                      EcoN I
    Fau I     Mnl I     HinP I   BstK I            Mae II                    BsiY I
    BstU I    Taq I     BstU I   Hha I    BsaJ I   Mae III   Mnl I   Mnl I   AlwN I
      ||       |  ||||||·    |            ||        |         |       |·      |
TCGCGGGTATCGAGGCCGCGGCAAGCGCAATCCAGGGAAATGTCACGTCCATTCATTCCCTCCTTGACGAGGGGAAGCAG  960
AGCGCCCATAGCTCCGGCGCCGTTCGCGTTAGGTCCCTTTACAGTGCAGGTAAGTAAGGGAGGAACTGCTCCCCTTCGTC
  ||      |  | ||||| ·     |        · |          · |          · |        |·
  882      890     897      905       912          922          939     949   958
     883      892         892       905               925                 942
              894                912                                       942
                895                912
                  896                912
                    896              912
                      896              912
                        896
                         898
                          898
```

```
                              ScrF I
                              EcoR II
                              Dsa V              ScrF I
                              BstN I             EcoR II
                              BstK I             Dsa V
                              Hae III            BstN I                    Bcef I
                              NspB II            BstK I                    Dsa I
                              Fnu4H I            Rsa I                     BsaJ I
                              Bbv I  BsaJ I      Csp6 I                    Hga I
                          Alu I  Fnu4H I     Mnl I  BsaJ I                 Aha II
                          |   || | | |         |    |  |                   |  |
             TCCCTGACCAAGCTCGCAGCGGCCTGGGGCGGTAGCGGTTCGGAGGCGTACCAGGGTGTCCAGCAAAAATGGGACGCCAC  1040
             AGGGACTGGTTCGAGCGTCGCCGGACCCCGCCATCGCCAAGCCTCCGCATGGTCCCACAGGTCGTTTTTACCCTGCGGTG
              ·|     ||  |·|         ·       |     | ·|         ·        |  |·|       ·  ·|·
              971    979             1003   1011                1033     1033
                 976    983              1008                      1033
                 976                     1008                         1037
                    977                     1011                      1037
                       981                  1011                         1039
                          983               1011
                          983               1011
                          983               1011
                          983
                          983
                                   AlwN I    BstU I
                                   Sfe I     HinP I
                                   Pst I     Hha I
                                   Fnu4H I  ScrF I                     Msp I
                                   Bbv I    EcoR II   Sau3A I          Hpa II
                                   HinP I   Dsa V     Mbo I            Cfr10 I
                                   Hha I    BstN I    Dpn II           BspW I           Mcr I
                                   BstU I   BstK I    Dpn I            Bgl I            BsiE I
                          Alu I    | ||  || |  ||                       ||              Taq I
                          |              ||    |                                         ||
             GGCTACCGAGCTGAACAACGCGCTGCAGAACCTGGCGCGGACGATCAGCGAAGCGGTCAGGCAATGGCTTCGACCGAAG  1120
             CCGATGGCTCGACTTGTTGCGCGACGTCTTGGACCGCGCCTGCTAGTCGCTTCGCCAGTCCGTTACCGAAGCTGGCTTC
              |·       ||·||   |    ·|      ||    |      ·         ||                 ·
              1049     1059   1071         1083        1093                 1111
                         1060   1071         1083        1093                 1112
                              1060  1071         1083       1093                1112
                                   1062  1071                 1094
                                   1062  1071                 1094
                                      1063   1075
                                      1063   1075
                                         1066  1076
                                                                 Sau3A I
                                                                 Mbo I
                                                                 Dpn II
                                 Bsr I                           Dpn I         BsiY I
                             Mae III                             Alw I        Taq I
                             Mae II  Fok I        BspW I  BstU I  ||            |  |
                             | |     |             |       |                    |
             GCAACGTCACTGGGATGTTCGCATAGGGCAACGCCGAGTTCGCGTAGAATAGCGAAACACGGGATCGGGCGAGTTCGACC  1200
             CGTTGCAGTGACCCTACAAGCGTATCCCGTTGCGGCTCAAGCGCATCTTATCGCTTTGTGCCCTAGCCCGCTCAAGCTGG
              |  |·                 ·|        ·|       ·              ·||          ·|·
              1124   1133             1153   1161                      1182        1195
                 1126                                                    1183        1199
                    1129                                                 1183
                                                                         1183
                                                                         1183
                                                                                 Sau3A I
                                                                                 Mbo I
                                                                    Hae III      Dpn II
                                                                    Mcr I        Dpn I
                                                                    Gdi II       Alw I
                                                                    Eag I        Nla IV
                                                                    Eae I        BstY I
                                                BsmA I           HinP I   Mnl I   BsiE I      BamH I
                                                Bsa I            Hha I   Dde I   Fnu4H I    Alw I
                                                | |    Mae II            |       Nla III    Mnl I
                                                |      |                 |       |   |||
             TTCCGTCGGTCTCGCCCTTTCTCGTGTTTATACGTTTGAGCGCACTCTGAGAGGTTGTCATGGCGGCCGACTACGAggat  1280
             AAGGCAGCCAGAGCGGGAAAGAGCACAAATATGCAAACTCGCGTGAGACTCTCCAACAGTACCGCCGGCTGATGCTcctat
              ||·                  ·|           |       | ·|        |·  |||         |  ||·
              1208                 1232         1240    1247         1259            1275
                 1209                              1240              1251           1263     1277
                                                                                     1264     1277
                                                                                     1264     1277
                                                                                     1264     1278
                                                                                     1264     1278
                                                                                     1264     1278
                                                                                        1265  1278
                                                                                              1278 cc  1282
         gg

Restriction Endonucleases site usage.

Aat II    1     BssH II    1     Hga I      2     Pml I     -
         Acc I     1     BstB I     -     HgiA I     1     PpuM I    -
```

— 81 —

```
Afl II      -       BstE II     -       Hha I      17      PshA I     -
Afl III     -       BstK I      16      Hinc II     2      Pst I      1
Age I       -       BstN I      10      Hind III    -      Pvu I      -
Aha II      4       BstU I      15      Hinf I      2      Pvu II     1
Alu I       4       BstX I       1      HinP I     17      Rma I      -
Alw I       6       BstY I       3      Hpa I       -      Rsa I      2
AlwN I      3       Bsu36 I      -      Hpa II     15      Rsr II     -
Apa I       -       Cfr10 I      6      Hph I       4      Sac I      1
ApaL I      -       Cla I        -      Kas I       1      Sac II     2
Ase I       -       Csp6 I       2      Kpn I       1      Sal I      1
Asp718      1       Dde I        2      Mae II      4      Sap I      -
Ava I       4       Dpn I        9      Mae III     4      Sau3A I    9
Ava II      1       Dpn II       9      Mbo I       9      Sau96 I    8
Avr II      -       Dra I        -      Mbo II      5      Sca I      -
BamH I      1       Dra III      -      Mcr I       3      ScrF I    16
Ban I       5       Drd I        -      Mlu I       -      SfaN I     2
Ban II      1       Dsa I        3      Mme I       -      Sfe I      1
Bbe I       1       Dsa V       16      Mnl I      16      Sfi I      2
Bbs I       3       Eae I        3      Msc I       -      SgrA I     1
Bbv I       7       Eag I        2      Mse I       -      Sma I      2
BceF I      3       Ear I        1      Msp I      15      Sna I      -
Bcl I       -       Ecl136 I     1      Nae I       3      SnaB I     -
Bcn I       6       Eco47 III    -      Nar I       1      Spe I      -
Bgl I       5       Eco57 I      -      Nci I       6      Sph I      -
Bgl II      1       EcoN I       3      Nco I       -      Spl I      -
Bsa I       1       EcoO109 I    1      Nde I       -      Sse8337 I  -
BsaA I      -       EcoR I       -      Nhe I       -      Ssp I      1
BsaB I      -       EcoR II     10      Nla III     3      Stu I      -
BsaJ I     12       EcoR V       -      Nla IV      9      Sty I      -
Bsg I       -       Ehe I        1      Not I       -      Swa I      -
BsiE I      3       Esp I        -      Nru I       -      Taq I     11
BsiY I     10       Fau I        6      Nsi I       -      Tfi I      -
Bsm I       -       Fse I        -      Nsp I       -      Tth111 I   -
BsmA I      2       Fnu4H I     24      Nsp7524 I   -      Tth111 II  -
Bsp120 I    -       Fok I        2      NspB II     7      Xba I      -
Bsp1286 I   1       Fsp I        -      NspC I      -      Xca I      -
BspE I      -       Gdi II       3      Pac I       -      Xcm I      2
BspH I      -       Gsu I        -      PaeR7 I     1      Xho I      1
BspM I      3       Hae I        -      PflM I      1      Xma I      2
BspW I     19       Hae II       2      Ple I       2      Xmn I      -
Bsr I       5       Hae III     14
```

```
Enzyme      Site            Use    Site position (Fragment length) Fragment order Aat II      gacgt/c          1       1(   10) 2     11( 1272) 1
Acc I       gt/mkac          1       1(  621) 2    622(  661) 1
Asp718      g/gtacc          1       1(    0) 2      1( 1282) 1
Ava II      g/gwcc           1       1(  299) 2    300(  983) 1
BamH I      g/gatcc          1       1( 1276) 1   1277(    6) 2
Ban II      grgcy/c          1       1(  429) 2    430(  853) 1
Bbe I       ggcgc/c          1       1(  284) 2    285(  998) 1
Bgl II      a/gatct          1       1(  734) 1    735(  548) 2
Bsa I       ggtctc      1/5  1       1( 1207) 1   1208(   75) 2
Bsp1286 I   gdgch/c          1       1(  429) 2    430(  853) 1
BssH II     g/cgcgc          1       1(  157) 2    158( 1125) 1
BstX I      ccannnnn/ntgg    1       1(  480) 2    481(  802) 1
Ear I       ctcttc      1/4  1       1(  413) 2    414(  869) 1
Ecl136 I    gag/ctc          1       1(  429) 2    430(  853) 1
EcoO109 I   rg/gnccy         1       1(  130) 2    131( 1152) 1
Ehe I       ggc/gcc          1       1(  284) 2    285(  998) 1
HgiA I      gwgcw/c          1       1(  429) 2    430(  853) 1
Kas I       g/gcgcc          1       1(  284) 2    285(  998) 1
Kpn I       ggtac/c          1       1(    0) 2      1( 1282) 1
Nar I       gg/cgcc          1       1(  284) 2    285(  998) 1
PaeR7 I     c/tcgag          1       1(  771) 1    772(  511) 2
PflM I      ccannnn/ntgg     1       1(  109) 2    110( 1173) 1
Pst I       ctgca/g          1       1( 1062) 1   1063(  220) 2
Pvu II      cag/ctg          1       1(  215) 2    216( 1067) 1
Sac I       gagct/c          1       1(  429) 2    430(  853) 1
Sal I       g/tcgac          1       1(  621) 2    622(  661) 1
Sfe I       c/tryag          1       1( 1062) 1   1063(  220) 2
SgrA I      cr/ccggyg        1       1(   37) 2     38( 1245) 1
Ssp I       aat/att          1       1(  745) 1    746(  537) 2
Xho I       c/tcgag          1       1(  771) 1    772(  511) 2

BsmA I      gtctc       1/5  2       1(  211) 2    212(  997) 1   1209(   74) 3
Csp6 I      g/tac            2       1(    1) 3      2( 1006) 1   1008(  275) 2
Dde I       c/tnag           2       1(  213) 2    214( 1033) 1   1247(   36) 3
Eag I       c/ggccg          2       1(  668) 1    669(  595) 2   1264(   19) 3
Fok I       ggatg       9/13 2       1(  110) 3    111( 1022) 1   1133(  150) 2
Hae II      rgcgc/y          2       1(  284) 3    285(  514) 1    799(  484) 2
Hga I       gacgc       5/10 2       1(  761) 1    762(  271) 2   1033(  250) 3
Hinc II     gty/rac          2       1(  190) 3    191(  431) 2    622(  661) 1
Hinf I      g/antc           2       1(  164) 3    165(  455) 1    620(  663) 2
Ple I       gagtc       4/5  2       1(  164) 3    165(  455) 1    620(  663) 2
Rsa I       gt/ac            2       1(   17) 3      2( 1006) 1   1008(  275) 2
Sac II      ccgc/gg          2       1(  680) 1    681(  215) 3    896(  387) 2
SfaN I      gcatc       5/9  2       1(  247) 3    248(  294) 2    542(  741) 1
Sfi I       ggccnnnn/nggcc   2       1(  457) 2    458(  212) 3    670(  613) 1
```

| Enzyme | Site | | # | | | | | | | | | |
|---|---|---|---|---|---|---|---|---|---|---|---|---|
| Sma I | ccc/ggg | | 2 | 1( | 346) 2 | 347( | 116) 3 | 463( | 820) 1 | | | |
| Xcm I | ccannnnn/nnnnctgg | | 2 | 1( | 109) 3 | 110( | 233) 2 | 143( | 940) 1 | | | |
| Xma I | c/ccggg | | 2 | 1( | 346) 2 | 347( | 116) 3 | 463( | 820) 1 | | | |
| AlwN I | cagnnn/ctg | | 3 | 1( | 796) 1 | 797( | 161) 3 | 958( | 108) 4 | 1066( | 217) 2 | |
| Ebs I | gaagac | 2/6 | 3 | 1( | 389) 2 | 390( | 82) 3 | 472( | 63) 4 | 535( | 748) 1 | |
| BceF I | acggc | 12/13 | 3 | 1( | 625) 1 | 626( | 42) 4 | 668( | 371) 2 | 1039( | 244) 3 | |
| BsiE I | cgry/cg | | 3 | 1( | 668) 1 | 669( | 443) 2 | 1112( | 152) 3 | 1264( | 19) 4 | |
| BspM I | acctgc | 4/8 | 3 | 1( | 179) 3 | 180( | 386) 2 | 566( | 63) 4 | 629( | 654) 1 | |
| BstY I | r/gatcy | | 3 | 1( | 581) 1 | 582( | 153) 3 | 735( | 542) 2 | 1277( | 6) 4 | |
| Dsa I | c/crygg | | 3 | 1( | 680) 1 | 681( | 215) 3 | 896( | 141) 4 | 1037( | 246) 2 | |
| Eae I | y/ggccr | | 3 | 1( | 456) 2 | 457( | 212) 3 | 669( | 595) 1 | 1264( | 19) 4 | |
| EcoN I | cctnn/nnnagg | | 3 | 1( | 173) 4 | 174( | 379) 2 | 553( | 389) 1 | 942( | 341) 3 | |
| Gdi II | yggccg | -5/-1 | 3 | 1( | 456) 2 | 457( | 212) 3 | 669( | 595) 1 | 1264( | 19) 4 | |
| Mcr I | c/grycg | | 3 | 1( | 668) 1 | 669( | 443) 2 | 1112( | 152) 3 | 1264( | 19) 4 | |
| Nae I | gcc/ggc | | 3 | 1( | 250) 3 | 251( | 111) 4 | 362( | 396) 2 | 758( | 525) 1 | |
| Nla III | catg/ | | 3 | 1( | 522) 1 | 523( | 335) 3 | 858( | 401) 2 | 1259( | 24) 4 | |
| Aha II | gr/cgyc | | 4 | 1( 1033( | 10) 5 250) 4 | 11( | 274) 2 | 285( | 476) 1 | 761( | 272) 3 | |
| Alu I | ag/ct | | 4 | 1( 1049( | 216) 3 234) 2 | 217( | 214) 4 | 431( | 540) 1 | 971( | 78) 5 | |
| Ava I | c/ycgrg | | 4 | 1( 772( | 346) 2 511) 1 | 347( | 116) 4 | 463( | 91) 5 | 554( | 218) 3 | |
| Hph I | ggtga | 8/7 | 4 | 1( 427( | 7) 5 856) 1 | 8( | 237) 2 | 245( | 30) 4 | 275( | 152) 3 | |
| Mae II | a/cgt | | 4 | 1( 1232( | 11) 5 51) 4 | 12( | 913) 1 | 925( | 199) 2 | 1124( | 108) 3 | |
| Mae III | /gtnac | | 4 | 1( 1126( | 8) 5 157) 4 | 9( | 267) 2 | 276( | 646) 1 | 922( | 204) 3 | |
| Ban I | g/gyrcc | | 5 | 1( 285( | 0) 6 80) 3 | 1( 365( | 35) 5 918) 1 | 36( | 54) 4 | 90( | 195) 2 | |
| Bgl I | gccnnnn/nggc | | 5 | 1( 671( | 24) 6 422) 1 | 25( 1093( | 57) 5 190) 4 | 82( | 377) 2 | 459( | 212) 3 | |
| Bsr I | actgg | 1/-1 | 5 | 1( 646( | 93) 5 483) 1 | 94( 1129( | 312) 2 154) 4 | 406( | 18) 6 | 424( | 222) 3 | |
| Mbo II | gaaga | 8/7 | 5 | 1( 472( | 386) 2 63) 3 | 387( 535( | 3) 6 748) 1 | 390( | 24) 5 | 414( | 58) 4 | |
| Alw I | ggatc | 4/5 | 6 | 1( 1162( | 125) 4 95) 5 | 126( 1277( | 141) 3 1) 6 | 267( 1278( | 315) 2 5) 6 | 582( | 600) 1 | |
| Bcn I | cc s/gg | | 6 | 1( 455( | 302) 2 8) 5 | 303( 463( | 44) 4 1) 7 | 347( 464( | 1) 6 819) 1 | 348( | 107) 3 | |
| Cfr10 I | r/ccggy | | 6 | 1( 362( | 38) 6 396) 1 | 39( 758( | 191) 3 335) 2 | 230( 1093( | 21) 7 190) 4 | 251( | 111) 5 | |
| Fau I | cccgc | 4/6 | 6 | 1( 662( | 140) 4 165) 3 | 141( 827( | 6) 7 56) 5 | 147( 883( | 49) 6 400) 2 | 196( | 466) 1 | |
| Nci I | cc s/gg | | 6 | 1( 455( | 302) 2 8) 5 | 303( 463( | 44) 4 1) 7 | 347( 464( | 1) 6 819) 1 | 348( | 107) 3 | |
| Bbv I | gcagc | 8/12 | 7 | 1( 793( | 154) 3 74) 7 | 155( 867( | 549) 1 215) 3 | 704( 976( | 86) 5 86) 6 | 790( 1062( | 3) 8 221) 2 | |
| NspB II | cmg/ckg | | 7 | 1( 216( | 98) 4 465) 1 | 99( 681( | 15) 7 215) 3 | 114( 896( | 90) 5 81) 6 | 204( 977( | 12) 8 306) 2 | |
| Sau96 I | g/gncc | | 8 | 1( 300( 777( | 79) 6 14) 9 506) 1 | 80( 314( | 52) 7 152) 3 | 132( 466( | 17) 8 177) 2 | 149( 643( | 151) 4 134) 5 | |
| Dpn I | ga/tc | | 9 | 1( 583( 1183( | 126) 4 24) 9 95) 6 | 127( 607( 1278( | 94) 7 129) 3 5)10 | 221( 736( | 47) 8 347) 1 | 268( 1083( | 315) 2 100) 5 | |
| Dpn II | /gatc | | 9 | 1( 583( 1183( | 126) 4 24) 9 95) 6 | 127( 607( 1278( | 94) 7 129) 3 5)10 | 221( 736( | 47) 8 347) 1 | 268( 1083( | 315) 2 100) 5 | |
| Mbo I | /gatc | | 9 | 1( 583( 1183( | 126) 4 24) 9 95) 6 | 127( 607( 1278( | 94) 7 129) 3 5)10 | 221( 736( | 47) 8 347) 1 | 268( 1083( | 315) 2 100) 5 | |
| Nla IV | ggn/ncc | | 9 | 1( 132( 365( | 0)10 153) 2 912) 1 | 1( 285( 1277( | 35) 6 14) 8 6) 9 | 36( 299( | 54) 3 37) 5 | 90( 336( | 42) 4 29) 7 | |
| Sau3A I | /gatc | | 9 | 1( 583( 1183( | 126) 4 24) 9 95) 6 | 127( 607( 1278( | 94) 7 129) 3 5)10 | 221( 736( | 47) 8 347) 1 | 268( 1083( | 315) 2 100) 5 | |
| BsiY I | ccnnnnn/nngg | | 10 | 1( 135( 676( | 109) 6 39) 8 266) 1 | 110( 174( 942( | 4) 8 173) 4 257) 2 | 114( 347( 1199( | 20) 9 206) 3 84) 7 | 134( 553( | 1)11 123) 5 | |
| BstN I | cc/wgg | | 10 | 1( 317( 983( | 4)11 296) 1 28) 9 | 5( 613( 1011( | 21)10 63) 7 60) 8 | 26( 676( 1071( | 148) 4 236) 2 212) 3 | 174( 912( | 143) 5 71) 6 | |
| EcoR II | /ccwgg | | 10 | 1( 317( 983( | 4)11 296) 1 28) 9 | 5( 613( 1011( | 21)10 63) 7 60) 8 | 26( 676( 1071( | 148) 4 236) 2 212) 3 | 174( 912( | 143) 5 71) 6 | |
| Taq I | t/cga | | 11 | 1( 609( 773( | 104) 6 14)11 117) 4 | 105( 623( 890( | 118) 3 106) 5 221) 2 | 223( 729( 1111( | 353) 1 11)12 84) 8 | 576( 740( 1195( | 33) 9 33)10 88) 7 | |
| BsaJ I | c/cnngg | | 12 | 1( 463( 896( | 240) 2 90) 6 16)12 | 241( 553( 912( | 76) 7 122) 4 71) 8 | 317( 675( 983( | 30) 9 6)13 28)10 | 347( 681( 1011( | 116) 5 215) 3 26)11 | |

```
                          1037( 246) 1
Hae III    gg/cc      14     1(  80) 7     81(  51) 9    132(  18)12    150( 165) 3
                           315( 143) 4    458(   9)14    467( 177) 2    644(  26)10
                           670(   9)15    679(  78) 8    757(  21)11    778( 116) 5
                           894(  87) 6    981( 284) 1   1265(  18)13

BscU I     cg/cg      15     1(  70) 7     71(  69) 8    140(   6)14    146(  13)13
                           159(   2)16    161( 198) 3    359(  15)11    374( 279) 1
                           653(   5)15    658(  24) 9    682( 200) 2    882(  15)12
                           897( 162) 4   1059(  17)10   1076(  85) 6   1161( 122) 5

Hpa II     c/cgg      15     1(  39) 7     40( 191) 2    231(  21)10    252(  13)13
                           265(  29) 8    294(   9)14    303(  28) 9    331(  17)11
                           348(  15)12    363(  93) 6    456(   8)15    464(   5)16
                           469( 119) 5    588( 171) 4    759( 335) 1   1094( 189) 3

Msp I      c/cgg      15     1(  39) 7     40( 191) 2    231(  21)10    252(  13)13
                           265(  29) 8    294(   9)14    303(  28) 9    331(  17)11
                           348(  15)12    363(  93) 6    456(   8)15    464(   5)16
                           469( 119) 5    588( 171) 4    759( 335) 1   1094( 189) 3

BscK I     c/cngg     16     1(   4)15      5(  21)12     26( 148) 4    174( 129) 5
                           303(  14)13    317(  30)10    347(   1)16    348( 107) 6
                           455(   8)14    463(   1)17    464( 149) 3    613(  63) 8
                           676( 236) 1    912(  71) 7    983(  28)11   1011(  60) 9
                          1071( 212) 2

Dsa V      /ccngg     16     1(   4)15      5(  21)12     26( 148) 4    174( 129) 5
                           303(  14)13    317(  30)10    347(   1)16    348( 107) 6
                           455(   8)14    463(   1)17    464( 149) 3    613(  63) 8
                           676( 236) 1    912(  71) 7    983(  28)11   1011(  60) 9
                          1071( 212) 2

MnL I      cctc  7/7  16     1(  62) 7     63( 178) 3    241( 158) 4    399(  18)13
                           417(  77) 6    494(  59) 8    553(  10)14    563( 212) 2
                           775(  10)15    785(  22)12    807(  85) 5    892(  47)10
                           939(  10)16    949(  54) 9   1003( 248) 1   1251(  24)11
                          1275(   8)17

ScrF I     cc/ngg     16     1(   4)15      5(  21)12     26( 148) 4    174( 129) 5
                           303(  14)13    317(  30)10    347(   1)16    348( 107) 6
                           455(   8)14    463(   1)17    464( 149) 3    613(  63) 8
                           676( 236) 1    912(  71) 7    983(  28)11   1011(  60) 9
                          1071( 212) 2

Hha I      gcg/c      17     1(  71) 8     72(  67) 9    139(   6)16    145(  13)15
                           158(   2)18    160(  18)12    178( 108) 5    286(  74) 7
                           360(  15)13    375( 277) 1    652(   5)17    657(  34)11
                           691( 109) 4    800( 105) 6    905( 155) 3   1060(  15)14
                          1075( 165) 2   1240(  43)10

HinP I     g/cgc      17     1(  71) 8     72(  67) 9    139(   6)16    145(  13)15
                           158(   2)18    160(  18)12    178( 108) 5    286(  74) 7
                           360(  15)13    375( 277) 1    652(   5)17    657(  34)11
                           691( 109) 4    800( 105) 6    905( 155) 3   1060(  15)14
                          1075( 165) 2   1240(  43)10

BspW I     gcnnnnn/nngc 19    1(  24)13     25(   9)15     34(   3)19     37(  45)11
                            82(  69) 9    151( 104) 5    255(  82) 8    337(  25)12
                           362(   4)18    366(  93) 7    459( 186) 2    645(  17)14
                           662(   9)16    671(   3)20    674( 119) 4    793(   9)17
                           802(  96) 6    898( 195) 1   1093(  60)10   1153( 130) 3

Fnu4H I    gc/ngc     24     1(  33)12     34(   9)19     43(   3)22     46(  23)16
                            69(  86) 4    155(  48)10    203(  52) 9    255(  33)13
                           288(  46)11    334( 211) 1    545( 109) 3    654(   5)21
                           659(  12)18    671(   9)20    680(  24)15    704(  86) 5
                           790(   3)23    793(  74) 8    867(  28)14    895(   3)24
                           898(  78) 7    976(   3)25    979(  83) 6   1062( 201) 2
                          1263(  20)17

497 sites found

No Sites found for the following Restriction Endonucleases

Afl II    c/ttaag         EcoR I   g/aattc         Pml I    cac/gtg
Afl III   a/crygt         EcoR V   gat/atc         PpuM I   rg/gwccy
Age I     a/ccggt         Esp I    gc/tnagc        PshA I   gacnn/nngtc
Apa I     gggcc/c         Fse I    ggccgg/cc       Pvu I    cgat/cg
ApaL I    g/tgcac         Fsp I    tgc/gca         Rma I    c/tag
Ase I     at/taat         Gsu I    ctggag  16/14   Rsr II   cg/gwccg
Avr II    c/ctagg         Hae I    wgg/ccw         Sap I    gcttctc  1/4
Bcl I     t/gatca         Hind III a/agctt         Sca I    agt/act
BsaA I    yac/gtr         Hpa I    gtt/aac         Sna I    gta/tac
BsaB I    gatnn/nnatc     Mlu I    a/cgcgt         SnaB I   tac/gta
Bsg I     gtgcag  16/14   Mme I    tccrac  20/18   Spe I    a/ctagt
Bsm I     gaatgc  1/-1    Msc I    tgg/cca         Sph I    gcatg/c
Bsp120 I  g/ggccc         Mse I    t/taa           Spl I    c/gtacg
BspE I    t/ccgga         Nco I    c/catgg         Sse8337 I cctgca/gg
BspH I    t/catga         Nde I    ca/tatg         Stu I    agg/cct
BstB I    tt/cgaa         Nhe I    g/ctagc         Sty I    c/cwwgg
BstE II   g/gtnacc        Not I    gc/ggccgc       Swa I    attt/aaat
Bsu36 I   cc/tnagg        Nru I    tcg/cga         Tfi I    g/awtc
Cla I     at/cgat         Nsi I    atgca/t         Tth111 I  gacn/nngtc
Dra I     ttt/aaa         Nsp I    rcatg/y         Tth111 II caarca  11/9
```

- 84 -

| | | | | | |
|---|---|---|---|---|---|
| Dra III | cacnnn/gtg | Nsp7524 I | r/catgy | Xba I | t/ctaga |
| Drd I | gacnnnn/nngtc | NspC I | rcatg/y | Xca I | gta/tac |
| Eco47 III | agc/gct | Pac I | ttaat/taa | Xmn I | gaann/nnttc |
| Eco57 I | ctgaag 16/14 | | | | |

Annex III

855 bp DNA insert of plasmid pPX1

```
                                           Fnu4H I
                                           Hin? I                    Scrf I
                                           Hha I                     Nci I
                              SauJA I      Nla IV                    Msp I
                   Fnu4H I    Mbo I        Nar I                     Hpa II
                   BspW I     Dpn II       Yas I                     Osa V
              Msp I           Msp I        Hae II          Sau96 I
              Nae I Fnu4H I   Alw I        Phe I           Ava II
         Hph I Hpa II         Fnu4H I      Bhe I           Nla IV
     Mnl I StaN I   Bbv I     Hpa II       Ban I    Msp I  BscK I
     BsaJ I Cfr10 I Bbv I     Dpn I        Aha II   Hpa II Bcn I      Sau96 I
     |   |    | |    | |        | |          | |     | |     |          |
 TTGCCCCCTCGGTGATGCCGGCGGCTGCTGCCGGATGGTCGGCGACGGGTGGGCCCGCTCCGGTGGGTCCGGGAGCGATG 320
 AACGGGGGAGCCACTACGGCCGCCGACGACGGCCTAGCAGCCGCTGCCCACCGCGGCGAGGGCCACCCAGGGCCTCGCTAC
     |   |    | |    | |        | |          | |     | |     |          |
     247  257   267  274        291         300     309                 320
     247  254   264  271        291         300     309
         251    258  267        291                 305
              258    264  273   291                 306
                     261  274   291                 306
                          274   291                 309
                          274   291                 309
                                291                 309
                                292                 309
                                292                 309
                                294
```

```
                                   Scrf I
                                   Nci I
                                   Msp I
                                   Hpa II                BspW I
                                   Osa V                 Nla IV
                                   BscK I                Ban I
                      Fsp I        Bcn I                 Msp I
         Scrf I                    Xcm I                 Hpa II
         EcoR II                   Scrf I                Nae I
         Osa V  Hin? I             EcoR II               Cfr10 I
         BscN I         Nla IV     Hae III     Hin? I              Hin? I
         BscK I         Fnu4H I    Osa V       Hha I     Hin? I    Mbo II
         BsaJ I         Msp I      BscK I      BscU I    BscU I    Mbo II
    Hae III Hha I       Hpa II     BscK I      | | |     | |       Bbs I
     | |   |              |          |           |         |         |
 GGCCAGGGTCGCGCAATCCGGCGGCTCCACCAGGCCGGGTCTGGTCGGCGGCCACCGCTCGCGCAGGAGCCGTGAAGAAGA 400
 CCGGTCCCAGCGCGTTAGGCCGCCGAGGTGGTCCGGCCCAGACCAGCCGCCCGGTGGCGAGCGCGTCCTCGGCACTTCTTCT
     |   |        |         |          |          |         |         |
     321 330      337       349        365        380       393
     323          337       349        366        381       395
     323             340    349        366        381       395
     323                342 352        368
     323                      349      368
     323          330        349       368
     323                                369
              329                       369
                                        354
                                        354       371
                                        354       371
                                        354       372
                                        354
                                        354
                                        354
```

```
                                                                    ScrF I
                                                                    Nci I
                                                                    Msp I
                                                                    Hpa II
                                                                    Osa V
                                                                    Xma I
                                                                    Sma I
                                                                    ScrF I
                                                              BspW I
                                                                Bgl I      Msp I
                                                                Sfi I      Hpa II
                                                                Hae III  Hae III
                                                              Gdi II    Sau96 I
                                                                Eae I    BscK I
                                     Sac I                     Msp I     Nci I
                                     HgiA I                    Hpa II    Bcn I
                                     Ecl136 I                  ScrF I    Osa V
                                     Bsp1296 I                 Nci I     BscK I
                                     Ban II                    Osa V     BsaJ I
                   Mbo II          Hph I                       BscK I    Bcn I      Mbo II
    Mnl I    Bsc I  Eac I    Bsr I  Alu I                      Bcn I     Ava I      Bbs I
    |   |    |    |  |   |    |   |  |                         |||||     |  |  |    |  |
CGACGAGGACGACTGGGACGAAGAGGACGACTGGTGAGCTCCCGTAATGACAACAGACTTCCCGGCCACCCGGGCCGGAA   480
GCTGCTCCTGCTGACCCTGCTTCTCCTGCTGACCACTCGAGGGCATTACTGTTGTCTGAAGGGCCGGTGGGCCCGGCCTT
 |   |    |    |   |    |    . | .|||     ||      |   |    .
 405  412 420  430 437            461       469     478
              420 423            436                           461     469      478
                                 436                           461     469
                                 436                           461     469
                                 436                           461     469
                                 436                           462     470
                                                               462     469
                                                               463     470
                                                               463          472
                                                                464         473
                                                                464         475
                                                                 465        475
                                                                  465
                                                                      469
                                                                      469
                                                                      469
                                                                        470
                                                                        470
                                                                        470
                                                                        470
                                                                        470

Mnl I
                                                                          EcoN I
                                                                       BspW I
                                                                 Mbo II  Fnu4H I
     BsrX I          Mnl I                      Nla III       Bbs I  StaN I     BsiY I
     |                 |                          |             |   |  |          |
 CACTTGCCAACATTTTGGGCGAGGAAGGTAAAGAGAGAAAGTAGTCCAGCATGGCAGAGATGAAGACCGATGCCGCTACCC  560
 GTGAACGGTTGTAAAACCGCTCCTTCCATTTCTCTCTTTCATCAGGTCGTACCGTCTCTACTTCTGGCTACGGCGATGGG
  ||    |    .  |    .   |    |    .   |.      |        |    . |  .|        |   |.
  487        500                                 529            541    548       559
                                                                541    551
                                                                        554
                                                                              559
                                                                              559

ScrF I
                                                             EcoR II
                                                             Osa V
                                     Msp I                   BstN I
                                     Hpa II                  BscK I       Bce F I
                                     SauJA I           Taq I              Taq I
                    Mnl I            Mbo I             Taq I              Sal I
       Hin P I                       Dpn II            SauJA I            Hinc II
       Hha I                         BscY I            Mbo I              Acc I
       BspW I                        Alw I             Dpn II             Ple I
    BscU I   BspM I     Taq I        Dpn I             Dpn I              Hinf I    BspM I
     ||        |           |        | | | .              |   |         |  | ||| |     |
 TCGCGCAGGAGGCAGGTAAATTTCGAGGCGGATCTCCGGCGACCTGAAAACCCAGATCGACCAGGTGGAGTCGACGGCAGGT  640
 AGCGCGTCCTCCGTCCATTAAAGCTCCGCCTAGAGGCCGCTGGACTTTTGGGTCTAGCTGGTCCACCTCAGCTGCCGTCCA
  ||    |- |     . |   ||| .     | |.         . |  |  |.    | ||  |   |||.  |  |
  562    572       582   589                       613       626       635
  563                    588                       613       626
  563                    588                       613       628
  563                    589                       613       628
              569        589                       615       629
                         589                                 629
                         589                          619    629
                         594  -                       619       632
                         594                          619
                                                      619
                                                      619

-88-
```

```
                                            ScrF I
                                            EcoR II
                                            BsaJ I
                                            BspW I
                                  Fnu4H I            BstU I
                                  BspW I             Sac II
                                  Bgl I              NspB II
                                  Sfi I              Osa I
                        BstU I    Mcr I   Osa V
                        HinP I    Cdi II
               HinP I   Fau I     Sac I   BsaJ I
      Bsr I    Hha I              Eae I   BscN I
      BspW I   Fnu4H I             Bsi2 I            Fnu4H I
      Hae III  BstU I   BspW I  Hae III   Hae III            HinP I     Fnu4H I
      Sau96 I  Hha I    Fnu4H I BceF I    BsiY I             Hha I      Abv I
      ||||     |||  |||  |      ||||  |||  ||||              |          |
TCGTTGCAGGGCCAGTGGCGCGGCGCGGGGGGACGGCCGCCCAGGCCGCCGGTGGTGCGCTTCCAAGAAGCAGCCAATAA 720
AGCAACGTCCCGGTCACCGCGCCGCGCCCCCCTGCCGGCGGGTCCGGCGGCCACCACGCGAAGGTTCTTCGTCGGTTATT
      ||||     |||  |||  |  .   ||||  |||  ||||.             |  .        |
      649      658  665    674       682                     697        710
      650      659     668    676   685                      697        710
      651      660         675   682  686
      652            663     675   682
                     663       675 682
                      664      675   682
                                676  687
                                677  687
                                677  687
                                677     688
                                   680
                                   681
                                   682
                                   682

Taq I                      Hga I          Hae III
                    SauJA I                    Aha II         Sau96 I
                    Mbo I                      Msp I          Mnl I
                    Dpn II                     Hpa II         Taq I                Fnu4H I
                    BstY I                     Nae I          Xho I                Fnu4H I
                    Bgl II                     Cfr10 I        PaeR7 I              BspW I
          Taq I     Dpn I     Ssp I            Hae III        Ava I       Mnl I   Abv I
          ||  |     ||  |     |                |||  ||        ||-|  ||     |       :
GCCAGAAGCAGGAACTCGACGAGATCTCGACGAATATTCGTCAGGCCCGCGTCCAATACTCGAGGGCCGACGAGGAGCAGC 800
CGGTCTTCGTCCTTGAGCTGCTCTAGAGCTGCTTATAAGCAGTCCGGCCGCAGGTTATGAGCTCCCGGCTGCTCCTCGTCG
          .  |     -||      |                |||  ||.        ||-|  ||     |       :
          735       742     752               763            773        791      799
                    741              764                    773        796
                    741                       764           779                  799
                    742                       765           779
                    742                       765           781           799
                    742                       767           783
                           746                 768           784

SauJA I
                                                        Mbo I
                                                        Dpn II
                                                        Dpn I
                                                        Alw I
         BspW I                                         Nla IV
         HinP I                                         BstY I
         Hha I                                          BamH I
         Hae II              Hph I                      Alw I
         AlwN I     Mnl I    |        Hph I   Hph I   Mnl I
         ||  ||     |        |        |       |        ||  ||
AGCAGGCGCTGTCCTCGCAAATGGGCTTcaccatcaccatcaccatcgaggatcc 855
TCGTCCGCGACAGGAGCGTTTACCCGAAgtggtagtggtagtggtagctcctagg
         |  ||  .   |                 |  .  |           ||  ||
         803       813              828    834   840   848
                   805                           850
                   806                           850
                   806                           850
                   808                           850
                                                 851
                                                 851
                                                 851
                                                 851
                                                 851
                                                 851

Restriction Endonucleases site usage

Aat II     1    BssH II    1     Hga I      1     Pml I     -
Acc I      1    BstB I     -     HgiA I     1     PpuM I    -
Afl II     -    BscE II    -     Hha I     15     PshA I    -
Afl III    -    BscK I    12     Hinc II    2     Pst I     -
Age I      -    BstN I     7     Hind III   -     Pvu I     -
Aha II     3    BstU I    11     Hinf I     2     Pvu II    1
Alu I      2    BscX I     1     HinP I    15     Rma I     -
Alw I      7    BstY I     4     Hpa I      -     Rsa I     1
AlwN I     1    Bsu36 I    -     Hpa II    15     Rsr II    -
Apa I      -    Cfr10 I    5     Hph I      6     Sac I     1
ApaL I     -    Cla I      -     Kas I      1     Sac II    1
Ase I      -    Csp6 I     1     Kpn I      1     Sal I     1
```

− 89 −

```
Asp718      1     Dde I         1     Mae II      1     Sap I        -
Ava I       2     Dpn I         8     Mae III     1     Sau3A I      8
Ava II      1     Dpn II        8     Mbo I       8     Sau96 I      8
Avr II      -     Dra I         -     Mbo II      5     Sca I        -
BamH I      2     Dra III       -     Mcr I       1     ScrF I      12
Ban I       5     Drd I         -     Mlu I       -     SfaN I       2
Ban II      1     Dsa I         1     Mme I       -     Sfe I        -
Bbe I       1     Dsa V        12     Mnl I      11     Sfi I        2
Bbs I       3     Eae I         2     Msc I       -     SgrA I       1
Bbv I       6     Eag I         1     Mse I       -     Sma I        1
BceF I      2     Ear I         1     Msp I      15     SnaI         -
Bcl I       -     Ecl136 I      1     Nae I       3     SnaB I       -
Bcn I       5     Eco47 III     -     Nar I       1     Spe I        -
Bgl I       4     Eco57 I       -     Nci I       5     Sph I        -
Bgl II      1     EcoN I        2     Nco I       -     Spl I        -
Bsa I       -     EcoO109 I     1     Nde I       -     Sse8387 I    -
BsaA I      -     EcoR I        -     Nhe I       -     Ssp I        1
BsaB I      -     EcoR II       7     Nla III     1     Stu I        -
BsaJ I      5     EcoR V        -     Nla IV     10     Sty I        -
Bsg I       -     Ehe I         1     Not I       -     Swa I        -
BsiE I      1     Esp I         -     Nru I       -     Taq I        8
BsiY I      8     Fau I         4     Nsi I       -     Tfi I        -
Bsm I       -     Fse I         -     Nsp I       -     Tth111 I     -
BsmA I      1     Fnu4H I      19     Nsp7524 I   -     Tth111 II    -
Bsp120 I    -     Fok I         1     NspB II     -     Xba I        -
Bsp1286 I   1     Fsp I         1     NspC I      -     Xca I        -
BspE I      -     Cdi II        2     Pac I       -     Xcm I        2
BspH I      -     Gsu I         -     PaeR7 I     1     Xho I        1
BspM I      3     Hae I         -     PflM I      1     Xma I        1
BspW I     17     Hae II        2     Ple I       2     Xmn I        -
Bsr I       4     Hae III      12
```

```
Enzyme     Site            Use    Site position (Fragment length) Fragment order Aac II     gacgc/c          1     1(   16) 2    17( 839) 1
Acc I      gt/mkac          1     1(  627) 1   628( 223) 2
AlwN I     cagnnn/ctg       1     1(  802) 1   803(  53) 2
Asp718     g/gtacc          1     1(    6) 2     7( 849) 1
Ava II     g/gwcc           1     1(  305) 2   306( 550) 1
Ban II     grgcy/c          1     1(  435) 1   436( 420) 2
Bbe I      ggcgc/c          1     1(  290) 2   291( 565) 1
Bgl II     a/gatct          1     1(  740) 1   741( 115) 2
BsiE I     cgry/cg          1     1(  674) 1   675( 181) 2
BsmA I     gtctc       1/5  1     1(  217) 2   218( 638) 1
Bsp1286 I  gdgch/c          1     1(  435) 1   436( 420) 2
BssH II    g/cgcgc          1     1(  163) 2   164( 692) 1
BstX I     ccannnnn/ntgg    1     1(  486) 1   487( 369) 2
Csp6 I     g/tac            1     1(    7) 2     8( 848) 1
Dde I      c/tnag           1     1(  219) 2   220( 636) 1
Dsa I      c/crygg          1     1(  686) 1   687( 169) 2
Eag I      c/ggccg          1     1(  674) 1   675( 181) 2
Ear I      ctcttc      1/4  1     1(  419) 2   420( 436) 1
Ecl136 I   gag/ctc          1     1(  435) 1   436( 420) 2
EcoO109 I  rg/gnccy         1     1(  136) 2   137( 719) 1
Ehe I      ggc/gcc          1     1(  290) 2   291( 565) 1
Fok I      ggatg       9/13 1     1(  116) 2   117( 739) 1
Fsp I      tgc/gca          1     1(  328) 2   329( 527) 1
Hga I      gacgc       5/10 1     1(  767) 1   768(  88) 2
HgiA I     gwgcw/c          1     1(  435) 1   436( 420) 2
Kas I      g/gcgcc          1     1(  290) 2   291( 565) 1
Kpn I      ggtac/c          1     1(    6) 2     7( 849) 1
Mae II     a/cgt            1     1(   17) 2    18( 838) 1
Mae III    /gtnac           1     1(   14) 2    15( 841) 1
Mcr I      c/grycg          1     1(  674) 1   675( 181) 2
Nar I      gg/cgcc          1     1(  290) 2   291( 565) 1
Nla III    catg/            1     1(  528) 1   529( 327) 2
PaeR7 I    c/tcgag          1     1(  777) 1   778(  78) 2
PflM I     ccannnn/ntgg     1     1(  115) 2   116( 740) 1
Pvu II     cag/ctg          1     1(  221) 2   222( 634) 1
Rsa I      gt/ac            1     1(    7) 2     8( 848) 1
Sac I      gagct/c          1     1(  435) 1   436( 420) 2
Sac II     ccgc/gg          1     1(  686) 1   687( 169) 2
Sal I      g/tcgac          1     1(  627) 1   628( 228) 2
SgrA I     cr/ccggyg        1     1(   43) 2    44( 812) 1
Sma I      ccc/ggg          1     1(  468) 1   469( 387) 2
Ssp I      aat/att          1     1(  751) 1   752( 104) 2
Xho I      c/tcgag          1     1(  777) 1   778(  78) 2
Xma I      c/ccggg          1     1(  468) 1   469( 387) 2

Alu I      ag/ct            2     1(  222) 2   223( 214) 3   437( 419) 1
Ava I      c/ycgrg          2     1(  468) 1   469( 309) 2   778(  78) 3
BamH I     g/gatcc          2     1(    0) 3     1( 849) 1   850(   6) 2
BceF I     acggc      12/13 2     1(  631) 1   632(  42) 3   674( 182) 2
Eae I      y/ggccr          2     1(  462) 1   463( 212) 2   675( 181) 3
EcoN I     cctnn/nnagg      2     1(  179) 3   180( 379) 1   559( 297) 2
Gdi II     yggccg      -5/-1 2    1(  462) 1   463( 212) 2   675( 181) 3
Hae II     rgcgc/y          2     1(  290) 2   291( 514) 1   805(  51) 3
Hinc II    gty/rac          2     1(  196) 3   197( 431) 1   628( 228) 2
Hinf I     g/antc           2     1(  170) 3   171( 455) 1   626( 230) 2
```

- 90 -

| Ple I | gagtc | 4/5 | 2 | 1( 170) 3 | 171( 455) 1 | 626( 230) 2 | | |
|---|---|---|---|---|---|---|---|---|
| ScaN I | gcatc | 5/9 | 2 | 1( 253) 3 | 254( 294) 2 | 548( 308) 1 | | |
| Sfi I | ggcnnnn/nggcc | | 2 | 1( 463) 1 | 464( 212) 2 | 676( 130) 3 | | |
| Xcm I | ccannnnn/nnnntgg | | 2 | 1( 115) 3 | 116( 233) 2 | 349( 507) 1 | | |
| Aha II | gr/cgyc | | 3 | 1( 16) 4 | 17( 274) 2 | 291( 476) 1 | 767( 89) 3 | |
| Bbs I | gaagac | 2/6 | 3 | 1( 395) 1 | 396( 82) 3 | 478( 63) 4 | 541( 115) 2 | |
| BspM I | acctgc | 4/8 | 3 | 1( 185) 3 | 186( 386) 1 | 572( 63) 4 | 635( 221) 2 | |
| Nae I | gcc/ggc | | 3 | 1( 256) 2 | 257( 111) 3 | 368( 396) 1 | 764( 92) 4 | |
| Bgl I | gccnnnn/nggc | | 4 | 1( 30) 5 | 31( 57) 4 | 88( 377) 1 | 465( 212) 2 | |
| | | | | 677( 179) 3 | | | | |
| Bsr I | actgg | 1/-1 | 4 | 1( 99) 4 | 100( 312) 1 | 412( 18) 5 | 430( 222) 2 | |
| | | | | 652( 204) 3 | | | | |
| BscY I | r/gatcy | | 4 | 1( 0) 5 | 1( 587) 1 | 588( 153) 2 | 741( 109) 3 | |
| | | | | 850( 6) 4 | | | | |
| Fau I | cccgc | 4/6 | 4 | 1( 146) 3 | 147( 6) 5 | 153( 49) 4 | 202( 466) 1 | |
| | | | | 668( 188) 2 | | | | |
| Ban I | g/gyrcc | | 5 | 1( 6) 6 | 371( 485) 1 | 42( 54) 4 | 96( 195) 2 | |
| | | | | 291( 80) 3 | | | | |
| Bcn I | cc s/gg | | 5 | 1( 308) 2 | 309( 45) 4 | 354( 107) 3 | 461( 8) 5 | |
| | | | | 469( 1) 6 | 470( 386) 1 | | | |
| BsaJ I | c/cnngg | | 5 | 1( 246) 1 | 247( 76) 5 | 323( 146) 4 | 469( 212) 2 | |
| | | | | 681( 6) 6 | 687( 169) 3 | | | |
| Cfr10 I | r/ccggy | | 5 | 1( 44) 5 | 45( 191) 2 | 236( 21) 6 | 257( 111) 3 | |
| | | | | 368( 396) 1 | 764( 92) 4 | | | |
| Mbo II | gaaga | 8/7 | 5 | 1( 392) 1 | 393( 3) 6 | 396( 24) 5 | 420( 58) 4 | |
| | | | | 478( 63) 3 | 541( 315) 2 | | | |
| Nci I | cc/sgg | | 5 | 1( 308) 2 | 309( 45) 4 | 354( 107) 3 | 461( 8) 5 | |
| | | | | 469( 1) 6 | 470( 386) 1 | | | |
| NspB II | cmg/ckg | | 5 | 1( 104) 3 | 105( 15) 5 | 120( 90) 4 | 210( 12) 6 | |
| | | | | 222( 465) 1 | 687( 169) 2 | | | |
| Bbv I | gcagc | 8/12 | 6 | 1( 160) 2 | 161( 103) 3 | 264( 3) 6 | 267( 443) 1 | |
| | | | | 710( 86) 4 | 796( 3) 7 | 799( 57) 5 | | |
| Hph I | ggtga | 8/7 | 6 | 1( 13) 5 | 14( 237) 2 | 251( 182) 3 | 433( 395) 1 | |
| | | | | 828( 6) 6 | 834( 6) 7 | 840( 16) 4 | | |
| Alw I | ggatc | 4/5 | 7 | 1( 0) 8 | 1( 1) 6 | 2( 130) 4 | 132( 141) 3 | |
| | | | | 273( 315) 1 | 588( 262) 2 | 850( 1) 7 | 851( 5) 5 | |
| BstN I | cc/wgg | | 7 | 1( 10) 8 | 11( 21) 7 | 32( 148) 3 | 180( 143) 4 | |
| | | | | 323( 26) 6 | 349( 270) 1 | 619( 63) 5 | 682( 174) 2 | |
| EcoR II | /ccwgg | | 7 | 1( 10) 8 | 11( 21) 7 | 32( 148) 3 | 180( 143) 4 | |
| | | | | 323( 26) 6 | 349( 270) 1 | 619( 63) 5 | 682( 174) 2 | |
| BsiY I | ccnnnnn/nngg | | 8 | 1( 4) 7 | 5( 111) 4 | 116( 4) 8 | 120( 20) 6 | |
| | | | | 140( 1) 9 | 141( 39) 5 | 180( 179) 1 | 559( 123) 3 | |
| | | | | 682( 174) 2 | | | | |
| Dpn I | ga/tc | | 8 | 1( 1) 9 | 2( 131) 2 | 133( 94) 5 | 227( 47) 6 | |
| | | | | 274( 315) 1 | 589( 24) 7 | 613( 129) 3 | 742( 109) 4 | |
| | | | | 851( 5) 8 | | | | |
| Dpn II | /gatc | | 8 | 1( 1) 9 | 2( 131) 2 | 133( 94) 5 | 227( 47) 6 | |
| | | | | 274( 315) 1 | 589( 24) 7 | 613( 129) 3 | 742( 109) 4 | |
| | | | | 851( 5) 8 | | | | |
| Mbo I | /gatc | | 8 | 1( 1) 9 | 2( 131) 2 | 133( 94) 5 | 227( 47) 6 | |
| | | | | 274( 315) 1 | 589( 24) 7 | 613( 129) 3 | 742( 109) 4 | |
| | | | | 851( 5) 8 | | | | |
| Sau3A I | /gatc | | 8 | 1( 1) 9 | 2( 131) 2 | 133( 94) 5 | 227( 47) 6 | |
| | | | | 274( 315) 1 | 589( 24) 7 | 613( 129) 3 | 742( 109) 4 | |
| | | | | 851( 5) 8 | | | | |
| Sau96 I | g/gncc | | 8 | 1( 85) 5 | 86( 52) 7 | 138( 17) 8 | 155( 151) 3 | |
| | | | | 306( 14) 9 | 320( 152) 2 | 472( 177) 1 | 649( 134) 4 | |
| | | | | 783( 73) 6 | | | | |
| Taq I | t/cga | | 8 | 1( 110) 3 | 111( 118) 2 | 229( 353) 1 | 582( 33) 6 | |
| | | | | 615( 14) 8 | 629( 106) 4 | 735( 11) 9 | 746( 33) 7 | |
| | | | | 779( 77) 5 | | | | |
| Nla IV | ggn/ncc | | 10 | 1( 0)11 | 1( 6) 9 | 7( 35) 6 | 42( 54) 3 | |
| | | | | 96( 42) 4 | 138( 153) 2 | 291( 14) 8 | 305( 37) 5 | |
| | | | | 342( 29) 7 | 371( 479) 1 | 850( 6)10 | | |
| BstU I | cg/cg | | 11 | 1( 76) 5 | 77( 69) 6 | 146( 6)10 | 152( 13) 9 | |
| | | | | 165( 2)12 | 167( 198) 1 | 365( 15) 8 | 380( 182) 2 | |
| | | | | 562( 97) 4 | 659( 5)11 | 664( 24) 7 | 688( 168) 3 | |
| Mnl I | cctc | 7/7 | 11 | 1( 68) 5 | 69( 178) 2 | 247( 158) 3 | 405( 18) 9 | |
| | | | | 423( 77) 4 | 500( 59) 6 | 559( 10)10 | 569( 212) 1 | |
| | | | | 781( 10)11 | 791( 22) 8 | 813( 35) 7 | 848( 8)12 | |
| BscK I | c/cngg | | 12 | 1( 10)10 | 11( 21) 8 | 32( 148) 3 | 180( 129) 4 | |
| | | | | 309( 14) 9 | 323( 26) 7 | 349( 5)12 | 354( 107) 5 | |
| | | | | 461( 8)11 | 469( 1)13 | 470( 149) 2 | 619( 63) 6 | |
| | | | | 682( 174) 1 | | | | |
| Bsa V | /ccngg | | 12 | 1( 10)10 | 11( 21) 8 | 32( 148) 3 | 180( 129) 4 | |
| | | | | 309( 14) 9 | 323( 26) 7 | 349( 5)12 | 354( 107) 5 | |
| | | | | 461( 8)11 | 469( 1)13 | 470( 149) 2 | 619( 63) 6 | |
| | | | | 682( 174) 1 | | | | |
| Hae III | gg/cc | | 12 | 1( 86) 4 | 87( 51) 7 | 138( 18)11 | 156( 165) 2 | |
| | | | | 321( 31) 8 | 352( 112) 3 | 464( 9)12 | 473( 177) 1 | |
| | | | | 650( 26) 9 | 676( 9)13 | 685( 78) 5 | 763( 21)10 | |
| | | | | 784( 72) 6 | | | | |
| ScrF I | cc/ngg | | 12 | 1( 10)10 | 11( 21) 8 | 32( 148) 3 | 180( 129) 4 | |
| | | | | 309( 14) 9 | 323( 26) 7 | 349( 5)12 | 354( 107) 5 | |

- 91 -

| Enzyme | Site | Length | Positions | | | | | | | |
|---|---|---|---|---|---|---|---|---|---|---|
| | | | 461( | 8)11 | 469( | 1)13 | 470( | 149) 2 | 619( | 63) 6 |
| | | | 682( | 174) 1 | | | | | | |
| Hha I | gcg/c | 15 | 1( | 77) 5 | 73( | 67) 6 | 145( | 6)14 | 151( | 13)13 |
| | | | 164( | 2)16 | 166( | 18)11 | 184( | 108) 3 | 292( | 38) 8 |
| | | | 330( | 16) 9 | 366( | 15)12 | 381( | 132) 1 | 563( | 95) 4 |
| | | | 658( | 5)15 | 663( | 34)10 | 697( | 109) 2 | 806( | 50) 7 |
| Hin9 I | g/cgc | 15 | 1( | 77) 5 | 73( | 67) 6 | 145( | 6)14 | 151( | 13)13 |
| | | | 164( | 2)16 | 166( | 18)11 | 184( | 108) 3 | 292( | 38) 8 |
| | | | 330( | 16) 9 | 366( | 15)12 | 381( | 132) 1 | 563( | 95) 4 |
| | | | 658( | 5)15 | 663( | 34)10 | 697( | 109) 2 | 806( | 50) 7 |
| Hpa II | c/cgg | 15 | 1( | 4)16 | 5( | 41) 6 | 46( | 191) 1 | 237( | 21) 9 |
| | | | 258( | 13)12 | 271( | 29) 7 | 300( | 9)13 | 309( | 28) 8 |
| | | | 337( | 17)10 | 354( | 15)11 | 369( | 93) 4 | 462( | 8)14 |
| | | | 470( | 5)15 | 475( | 119) 3 | 594( | 171) 2 | 765( | 91) 5 |
| Msp I | c/cgg | 15 | 1( | 4)16 | 5( | 41) 6 | 46( | 191) 1 | 237( | 21) 9 |
| | | | 258( | 13)12 | 271( | 29) 7 | 300( | 9)13 | 309( | 28) 8 |
| | | | 337( | 17)10 | 354( | 15)11 | 369( | 93) 4 | 462( | 8)14 |
| | | | 470( | 5)15 | 475( | 119) 3 | 594( | 171) 2 | 765( | 91) 5 |
| SspW I | gcnnnnn/nngc | 17 | 1( | 30)10 | 11( | 9)12 | 40( | 3)17 | 43( | 45) 9 |
| | | | 38( | 69) 7 | 157( | 104) 3 | 261( | 107) 2 | 368( | 4)16 |
| | | | 372( | 93) 4 | 465( | 89) 5 | 554( | 9)13 | 563( | 98) 6 |
| | | | 651( | 17)11 | 668( | 9)14 | 677( | 3)18 | 680( | 119) 1 |
| | | | 799( | 9)15 | 808( | 48) 8 | | | | |
| Fnu4H I | gc/ngc | 19 | 1( | 39) 9 | 40( | 9)14 | 49( | 3)17 | 52( | 23)12 |
| | | | 75( | 85) 3 | 151( | 48) 7 | 209( | 52) 6 | 261( | 3)18 |
| | | | 264( | 3)19 | 267( | 27)10 | 294( | 46) 8 | 340( | 211) 1 |
| | | | 551( | 109) 2 | 560( | 5)16 | 665( | 12)13 | 677( | 9)15 |
| | | | 686( | 24)11 | 710( | 86) 4 | 796( | 3)20 | 799( | 57) 5 |

400 sites found

No Sites found for the following Restriction Endonucleases

| | | | | | | | |
|---|---|---|---|---|---|---|---|
| Afl II | c/ttaag | Eco57 I | ctgaag 16/14 | PpuM I | rg/gwccy | | |
| Afl III | a/crygt | EcoR I | g/aattc | PshA I | gacnn/nngtc | | |
| Age I | a/ccggt | EcoR V | gat/atc | Psc I | ctgca/g | | |
| Apa I | gggcc/c | Esp I | gc/tnagc | Pvu I | cgat/cg | | |
| ApaL I | g/tgcac | Fse I | ggccgg/cc | Rma I | c/tag | | |
| Ase I | at/taat | Gsu I | ctggag 16/14 | Rsr II | cg/gwccg | | |
| Avr II | c/ctagg | Hae I | wgg/ccw | Sap I | gcttctc 1/4 | | |
| Bcl I | t/gatca | Hind III | a/agctt | Sca I | agt/act | | |
| Bsa I | ggtctc 1/5 | Hpa I | gtt/aac | Sfe I | c/tryag | | |
| BsaA I | yac/gtr | Mlu I | a/cgcgt | Sna I | gta/tac | | |
| Bsa3 I | gacnn/nnatc | Mme I | tccrac 20/18 | SnaB I | tac/gta | | |
| Bsg I | gtgcag 16/14 | Msc I | tgg/cca | Spe I | a/ctagt | | |
| Bsm I | gaatgc 1/-1 | Mse I | t/taa | Sph I | gcatg/c | | |
| Bsp120 I | g/ggcc | Nco I | c/catgg | Spl I | c/gtacg | | |
| BspE I | t/ccgga | Nde I | ca/tatg | Sse8387 I | cctgca/gg | | |
| BspH I | t/catga | Nhe I | g/ctagc | Stu I | agg/cct | | |
| Bst3 I | ct/cgaa | Not I | gc/ggccgc | Sty I | c/cwwgg | | |
| BstE II | g/gtnacc | Nru I | tcg/cga | Swa I | attt/aaat | | |
| BsuJ6 I | cc/tnagg | Nsi I | atgca/t | Tfi I | g/awtc | | |
| Cla I | at/cgat | Nsp I | rcatg/y | Tth111 I | gacn/nngtc | | |
| Dra I | ttt/aaa | Nsp7524 I | r/catgy | Tth111 II | caarca 11/9 | | |
| Dra III | cacnnn/gtg | NspC I | rcatg/y | Xba I | t/ctaga | | |
| Drd I | gacnnnn/nngtc | Pac I | ttaat/taa | Xca I | gta/tac | | |
| Eco47 III | agc/gct | Pml I | cac/gtg | Xmn I | gaann/nnttc | | |

*Annex IV*

PEPTIDESORT of: LHP.seq check: 6672 from: 1 to: 100

FROMSTADEN of: LHP.txt check: 6672 from: 1 to: 100
<---No Contig Comments--->

With Enzymes: *

June 26, 1997 11:54 ..

Digest with: Tryp.  Peptides Sorted by Position

```
Pos  From    To    Mol Wt   Ret2.1  Ret7.4   Chg  Aro  Acid Base Sulf Phil Phob
 1    1 -     5     608.8     9.9    -7.3    0.0   0    1    1    2    2    3
   A1,E1,K1,M2 Iso=6.44 Ext=0
 2    6 -    20    1579.6     5.7   -18.5   -2.0   1    3    1    0    8    7
   A3,D1,E2,F1,G2,L1,N1,Q1,R1,T2 Iso=4.00 Ext=0
 3   21 -    26     631.7    18.1    15.2    0.0   0    1    1    0    3    3
   D1,G1,I1,K1,L1,S1 Iso=6.31 Ext=0
 4   27 -    44    2004.1    19.4     4.5   -1.0   1    2    1    0   11    7
   A1,D1,E1,G2,I1,L1,Q4,R1,S2,T2,V1,W1 Iso=4.24 Ext=5690
 5   45 -    57    1142.3     6.0     6.5    1.0   0    0    1    0    3   10
   A6,G2,Q1,R1,T1,V2 Iso=10.53 Ext=0
 6   58 -    64     806.9     5.4    -8.8    0.0   1    1    1    0    4    3
   A2,E1,F1,K1,N1,Q1 Iso=6.44 Ext=0
 7   65 -    66     274.3     0.8    -5.3    1.0   0    0    1    0    2    0
   K1,Q1 Iso=9.67 Ext=0
 8   67 -    77    1317.4    11.5    -6.9   -2.0   0    3    1    0    8    3
   D1,E2,I2,L1,N1,Q1,R1,S1,T1 Iso=4.00 Ext=0
 9   78 -    85     908.0     4.2     1.1    1.0   1    0    1    0    4    4
   A1,G1,Q2,R1,S1,V1,Y1 Iso=9.75 Ext=1280
10   86 -   100    1668.8     1.6   -31.6   -3.0   1    3    0    1    9    6
   A2,D1,E2,F1,G1,L1,M1,Q4,S2 Iso=3.47 Ext=0
```

Digest with: Tryp.  Peptides Sorted by Weight

```
Pos  From    To    Mol Wt   Ret2.1  Ret7.4   Chg  Aro  Acid Base Sulf Phil Phob
 7   65 -    66     274.3     0.8    -5.3    1.0   0    0    1    0    2    0
 1    1 -     5     608.8     9.9    -7.3    0.0   0    1    1    2    2    3
 3   21 -    26     631.7    18.1    15.2    0.0   0    1    1    0    3    3
 6   58 -    64     806.9     5.4    -8.8    0.0   1    1    1    0    4    3
 9   78 -    85     908.0     4.2     1.1    1.0   1    0    1    0    4    4
 5   45 -    57    1142.3     6.0     6.5    1.0   0    0    1    0    3   10
 8   67 -    77    1317.4    11.5    -6.9   -2.0   0    3    1    0    8    3
 2    6 -    20    1579.6     5.7   -18.5   -2.0   1    3    1    0    8    7
10   86 -   100    1668.8     1.6   -31.6   -3.0   1    3    0    1    9    6
 4   27 -    44    2004.1    19.4     4.5   -1.0   1    2    1    0   11    7
```

Digest with: Tryp.  Peptides Sorted by Retention

```
Pos  From    To    Mol Wt   Ret2.1  Ret7.4   Chg  Aro  Acid Base Sulf Phil Phob
 7   65 -    66     274.3     0.8    -5.3    1.0   0    0    1    0    2    0
10   86 -   100    1668.8     1.6   -31.6   -3.0   1    3    0    1    9    6
 9   78 -    85     908.0     4.2     1.1    1.0   1    0    1    0    4    4
 6   58 -    64     806.9     5.4    -8.8    0.0   1    1    1    0    4    3
 2    6 -    20    1579.6     5.7   -18.5   -2.0   1    3    1    0    8    7
 5   45 -    57    1142.3     6.0     6.5    1.0   0    0    1    0    3   10
 1    1 -     5     608.8     9.9    -7.3    0.0   0    1    1    2    2    3
 8   67 -    77    1317.4    11.5    -6.9   -2.0   0    3    1    0    8    3
 3   21 -    26     631.7    18.1    15.2    0.0   0    1    1    0    3    3
 4   27 -    44    2004.1    19.4     4.5   -1.0   1    2    1    0   11    7
```

Digest with: Chymo.  Peptides Sorted by Position

```
Pos  From    To    Mol Wt   Ret2.1  Ret7.4   Chg  Aro  Acid Base Sulf Phil Phob
 1    1 -    18    1885.1    21.1    -9.1   -2.0   1    3    1    2    8   10
   A4,D1,E2,F1,G2,K1,L1,M2,N1,Q1,T2 Iso=4.00 Ext=0
 2   19 -    43    2747.0    23.5     3.4   -2.0   1    4    2    0   15   10
   A1,D2,E2,G3,I2,K1,L2,Q4,R1,S3,T2,V1,W1 Iso=4.17 Ext=5690
 3   44 -    58    1445.6    15.4    20.5    2.0   1    0    2    0    4   11
```

-93-

```
A6,F1,G2,Q1,R2,T1,V2 Iso=12.50 Ext=0
 4    59 -   83   2862.1    -3.3   -33.3    -1.0     1    4    3    0   16    9
A3,D1,E3,G1,I2,K2,L1,N2,Q5,R1,S1,T1,V1,Y1 Iso=4.70 Ext=1280
 5    84 -  100   1912.0    -6.6   -29.6    -2.0     1    3    1    1   11    6
A2,D1,E2,F1,G1,L1,M1,Q4,R1,S3 Iso=4.00 Ext=0
```

Digest with: Chymo.  Peptides Sorted by Weight

```
Pos From    To   Mol Wt  Ret2.1  Ret7.4   Chg  Aro Acid Base Sulf Phil Phob
 3    44 -   58   1445.6   15.4    20.5    2.0   1    0    2    0    4   11
 1     1 -   18   1885.1   21.1    -9.1   -2.0   1    3    1    2    8   10
 5    84 -  100   1912.0   -6.6   -29.6   -2.0   1    3    1    1   11    6
 2    19 -   43   2747.0   23.5     3.4   -2.0   1    4    2    0   15   10
 4    59 -   83   2862.1   -3.3   -33.3   -1.0   1    4    3    0   16    9
```

Digest with: Chymo.  Peptides Sorted by Retention

```
Pos From    To   Mol Wt  Ret2.1  Ret7.4   Chg  Aro Acid Base Sulf Phil Phob
 5    84 -  100   1912.0   -6.6   -29.6   -2.0   1    3    1    1   11    6
 4    59 -   83   2862.1   -3.3   -33.3   -1.0   1    4    3    0   16    9
 3    44 -   58   1445.6   15.4    20.5    2.0   1    0    2    0    4   11
 1     1 -   18   1885.1   21.1    -9.1   -2.0   1    3    1    2    8   10
 2    19 -   43   2747.0   23.5     3.4   -2.0   1    4    2    0   15   10
```

Digest with: Clos.  Peptides Sorted by Position

```
Pos From    To   Mol Wt  Ret2.1  Ret7.4   Chg  Aro Acid Base Sulf Phil Phob
 1     1 -   20   2170.4    9.1   -25.2   -2.0   1    4    2    2   10   10
A4,D1,E3,F1,G2,K1,L1,M2,N1,Q1,R1,T2 Iso=4.24 Ext=0
 2    21 -   44   2617.8   31.0    20.3   -1.0   1    3    2    0   14   10
A1,D2,E1,G3,I2,K1,L2,Q4,R1,S3,T2,V1,W1 Iso=4.42 Ext=5690
 3    45 -   57   1142.3    6.0     6.5    1.0   0    0    1    0    3   10
A6,G2,Q1,R1,T1,V2 Iso=10.53 Ext=0
 4    58 -   77   2362.6    4.7   -19.8   -1.0   1    4    3    0   14    6
A2,D1,E3,F1,I2,K2,L1,N2,Q3,R1,S1,T1 Iso=4.70 Ext=0
 5    78 -   85    908.0    4.2     1.1    1.0   1    0    1    0    4    4
A1,G1,Q2,R1,S1,V1,Y1 Iso=9.75 Ext=1280
 6    86 -  100   1668.8    1.6   -31.6   -3.0   1    3    0    1    9    6
A2,D1,E2,F1,G1,L1,M1,Q4,S2 Iso=3.47 Ext=0
```

Digest with: Clos.  Peptides Sorted by Weight

```
Pos From    To   Mol Wt  Ret2.1  Ret7.4   Chg  Aro Acid Base Sulf Phil Phob
 5    78 -   85    908.0    4.2     1.1    1.0   1    0    1    0    4    4
 3    45 -   57   1142.3    6.0     6.5    1.0   0    0    1    0    3   10
 6    86 -  100   1668.8    1.6   -31.6   -3.0   1    3    0    1    9    6
 1     1 -   20   2170.4    9.1   -25.2   -2.0   1    4    2    2   10   10
 4    58 -   77   2362.6    4.7   -19.8   -1.0   1    4    3    0   14    6
 2    21 -   44   2617.8   31.0    20.3   -1.0   1    3    2    0   14   10
```

Digest with: Clos.  Peptides Sorted by Retention

```
Pos From    To   Mol Wt  Ret2.1  Ret7.4   Chg  Aro Acid Base Sulf Phil Phob
 6    86 -  100   1668.8    1.6   -31.6   -3.0   1    3    0    1    9    6
 5    78 -   85    908.0    4.2     1.1    1.0   1    0    1    0    4    4
 4    58 -   77   2362.6    4.7   -19.8   -1.0   1    4    3    0   14    6
 3    45 -   57   1142.3    6.0     6.5    1.0   0    0    1    0    3   10
 1     1 -   20   2170.4    9.1   -25.2   -2.0   1    4    2    2   10   10
 2    21 -   44   2617.8   31.0    20.3   -1.0   1    3    2    0   14   10
```

Digest with: CnBr.  Peptides Sorted by Position

```
                Digest with: Myxo.  Peptides Sorted by Weight

Pos  From    To   Mol Wt  Ret2.1  Ret7.4   Chg  Aro Acid Base Sulf Phil Phob
 4    65 -   66    274.3     0.8    -5.3   1.0    0    0    1    0    2    0
 1     1 -    5    608.8     9.9    -7.3   0.0    0    1    1    2    2    3
 2     6 -   26   2193.3    17.3    -2.7  -2.0    1    4    2    0   11   10
 5    67 -  100   3858.1     4.3   -36.2  -4.0    2    6    2    1   21   13
 3    27 -   64   3917.3    17.8     3.4   0.0    2    3    3    0   18   20

Digest with: Myxo.  Peptides Sorted by Retention

Pos  From    To   Mol Wt  Ret2.1  Ret7.4   Chg  Aro Acid Base Sulf Phil Phob
 4    65 -   66    274.3     0.8    -5.3   1.0    0    0    1    0    2    0
 5    67 -  100   3858.1     4.3   -36.2  -4.0    2    6    2    1   21   13
 1     1 -    5    608.8     9.9    -7.3   0.0    0    1    1    2    2    3
 2     6 -   26   2193.3    17.3    -2.7  -2.0    1    4    2    0   11   10
 3    27 -   64   3917.3    17.8     3.4   0.0    2    3    3    0   18   20

Digest with: Staph.  Peptides Sorted by Position

Pos  From    To   Mol Wt  Ret2.1  Ret7.4   Chg  Aro Acid Base Sulf Phil Phob
 1     1 -    3    349.4     6.0   -12.2  -1.0    0    1    0    1    1    2
A1,E1,M1 Iso=3.90 Ext=0
 2     4 -   14   1164.3     9.9   -10.4  -1.0    0    2    1    1    6    5
A2,D1,E1,G1,K1,L1,M1,Q1,T2 Iso=4.24 Ext=0
 3    15 -   19    536.5    10.7    -4.6  -1.0    1    1    0    0    2    3
A1,E1,F1,G1,N1 Iso=3.90 Ext=0
 4    20 -   33   1601.8    14.9     0.6  -1.0    0    3    2    0    9    5
D2,E1,G1,I2,K1,L1,Q2,R1,S1,T1,V1 Iso=4.42 Ext=0
 5    34 -   60   2719.0    21.5    18.5   1.0    2    1    2    0   11   16
A7,E1,F1,G4,L1,Q4,R2,S2,T2,V2,W1 Iso=10.38 Ext=5690
 6    61 -   68    916.0   -14.2   -26.7   1.0    0    1    2    0    6    2
A2,E1,K2,N1,Q2 Iso=9.51 Ext=0
 7    69 -   71    375.4     6.2   -16.9  -2.0    0    2    0    0    2    1
D1,E1,L1 Iso=3.58 Ext=0
 8    72 -   88   1908.0     9.1     8.2   0.0    1    2    2    0   10    7
A2,D1,E1,G1,I2,N1,Q2,R2,S2,T1,V1,Y1 Iso=6.51 Ext=1280
 9    89 -   89    147.1    -1.0   -17.5  -1.0    0    1    0    0    1    0
E1 Iso=3.90 Ext=0
10    90 -  100   1224.4    19.5     9.9   0.0    1    0    0    1    6    5
A1,F1,G1,L1,M1,Q4,S2 Iso=6.06 Ext=0

Digest with: Staph.  Peptides Sorted by Weight

Pos  From    To   Mol Wt  Ret2.1  Ret7.4   Chg  Aro Acid Base Sulf Phil Phob
 9    89 -   89    147.1    -1.0   -17.5  -1.0    0    1    0    0    1    0
 1     1 -    3    349.4     6.0   -12.2  -1.0    0    1    0    1    1    2
 7    69 -   71    375.4     6.2   -16.9  -2.0    0    2    0    0    2    1
 3    15 -   19    536.5    10.7    -4.6  -1.0    1    1    0    0    2    3
 6    61 -   68    916.0   -14.2   -26.7   1.0    0    1    2    0    6    2
 2     4 -   14   1164.3     9.9   -10.4  -1.0    0    2    1    1    6    5
10    90 -  100   1224.4    19.5     9.9   0.0    1    0    0    1    6    5
 4    20 -   33   1601.8    14.9     0.6  -1.0    0    3    2    0    9    5
 8    72 -   88   1908.0     9.1     8.2   0.0    1    2    2    0   10    7
 5    34 -   60   2719.0    21.5    18.5   1.0    2    1    2    0   11   16

Digest with: Staph.  Peptides Sorted by Retention

Pos  From    To   Mol Wt  Ret2.1  Ret7.4   Chg  Aro Acid Base Sulf Phil Phob
 6    61 -   68    916.0   -14.2   -26.7   1.0    0    1    2    0    6    2
 9    89 -   89    147.1    -1.0   -17.5  -1.0    0    1    0    0    1    0
 1     1 -    3    349.4     6.0   -12.2  -1.0    0    1    0    1    1    2
 7    69 -   71    375.4     6.2   -16.9  -2.0    0    2    0    0    2    1
 8    72 -   88   1908.0     9.1     8.2   0.0    1    2    2    0   10    7
```

```
                  Digest with: CnBr.  Peptides Sorted by Position

Pos  From    To   Mol Wt  Ret2.1  Ret7.4   Chg  Aro Acid Base Sulf Phil Phob
 1    1 -     1    149.2   13.6     4.2    0.0   0   0    0    1    0    1
M1 Iso=6.06 Ext=0
 2    2 -     4    349.4    6.0   -12.2   -1.0   0   1    0    1    1    2
A1,E1,M1 Iso=3.90 Ext=0
 3    5 -    98  10112.9    4.1   -52.1   -4.0   4  13    9    1   53   41
A15,D5,E8,F2,G8,I4,K4,L5,M1,N3,Q15,R5,S7,T6,V4,W1,Y1 Iso=4.50 Ext=6970
 4   99 -   100    222.2   19.9    12.6    0.0   1   0    0    0    0    2
F1,G1 Iso=6.06 Ext=0

Digest with: CnBr.  Peptides Sorted by Weight

Pos  From    To   Mol Wt  Ret2.1  Ret7.4   Chg  Aro Acid Base Sulf Phil Phob
 1    1 -     1    149.2   13.6     4.2    0.0   0   0    0    1    0    1
 4   99 -   100    222.2   19.9    12.6    0.0   1   0    0    0    0    2
 2    2 -     4    349.4    6.0   -12.2   -1.0   0   1    0    1    1    2
 3    5 -    98  10112.9    4.1   -52.1   -4.0   4  13    9    1   53   41

Digest with: CnBr.  Peptides Sorted by Retention

Pos  From    To   Mol Wt  Ret2.1  Ret7.4   Chg  Aro Acid Base Sulf Phil Phob
 3    5 -    98  10112.9    4.1   -52.1   -4.0   4  13    9    1   53   41
 2    2 -     4    349.4    6.0   -12.2   -1.0   0   1    0    1    1    2
 1    1 -     1    149.2   13.6     4.2    0.0   0   0    0    1    0    1
 4   99 -   100    222.2   19.9    12.6    0.0   1   0    0    0    0    2

Digest with: IBzO.  Peptides Sorted by Position

Pos  From    To   Mol Wt  Ret2.1  Ret7.4   Chg  Aro Acid Base Sulf Phil Phob
 1    1 -    43   4614.0   38.1    -5.1   -4.0   2   7    3    2   23   20
A5,D3,E4,F1,G5,I2,K2,L3,M2,N1,Q5,R1,S3,T4,V1,W1 Iso=4.04 Ext=5690
 2   44 -   100   6183.7   -7.5   -41.2   -1.0   3   7    6    1   31   26
A11,D2,E5,F2,G4,I2,K2,L2,M1,N2,Q10,R4,S4,T2,V3,Y1 Iso=4.97 Ext=1280

Digest with: IBzO.  Peptides Sorted by Weight

Pos  From    To   Mol Wt  Ret2.1  Ret7.4   Chg  Aro Acid Base Sulf Phil Phob
 1    1 -    43   4614.0   38.1    -5.1   -4.0   2   7    3    2   23   20
 2   44 -   100   6183.7   -7.5   -41.2   -1.0   3   7    6    1   31   26

Digest with: IBzO.  Peptides Sorted by Retention

Pos  From    To   Mol Wt  Ret2.1  Ret7.4   Chg  Aro Acid Base Sulf Phil Phob
 2   44 -   100   6183.7   -7.5   -41.2   -1.0   3   7    6    1   31   26
 1    1 -    43   4614.0   38.1    -5.1   -4.0   2   7    3    2   23   20

Digest with: Myxo.  Peptides Sorted by Position

Pos  From    To   Mol Wt  Ret2.1  Ret7.4   Chg  Aro Acid Base Sulf Phil Phob
 1    1 -     5    608.8    9.9    -7.3    0.0   0   1    1    2    2    3
A1,E1,K1,M2 Iso=6.44 Ext=0
 2    6 -    26   2193.3   17.3    -2.7   -2.0   1   4    2    0   11   10
A3,D2,E2,F1,G3,I1,K1,L2,N1,Q1,R1,S1,T2 Iso=4.17 Ext=0
 3   27 -    64   3917.3   17.8     3.4    0.0   2   3    3    0   18   20
A9,D1,E2,F1,G4,I1,K1,L1,N1,Q6,R2,S2,T3,V3,W1 Iso=6.62 Ext=5690
 4   65 -    66    274.3    0.8    -5.3    1.0   0   0    1    0    2    0
K1,Q1 Iso=9.67 Ext=0
 5   67 -   100   3858.1    4.3   -16.2   -4.0   2   6    2    1   21   13
A3,D2,E4,F1,G2,I2,L2,M1,N1,Q7,R2,S4,T1,V1,Y1 Iso=3.92 Ext=1280
```

```
  2    4 -  14  1164.3   9.9  -10.4  -1.0   0   2   1   1   6   5
  3   15 -  19   536.5  10.7   -4.6  -1.0   1   1   0   0   2   3
  4   20 -  33  1601.8  14.9    0.6  -1.0   0   3   2   0   9   5
 10   90 - 100  1224.4  19.5    9.9   0.0   1   0   0   1   6   5
  5   34 -  60  2719.0  21.5   18.5   1.0   2   1   2   0  11  16
```

Digest with: TrypK. Peptides Sorted by Position

```
Pos  From    To    Mol Wt  Ret2.1  Ret7.4  Chg  Aro Acid Base Sulf Phil Phob
  1    1 -    5   608.8     9.9    -7.3    0.0   0   1   1   2   2   3
A1,E1,K1,M2 Iso=6.44 Ext=0
  2    6 -   26  2193.3    17.3    -2.7   -2.0   1   4   2   0  11  10
A3,D2,E2,F1,G3,I1,K1,L2,N1,Q1,R1,S1,T2 Iso=4.17 Ext=0
  3   27 -   64  3917.3    17.8     3.4    0.0   2   3   3   0  18  20
A9,D1,E2,F1,G4,I1,K1,L1,N1,Q6,R2,S2,T3,V3,W1 Iso=6.62 Ext=5690
  4   65 -   66   274.3     0.8    -5.3    1.0   0   0   1   0   2   0
K1,Q1 Iso=9.67 Ext=0
  5   67 -  100  3858.1     4.3   -36.2   -4.0   2   6   2   1  21  13
A3,D2,E4,F1,G2,I2,L2,M1,N1,Q7,R2,S4,T1,V1,Y1 Iso=3.92 Ext=1280
```

Digest with: TrypK. Peptides Sorted by Weight

```
Pos  From    To    Mol Wt  Ret2.1  Ret7.4  Chg  Aro Acid Base Sulf Phil Phob
  4   65 -   66   274.3     0.8    -5.3    1.0   0   0   1   0   2   0
  1    1 -    5   608.8     9.9    -7.3    0.0   0   1   1   2   2   3
  2    6 -   26  2193.3    17.3    -2.7   -2.0   1   4   2   0  11  10
  5   67 -  100  3858.1     4.3   -36.2   -4.0   2   6   2   1  21  13
  3   27 -   64  3917.3    17.8     3.4    0.0   2   3   3   0  18  20
```

Digest with: TrypK. Peptides Sorted by Retention

```
Pos  From    To    Mol Wt  Ret2.1  Ret7.4  Chg  Aro Acid Base Sulf Phil Phob
  4   65 -   66   274.3     0.8    -5.3    1.0   0   0   1   0   2   0
  5   67 -  100  3858.1     4.3   -36.2   -4.0   2   6   2   1  21  13
  1    1 -    5   608.8     9.9    -7.3    0.0   0   1   1   2   2   3
  2    6 -   26  2193.3    17.3    -2.7   -2.0   1   4   2   0  11  10
  3   27 -   64  3917.3    17.8     3.4    0.0   2   3   3   0  18  20
```

Digest with: TrypR. Peptides Sorted by Position

```
Pos  From    To    Mol Wt  Ret2.1  Ret7.4  Chg  Aro Acid Base Sulf Phil Phob
  1    1 -   20  2170.4     9.1   -25.2   -2.0   1   4   3   2  10  10
A4,D1,E3,F1,G2,K1,L1,M2,N1,Q1,R1,T2 Iso=4.24 Ext=0
  2   21 -   44  2617.8    31.0    20.3   -1.0   1   3   2   0  14  10
A1,D2,E1,G3,I2,K1,L2,Q4,R1,S3,T2,V1,W1 Iso=4.42 Ext=5690
  3   45 -   57  1142.3     6.0     6.5    1.0   0   0   1   0   3  10
A6,G2,Q1,R1,T1,V2 Iso=10.53 Ext=0
  4   58 -   77  2362.6     4.7   -19.8   -1.0   1   4   3   0  14   6
A2,D1,E3,F1,I2,K2,L1,N2,Q3,R1,S1,T1 Iso=4.70 Ext=0
  5   78 -   85   908.0     4.2     1.1    1.0   1   0   1   0   4   4
A1,G1,Q2,R1,S1,V1,Y1 Iso=9.75 Ext=1280
  6   86 -  100  1668.8     1.6   -31.6   -3.0   1   3   0   1   9   6
A2,D1,E2,F1,G1,L1,M1,Q4,S2 Iso=3.47 Ext=0
```

Digest with: TrypR. Peptides Sorted by Weight

```
Pos  From    To    Mol Wt  Ret2.1  Ret7.4  Chg  Aro Acid Base Sulf Phil Phob
  5   78 -   85   908.0     4.2     1.1    1.0   1   0   1   0   4   4
  3   45 -   57  1142.3     6.0     6.5    1.0   0   0   1   0   3  10
  6   86 -  100  1668.8     1.6   -31.6   -3.0   1   3   0   1   9   6
  1    1 -   20  2170.4     9.1   -25.2   -2.0   1   4   3   2  10  10
  4   58 -   77  2362.6     4.7   -19.8   -1.0   1   4   3   0  14   6
  2   21 -   44  2617.8    31.0    20.3   -1.0   1   3   2   0  14  10
```

```
              Digest with: TrypR.  Peptides Sorted by Retention

Pos  From    To   Mol Wt  Ret2.1  Ret7.4   Chg  Aro Acid Base Sulf Phil Phob
  6   86  -  100  1668.8    1.6   -31.6   -3.0    1   3    0    1    9    6
  5   78  -   85   908.0    4.2     1.1    1.0    1   0    1    0    4    4
  4   58  -   77  2362.6    4.7   -19.8   -1.0    1   4    3    0   14    6
  3   45  -   57  1142.3    6.0     6.5    1.0    0   0    1    0    3   10
  1    1  -   20  2170.4    9.1   -25.2   -2.0    1   4    2    2   10   10
  2   21  -   44  2617.8   31.0    20.3   -1.0    1   3    2    0   14   10

Digest with: AspN.  Peptides Sorted by Position

Pos  From    To   Mol Wt  Ret2.1  Ret7.4   Chg  Aro Acid Base Sulf Phil Phob
  1    1  -    6   709.9   11.4    -4.6    0.0    0   1    1    2    3    3
 A1,E1,K1,M2,T1 Iso=6.44 Ext=0
  2    7  -   23  1735.8   11.8    -6.1   -2.0    1   3    1    0    8    9
 A3,D1,E2,F1,G3,I1,L1,N1,Q1,R1,S1,T1 Iso=4.00 Ext=0
  3   24  -   29   716.8   21.3    11.9    0.0    0   1    1    0    4    2
 D1,I1,K1,L1,Q1,T1 Iso=6.31 Ext=0
  4   30  -   69  4201.6    1.3   -26.0    0.0    2   4    4    0   20   20
 A9,D1,E3,F1,G4,K2,L2,N1,Q7,R2,S2,T2,V3,W1 Iso=6.69 Ext=5690
  5   70  -   86  1908.0    9.1     8.2    0.0    1   2    2    0   10    7
 A2,D1,E1,G1,I2,N1,Q2,R2,S2,T1,V1,Y1 Iso=6.51 Ext=1280
  6   87  -  100  1597.7    1.7   -32.1   -3.0    1   3    0    1    9    5
 A1,D1,E2,F1,G1,L1,M1,Q4,S2 Iso=3.47 Ext=0

Digest with: AspN.  Peptides Sorted by Weight

Pos  From    To   Mol Wt  Ret2.1  Ret7.4   Chg  Aro Acid Base Sulf Phil Phob
  1    1  -    6   709.9   11.4    -4.6    0.0    0   1    1    2    3    3
  3   24  -   29   716.8   21.3    11.9    0.0    0   1    1    0    4    2
  6   87  -  100  1597.7    1.7   -32.1   -3.0    1   3    0    1    9    5
  2    7  -   23  1735.8   11.8    -6.1   -2.0    1   3    1    0    8    9
  5   70  -   86  1908.0    9.1     8.2    0.0    1   2    2    0   10    7
  4   30  -   69  4201.6    1.3   -26.0    0.0    2   4    4    0   20   20

Digest with: AspN.  Peptides Sorted by Retention

Pos  From    To   Mol Wt  Ret2.1  Ret7.4   Chg  Aro Acid Base Sulf Phil Phob
  4   30  -   69  4201.6    1.3   -26.0    0.0    2   4    4    0   20   20
  6   87  -  100  1597.7    1.7   -32.1   -3.0    1   3    0    1    9    5
  5   70  -   86  1908.0    9.1     8.2    0.0    1   2    2    0   10    7
  1    1  -    6   709.9   11.4    -4.6    0.0    0   1    1    2    3    3
  2    7  -   23  1735.8   11.8    -6.1   -2.0    1   3    1    0    8    9
  3   24  -   29   716.8   21.3    11.9    0.0    0   1    1    0    4    2
```

Summary for whole sequence:

Molecular weight  =  10779.72      Residues  =    100
Average Residue Weight = 107.797   Charged   =   -5
Isoelectric point =  4.41
Extinction coefficient =  6970

| Residue  | Number | Mole Percent |
|----------|--------|--------------|
| A = Ala  | 16     | 16.000       |
| B = Asx  | 0      | 0.000        |
| C = Cys  | 0      | 0.000        |
| D = Asp  | 5      | 5.000        |
| E = Glu  | 9      | 9.000        |
| F = Phe  | 3      | 3.000        |
| G = Gly  | 9      | 9.000        |
| H = His  | 0      | 0.000        |
| I = Ile  | 4      | 4.000        |
| K = Lys  | 4      | 4.000        |

```
L = Leu      5      5.000
M = Met      3      3.000
N = Asn      3      3.000
P = Pro      0      0.000
Q = Gln     15     15.000
R = Arg      5      5.000
S = Ser      7      7.000
T = Thr      6      6.000
V = Val      4      4.000
W = Trp      1      1.000
Y = Tyr      1      1.000
Z = Glx      0      0.000
A + G                25     25.000
S + T                13     13.000
D + E                14     14.000
D + E + N + Q        32     32.000
H + K + R             9      9.000
D + E + H + K + R    23     23.000
I + L + M + V        16     16.000
F + W + Y             5      5.000
```

Enzymes that do cut:

| Tryp | Chymo | Clos | CnBr | IBzO | Myxo | Staph | TrypK |
|------|-------|------|------|------|------|-------|-------|
| TrypR | AspN | | | | | | |

Enzymes that do not cut:

| NH2OH | NTCB | pH2.5 | ProEn | NoCut |
|-------|------|-------|-------|-------|

What is claimed is:

1. A recombinant cell host comprising a purified polynucleotide having the sequence in SEQ ID NO:2 or a recombinant vector comprising SEQ ID NO:2, wherein said cell host is a *Mycobacterium smegmatis*.

2. An isolated polynucleotide which is selected from the group consisting of: SEQ ID NO:14, SEQ ID NO:15, and SEQ ID NO:16.

3. A pair of oligonucleotide primers useful as a primer or a probe, which pair is selected from the group consisting of:
   a) SEQ ID NO 14 and SEQ ID NO 15; and
   b) SEQ ID NO 14 and SEQ ID NO 16.

4. A purified polynucleotide comprising SEQ ID NO:2 and which encodes a LHP polypeptide.

5. A purified polynucleotide comprising SEQ ID NO:3 and which encodes a LHP polypeptide.

6. A purified polynucleotide selected from the group consisting of
   a) a polynucleotide comprising SEQ ID NO:1;
   b) a polynucleotide comprising SEQ ID NO:2;
   c) a polynucleotide comprising SEQ ID NO:3;
   d) a polynucleotide which is fully complementary to one of SEQ ID NOS:1, 2, or 3; and
   e) a polynucleotide which hybridizes under stringent conditions to one of SEQ ID NOS:1, 2, or 3.

7. The purified polynucleotide of claim 6, which encodes a protein comprising the amino acid sequence SEQ ID NO:5.

8. A polynucleotide according to claim 6 which is labeled with a marker compound.

9. A recombinant vector comprising the polynucleotide of claim 6.

10. A host cell comprising the recombinant vector of claim 9.

11. The cell host according to claim 10 which is a mycobacterium cell host belonging to the *Mycobacterium tuberculosis* complex.

12. The cell host according to claim 11 which is *Mycobacterium tuberculosis*.

13. The cell host according to claim 11 which is *Mcobacterium bovis*-BCG.

14. An immunogenic composition comprising a cell host containing at least one purified polynucleotide of claim 6.

15. The immunogenic composition of claim 14, wherein said isolated polynucleotide is contained in a recombinant vector.

16. The immunogenic composition according to claim 14, wherein the cell host is a eukaryotic cell host.

17. The immunogenic composition according to claim 14, wherein the cell host is a prokaryotic cell host.

18. The immunogenic composition according to claim 17, wherein the cell host is selected from the group consisting of:
   a) an attenuated bacterium belonging to the tuberculosis complex;
   b) *E. coli*;
   c) a bacterium belonging to the Salmonella genus; and
   d) a bacterium belonging to the Pseudomonas genus.

19. A purified polynucleotide consisting of SEQ ID NO:4 or a sequence which is complementary to SEQ ID NO:4.

20. The polynucleotide according to claim 19 which is labeled with a marker compound.

21. A recombinant vector comprising the polynucleotide of claim 19.

22. A host cell comprising the recombinant vector of claim 21.

23. An *E. coli* strain deposited at the CNCM under the Accession Number I-1707.

24. An *E. coli* strain deposited at the CNCM under the Accession Number I-1705.

25. An *E. coli* strain deposited at the CNCM under the Accession Number I-1845.

26. An *E. coli* strain deposited at the CNCM under the Accession Number I-1706.

* * * * *